US008883816B2

(12) United States Patent
Tafesse et al.

(10) Patent No.: US 8,883,816 B2
(45) Date of Patent: Nov. 11, 2014

(54) FUSED AND SPIROCYCLE COMPOUNDS AND THE USE THEREOF

(71) Applicant: Purdue Pharma L.P., Stamford, CT (US)

(72) Inventors: Laykea Tafesse, Robbinsville, NJ (US); Khondaker Islam, Arlington, VA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 13/953,205

(22) Filed: Jul. 29, 2013

(65) Prior Publication Data

US 2014/0045875 A1    Feb. 13, 2014

Related U.S. Application Data

(62) Division of application No. 13/486,267, filed on Jun. 1, 2012, now Pat. No. 8,546,417, which is a division of application No. 11/991,626, filed as application No. PCT/EP2006/008788 on Sep. 8, 2006, now Pat. No. 8,193,208.

(60) Provisional application No. 60/715,174, filed on Sep. 9, 2005.

(51) Int. Cl.
*A61K 31/438* (2006.01)
*C07D 221/20* (2006.01)

(52) U.S. Cl.
USPC ............................................ 514/278; 546/17

(58) Field of Classification Search
USPC ............................................ 514/278; 546/17
See application file for complete search history.

(56) References Cited

U.S. PATENT DOCUMENTS

| | | | |
|---|---|---|---|
| 3,125,580 A | 3/1964 | Janssen |
| 3,686,186 A | 8/1972 | Houlihan et al. |
| 3,745,165 A | 7/1973 | Houlihan et al. |
| 3,959,475 A | 5/1976 | Bauer et al. |
| 3,962,259 A | 6/1976 | Bauer et al. |
| 3,985,889 A | 10/1976 | Bauer et al. |
| 4,116,963 A | 9/1978 | Adelstein |
| 4,188,485 A | 2/1980 | Kukla |
| 4,233,307 A | 11/1980 | Ono et al. |
| 4,409,229 A | 10/1983 | Ong et al. |
| 4,452,802 A | 6/1984 | Kosley, Jr. et al. |
| 4,524,207 A | 6/1985 | Ong et al. |
| 4,788,201 A | 11/1988 | Kosley, Jr. |
| 4,810,792 A | 3/1989 | Kosley, Jr. |
| 5,091,387 A | 2/1992 | Evans et al. |
| 5,206,240 A | 4/1993 | Baldwin et al. |
| 5,219,860 A | 6/1993 | Chambers et al. |
| 5,457,207 A | 10/1995 | Efange et al. |
| 5,464,788 A | 11/1995 | Bock et al. |
| 5,627,196 A | 5/1997 | Audia et al. |
| 5,633,247 A | 5/1997 | Baldwin et al. |
| 5,670,509 A | 9/1997 | Evans et al. |
| 5,698,567 A | 12/1997 | Guillonneau et al. |
| 5,756,504 A | 5/1998 | Bock et al. |
| 5,849,780 A | 12/1998 | Di Malta et al. |
| 5,885,999 A * | 3/1999 | Elliott et al. ............. 514/266.22 |
| 6,136,839 A | 10/2000 | Isakson et al. |
| 6,166,209 A | 12/2000 | Adam et al. |
| 6,207,677 B1 | 3/2001 | Moltzen et al. |
| 6,262,066 B1 | 7/2001 | Tulshian et al. |
| 6,326,375 B1 | 12/2001 | Fukami et al. |
| 6,388,077 B1 | 5/2002 | Fukami et al. |
| 6,716,846 B2 | 4/2004 | Tulshian et al. |
| 6,828,440 B2 | 12/2004 | Goehring et al. |
| 8,193,208 B2 | 6/2012 | Chen et al. |
| 8,293,900 B2 | 10/2012 | Jian et al. |

(Continued)

FOREIGN PATENT DOCUMENTS

| | | |
|---|---|---|
| DE | 24 58 176 | 6/1975 |
| EP | 0 444 945 A2 | 9/1991 |
| EP | 0 445 974 A2 | 9/1991 |
| EP | 0 581 939 B1 | 6/1999 |
| GB | 1 575 800 | 10/1980 |

(Continued)

OTHER PUBLICATIONS

Abou-Gharbia, M., et al., "Psychotropic Agents: Synthesis and Antipsychotic Activity of Substituted β-Carbolines," *J. Med. Chem.* 30:1100-1105, American Chemical Society (1987).

(Continued)

*Primary Examiner* — Charanjit Aulakh
(74) *Attorney, Agent, or Firm* — Sterne, Kessler, Goldstein & Fox P.L.L.C.

(57) ABSTRACT

The invention relates to fused and spirocycle compounds of Formula I:

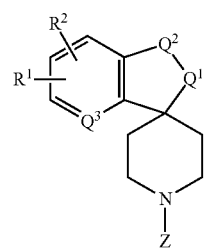

or a pharmaceutically acceptable salt, prodrug, or solvate thereof, wherein $R^1$, $R^2$, $Q^1$-$Q^3$, and Z are defined as set forth in the specification. The invention is also directed to the use of compounds of Formula I to treat, prevent or ameliorate a disorder responsive to the blockade of calcium channels, and particularly N-type calcium channels. Compounds of the present invention are especially useful for treating pain.

13 Claims, No Drawings

(56) References Cited

U.S. PATENT DOCUMENTS

| | | |
|---|---|---|
| 8,546,417 B2 | 10/2013 | Chen et al. |
| 2001/0011092 A1 | 8/2001 | Tulshian et al. |
| 2003/0018041 A1 | 1/2003 | Goehring et al. |
| 2003/0073690 A1 | 4/2003 | Tulshian et al. |
| 2003/0171370 A1 | 9/2003 | Tsushima et al. |
| 2005/0104233 A1 | 5/2005 | Kato et al. |
| 2005/0153998 A1 | 7/2005 | Ito et al. |
| 2006/0035884 A1 | 2/2006 | Neitzel et al. |
| 2006/0079505 A1 | 4/2006 | Makings et al. |

FOREIGN PATENT DOCUMENTS

| | | |
|---|---|---|
| JP | 51-032564 | 3/1976 |
| WO | WO 96/24582 A1 | 8/1996 |
| WO | WO 01/87839 A1 | 11/2001 |
| WO | WO 02/36122 A1 | 5/2002 |
| WO | WO 02/088089 A1 | 11/2002 |
| WO | WO 03/037271 A2 | 5/2003 |
| WO | WO 03/051868 A1 | 6/2003 |
| WO | WO 2004/004714 A1 | 1/2004 |
| WO | WO 2004/005295 A1 | 1/2004 |
| WO | WO 2004/076455 A1 | 9/2004 |
| WO | WO 2005/063745 A2 | 7/2005 |
| WO | WO 2005/085228 A1 | 9/2005 |
| WO | WO 2006/040329 A1 | 4/2006 |
| WO | WO 2006/058303 A2 | 6/2006 |

OTHER PUBLICATIONS

Bignan, G.C., et al., "Preparation of 3-spirocyclic indoline-2-ones as ligands for the ORL-1 receptor," *Bioorg. Med. Chem. Lett.* 15:5022-5026, Elsevier Ltd. (Nov. 2005).

Brower, V., "New paths to pain relief," *Nat. Biotechnol.* 18:387-391, Nature America Publishing (2000).

Castellano, A., et al., "Cloning and Expression of a Neuronal Calcium Channel β Subunit," *J. Biol. Chem.* 268:12359-12366, American Society for Biochemistry and Molecular Biology (1993).

Davila, H.M., "Molecular and Functional Diversity of Voltage-Gated Calcium Channels," *Ann. NY Acad. Sci.* 868:102-117, The New York Academy of Sciences (1999).

Dubel, S.J., et al., "Molecular cloning of the α-1 subunit of an ω-conotoxin-sensitive calcium channel," *Proc. Natl. Acad. Sci. U.S. A.* 89:5058-5062, National Academy of Sciences (1992).

Evans, B.E., et al., "Orally Active, Nonpeptide Oxytocin Antagonists," *J. Med. Chem.* 35:3919-3927, American Chemical Society (1992).

Filer, C.N., "Chapter 6: The Preparation and Characterization if Tritiated Neurichemicals," in *Isotopes in the Physical and Biomedical Sciences*, vol. 1, Labeled Compounds (Part A), Buncel, E. and Jones, J.R., eds., Elsevier, Amsterdam, BE, pp. 156-192 (1987).

Finke, P.E., et al., "Antagonists of the Human CCR5 Receptor as Anti-HIV-1 Agents, Part 3: A Proposed Pharmacophore Model for 1-[N-(Methyl)-N-(phenylsulfonyl)amino]-2-(phenyl)-4-[4-(substituted)piperidin-1-yl]butanes," *Bioorg. Med. Chem. Lett.* 11:2469-2473, Elsevier Sciences Ltd. (2001).

Goehring, R.R., "Synthesis of a Spirocyclic Oxindole Analogue as a Putative Replacement for $Pro^2-Pro^3-Gly^4-Phe^5$ in Bradykinin Antagonists," *Org. Prep. Proced. Int.* 27:691-694, Organic Preparations and Procedures, Inc. (1995).

Gould, R.J., et al., "Antischizophrenic drugs of the diphenylbutylpiperidine type act as calcium channel antagonists," *Proc. Natl. Acad. Sci. USA* 80:5122-5125, National Academy of Sciences (1983).

Hamill, O.P., et al., "Improved Patch-Clamp Techniques for High-Resolution Current Recording from Cells and Cell-Free Membrane Patches," *Pflügers Arch.* 391:85-100, Springer-Verlag (1981).

Hanson, G.R., "Chapter 72. Analgesic, Antipyretic and Anti-inflammatory Drugs," in *Remington: The Science and Practice of Pharmacy*, vol. II, Mack Printing Company, Easton, PA, pp. 1196-1221 (1995).

Hu, L-Y., et al., "Structure-Activity Relationship of N-Methyl-N-Aralkyl-Peptidylamines as Novel N-Type Calcium Channel Blockers," *Bioorg. Med. Chem. Lett.* 9:2151-2156, Elsevier Science Ltd. (1999).

Hu, L-Y., et al., "Synthesis of a Series of 4-Benzyloxyaniline Analogues as Neuronal N-Type Calcium Channel Blockers with Improved Anticonvulsant and Analgesic Properties," *J. Med. Chem.* 42:4239-4249, American Chemical Society (1999).

Hu, L-Y., et al., "The Discovery of [1-(4-Dimethylamino-benzyl)-piperidin-4-yl]-[4-(3,3-dimethylbutyl)-phenyl]-(3-methyl-but-2-enyl)-Amine, an N-type $Ca^{+2}$ Channel Blocker with Oral Activity for Analgesia," *Bioorg. Med. Chem.* 8:1203-1212, Elsevier Science (2000).

Hunskaar, S., et al., "Formalin test in mice, a useful technique for evaluating mild analgesics," *J. Neurosci. Meth.* 14:69-76, Elsevier Publishers B.V. (1985)

Insel, P.A., "Chapter 27. Analgesic-Antipyretic and Antiinflammatory Agents and Drugs Employed in the Treatment of Gout," in *Goodman & Gilman's The Pharmacological Basis of Therapeutics*, $9^{th}$ Ed., Molinhoff, P.B. and Ruddon, R.W., eds., McGraw-Hill, New York, NY, pp. 617-657 (1996).

Ito, M., "Long-Term Depression," *Annu. Rev. Neurosci.* 12:85-102, Annual Reviews, Inc. (1989).

Janis, R.J. and Triggle, D.J., "Chapter 13. Drugs Acting on Calcium Channels," in *Calcium Channels: Their Properties, Functions, Regulation and Clinical Relevance*, Hurwitz, L., et al., eds., CRC Press, London, England, pp. 195-249 (1991).

Kim, S.H., and Chung, J.M., "An experimental model for peripheral neuropathy produced by segmental spinal nerve ligation in the rat," *Pain* 50:355-363, Elsevier Science Publishers B.V. (1992).

Kim, H-L., et al., "Rat brain expresses an alternatively spliced form of the dihyropyridine-sensitive L-type calcium channel α2 subunit," *Proc. Natl. Acad. Sci. U.S.A.* 89:3251-3255, National Academy of Sciences (1992).

Koch, W.J., et al., "cDNA Cloning of a Dihydropyridine-sensitive Calcium Channel from Rat Aorta. Evidence for the Existence of Alternatively Spliced Forms," *J. Biol. Chem.* 265:17786-17791, The American Society for Biochemistry and Molecular Biology, Inc. (1990).

Levine, J., and Taiwo, Y., "Chapter 2, Inflammatory Pain," in *Textbook of Pain*, $3^{rd}$ Ed., Wall, P.D. and Melzack, R., eds., Churchill Livingstone, Edinburgh, England, pp. 45-56 (1994).

Lin, Z., et al., "Identification of Functionally Distinct Isoforms of the N-Type $Ca^{2+}$ Channel in Rat Sympathetic Ganglia and Brain," *Neuron* 18:153-166, Cell Press (1997).

Lukyanetz, E.A., "Selective Blockade of N-Type Calcium Channels by Levetiracetam," *Epilepsia* 43:9-18, Blackwell Publishing (2002).

Maier, C.A., and Wünsch, B., "Novel Spiropiperidines as Highly Potent and Subtype Selective σ-Receptor Ligands. Part 1," *J. Med. Chem.* 45:438-448, American Chemical Society (2002).

Maier, C.A., and Wünsch, B., "Novel σ-Receptor Ligands. Part 2. SAR of Spiro[[2]benzopyran-1,4'-piperadines] and Spiro[[2]benzofuran-1,4'-piperadines] with Carbon Substituents in Position 3," *J. Med. Chem.* 45:4923-4930, American Chemical Society (2002).

Maligres, P.E., et al., "Synthesis of the Orally Active Spiroindoline-Based Growth Hormone Secretagogue, MK-677," *Tetrahedron* 53:10983-10992, Pergamon Press (1997).

Marxer, A., et al., "Spiro Piperadines. I. Synthesis of Spiro[isobenzofuran-1(3H),4'-piperadines] and Spiro[isobenzofuran-1(3H),3'-piperadines]," *J. Org. Chem.* 40:1427-1433, American Chemical Society (1975).

Moltzen, E.K., et al., "σ Ligands with Subnanomolar Affinity and Preference for the $σ_2$ Binding Site. 2. Spiro-Joined Benzofuran, Isobenzofuran, and Benzopyran Piperadines," *J. Med. Chem.* 38:2009-2017, American Chemical Society (1995).

Nuglisch, J., et al., "Protective Effect of Nimodipine Against Ischemic Neuronal Damage in Rat Hippocampus Without Changing Postischemic Cerebral Blood Flow," *J. Cereb. Blood Flow Metab.* 10:654-659, Nature Publishing Group (1990).

(56) References Cited

OTHER PUBLICATIONS

Parham, W.E., et al., "Spiro Piperidines. 1. Synthesis of Spiro[isobenzofuran-1(3H),4'-piperidin]-3-ones, Spiro[isobenzofuran-1(3H),4'-piperadines], and Spiro[isobenzotetrahydrothiophene-1(3H),4'-piperadines]," *J. Org. Chem.* 41:2628-2633, American Chemical Society (1976).

Pragnell, M., et al., "Cloning and tissue-specific expression of the brain calcium channel β-subunit," *FEBS Lett.* 291:253-258, Elsevier Science Ltd. (1991).

Sánchez, I., et al., "Synthesis of new piperidine and cyclohexylamino-spiro derivatives as potential anticalcium agents," *Sci. Pharm.* 70:177-187, Österreichische Apotheker-Verlagsgesellschaft m.b.H. (2002).

Schwartz, A., et al., "Receptors for Calcium Antagonists," *Am. J. Cardiol.* 62:3G-6G, Excerpta Medica (1988).

Siegmund, E., et al., "A Method for Evaluating both Non-Narcotic and Narcotic Analgesics. (23345)," *Proc. Soc. Exp. Biol. Med.* 95:729-731, Thomas J. Griffiths Sons, Inc. (1957).

Šindelář, K., et al., "Neurotropic and Psychotropic Agents. LXVII. 1-[4,4-Bis(4-Fluorophenyl)Butyl]-4-Hydroxy-4-(3-Trifluoro-Methyl-4-Chlorophenyl)Piperidine and Related Compounds: New Synthetic Approaches," *Collection Czechoslov. Chem. Commun.* 38:3879-3901, Nakladatelstvi Ceskoslovenski Akademie Ved (1973).

Song, Y., et al., "(S)-4-Methyl-2-(methylamino)pentanoic Acid [4,4-Bis(4-fluorophenyl)butyl]amide Hydrochloride, a Novel Calcium Channel Antagonist, Is Efficacious in Several Animal Models of Pain," *J. Med. Chem.* 43:3474-3477, American Chemical Society (2000).

Sulsky, R., et al., "Conformational Switching and the Synthesis of Spiro[2H-indol]-3(1H)-ones by Radical Cyclization," *J. Org. Chem.* 64:5504-5510, American Chemical Society (1999).

Vanegas, H., and Schaible, H-G., "Effects of antagonists to high-threshold calcium channels upon spinal mechanisms of pain, hyperalgesia and allodynia," *Pain* 85:9-18, Elsevier Science B.V. (2000).

Wallace, M.S., "Calcium and Sodium Channel Antagonists for the Treatment of Pain," *Clin. J. Pain* 16:S80-S85, Lippincott Williams & Wilkins, Inc. (2000).

Zenchoff, G.S., et al., "The Synthesis of Indazoles via 2,3-Dihydroindazoles (1)," *J. Heterocyclic Chem.* 13:33-39, Journal of Heterocyclic Chemistry (1976).

CAPLUS Databse, Accession No. 1977:89608, English language abstract of Czech Republic Patent No. 160865 B (1977).

CAPLUS Database, Accession No. 1977:43572, English language abstract of Japanese Patent No. 51-032564 (1977).

Dialog File 351, Accession No. 854054, WPI English language abstract for German Patent No. DE 24 58 176 accessed Jun. 28, 2008.

Dialog File 351, Accession No. 6454513, WPI English language abstract for European Patent No. 0 581 939 B1 accessed Jun. 30, 2008.

International Preliminary Report on Patentability for International Application No. PCT/EP2006/008788, mailed Mar. 20, 2008, The International Bureau of WIPO, Geneva, Switzerland.

International Search Report for International Application No. PCT/EP2006/008788, mailed Jan. 31, 2007, European Patent Office, The Netherlands.

Office Action mailed Oct. 5, 2011, in U.S. Appl. No. 11/991,626, Chen et al., having a 35 U.S.C. 371(c) date of Nov. 4, 2008.

Notice of Allowance mailed Jan. 20, 2012, in U.S. Appl. No. 11/991,626, Chen et al., having a 35 U.S.C. 371(c) dated of Nov. 4, 2008.

Office Action mailed on Jan. 11, 2013, in U.S. Appl. No. 13/486,267, Chen et al., filed Jun. 1, 2012.

Notice of Allowance mailed Apr. 25, 2013, in U.S. Appl. No. 13/486,267, Chen et al., filed Jun. 1, 2012.

\* cited by examiner

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
caccatggtc cgcttcgggg ac                                              22

<210> SEQ ID NO 2
<211> LENGTH: 19
<212> TYPE: DNA
<213> ORGANISM: Artificial Sequence
<220> FEATURE:
<223> OTHER INFORMATION: Synthetic Primer

<400> SEQUENCE: 2
ccgttcagtg gcctcctcc                                                  19

<210> SEQ ID NO 3
<211> LENGTH: 23
<212> TYPE: DNA
<213> ORGANISM: Artificial Sequence
<220> FEATURE:
<223> OTHER INFORMATION: Synthetic Primer

<400> SEQUENCE: 3
ctagcaccag tgatcctggt ctg                                             23

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
agtgcgttgt gagcgcagta                                                 20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
caccatggtc cagaagagcg g                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
tctcagcgga tgtagacgcc t                                               21

<210> SEQ ID NO 7
<211> LENGTH: 22
<212> TYPE: DNA
<213> ORGANISM: Artificial Sequence

```
<220> FEATURE:
<223> OTHER INFORMATION: Synthetic Primer

<400> SEQUENCE: 7
caccatgtat gacgactcct ac                                              22

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
ggtggtcagt agctgtcctt agg                                             23

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
caccatggct gctggctgcc t                                               21

<210> SEQ ID NO 10
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
agagggtcac catagatagt gtctg                                           25

<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
caccatgatt cgggccttcg ct                                              22

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
agcctgcgga ctacaggttg ctgac                                           25
```

FUSED AND SPIROCYCLE COMPOUNDS AND THE USE THEREOF

REFERENCE TO SEQUENCE LISTING SUBMITTED ELECTRONICALLY

The content of the electronically submitted Sequence Listing (Name: 1861_1780004_SequenceListing_ascii.txt; Size: 2,816 bytes; and Date of Creation: Sep. 10, 2013) filed herewith is incorporated herein by reference in its entirety.

BACKGROUND OF THE INVENTION

1. Field of the Invention

This invention is in the field of medicinal chemistry. The invention relates to novel fused and spirocycle compounds and the use of these compounds as blockers of calcium ($Ca^{2+}$) channels.

2. Background Art

Calcium ions play fundamental roles in the regulation of many cellular processes. It is therefore essential that their intracellular levels be maintained under strict, yet dynamic control (Davila, H. M., *Annals of the New York Academy of Sciences*, pp. 102-117 (1999)). Voltage-gated calcium channels (VGCC) serve as one of the important mechanisms for fast calcium influx into the cell. Calcium channels are hetero-oligomeric proteins consisting of a pore-forming subunit (α1), which is able to form functional channels on its own in heterologous expression systems, and a set of auxiliary or regulatory subunits. Calcium channels have been classified based on their pharmacological and/or electrophysiological properties. The classification of voltage-gated calcium channels divides them into three groups: (i) high voltage-activated (HVA) channels, which include L-, N-, P-, and Q-types; (ii) intermediate (IVA) voltage-activated R-type channels; and (iii) low voltage-activated (LVA) T-type channels (Davila, supra). Voltage-gated calcium channels (VGCC) are also known as voltage-dependent calcium channels (VDCC) or voltage-sensitive calcium channels (VSCC).

Voltage-sensitive calcium channels (VSCC) regulate intracellular calcium concentration, which affects various important neuronal functions such as cellular excitability, neurotransmitter release, hormone secretion, intracellular metabolism, neurosecretory activity and gene expression (Hu et al., *Bioorganic & Medicinal Chemistry* 8:1203-1212 (2000)). N-type channels are found mainly in central and peripheral neurons, being primarily located on presynaptic nerve terminals. These channels regulate the calcium flux required for depolarization-evoked release of a transmitter from synaptic endings. The transmission of pain signals from the periphery to the central nervous system (CNS) is mediated by N-type calcium channels located in the spinal cord (Song et al., *J. Med. Chem.* 43:3474-3477 (2000)).

The six types of calcium channels (i.e., L, N, P, Q, R, and T) are expressed throughout the nervous system (Wallace, M. S., *The Clinical Journal of Pain* 16:580-585 (2000)). Voltage-sensitive calcium channels of the N-type exist in the superficial laminae of the dorsal horn and are thought to modulate nociceptive processing by a central mechanism. Blockade of the N-type calcium channel in the superficial dorsal horn modulates membrane excitability and inhibits neurotransmitter release, resulting in pain relief. Wallace (supra) suggests that based on animal models, N-type calcium channel antagonists have a greater analgesic potency than sodium channel antagonists.

N-type calcium channel blockers have usefulness for neuroprotection and analgesia. Ziconotide, which is a selective N-type calcium channel blocker, has been found to have analgesic activity in animal models and neuroprotective activity in focal and global ischemia models (Song et al., supra). Examples of known calcium channel blockers include flunarizine, fluspirilene, cilnipide, PD 157767, SB-201823, SB-206284, NNC09-0026, and PD 151307 (Hu et al., supra).

Blockade of N-type channels can prevent and/or attenuate subjective pain as well as primary and/or secondary hyperalgesia and allodynia in a variety of experimental and clinical conditions (Vanegas, H. et al., *Pain* 85:9-18 (2000)). N-type voltage-gated calcium channels (VGCC) play a major role in the release of synaptic mediators such as glutamate, acetylcholine, dopamine, norepinephrine, gamma-aminobutyric acid (GABA) and calcitonin gene-related peptide (CGRP).

Inhibition of voltage-gated L-type calcium channels has been shown to be beneficial for neuroprotection (Song et al., supra). However, inhibition of cardiac L-type calcium channels can lead to hypotension. It is believed that a rapid and profound lowering of arterial pressure tends to counteract the neuroprotective effects of L-type calcium channel blockers. A need exists for antagonists that are selective for N-type calcium channels over L-type calcium channels to avoid potential hypotensive effects.

U.S. Pat. No. 3,962,259 to Bauer et al. describes 1,3-dihydrospiro[isobenzofuran]s that are described to be useful as tranquilizers and analgetics.

U.S. Pat. No. 3,686,186 to Houlihan et al. describes substituted isochroman or phthalan piperidines that are described to be useful as hypotriglyceridemic, antihypertensive and antidepressant agents.

U.S. Pat. No. 6,828,440 B2 to Goehring et al. describes spiroindene and spiroindane compounds that are described to exhibit affinity for the ORL1 receptor.

U.S. Pat. No. 5,219,860 to Chambers et al. describes spirocyclic compounds that are described to be useful as neuroleptic agents.

U.S. Pat. No. 5,670,509 to Evans et al. describes spiroindane and spiroindene compounds useful as oxytocin receptor antagonists.

U.S. Patent Application Publication No. US 2006/0035884 A1 by Neitzel et al. describes 1'-[(4-chlorophenyl)sulfonyl]spiro[indene-1,4'-piperidine] that is described to be useful for treating cognitive disorders, including Alzheimer's disease.

Published European Patent Application No. 0 444 945 A2 describes spiroindane and spiroindene compounds that are described to be useful in the treatment and prevention of oxytocin-related disorders.

International Publication No. WO 2006/040329 A1 describes, inter alia, spiroindene and spiroindane compounds that are described to inhibit the activity of 11βHSDI.

U.S. Pat. No. 3,959,475 to Bauer et al. describes substituted 1,3-dihydrospiro(isobenzofuran)s that are described to be useful as antidepressants, tranquilizers and analgetic agents.

U.S. Pat. No. 6,116,209 to Adam et al. describes piperidine derivatives that are described to be OFQ receptor antagonists.

U.S. Pat. No. 4,233,307 and British Patent Specification No. 1575800 both to Ono et al. describe spiro amine derivatives that are described as having antihypertensive and central nervous system depressant activity.

BRIEF SUMMARY OF THE INVENTION

The present invention is related to the use of compounds represented by Formula I, below, and the pharmaceutically acceptable salts, prodrugs and solvates thereof, as blockers of calcium ($Ca^{2+}$) channels. Certain compounds of Formula I show selectivity as N-type calcium channel blockers.

The invention is also related to treating, preventing or ameliorating a disorder responsive to the blockade of calcium channels in a mammal suffering from excess activity of said channels by administering an effective amount of a compound of Formula I, or a pharmaceutically acceptable salt, prodrug or solvate thereof, as described herein. Specifically, the invention is related to treating, preventing or ameliorating a disorder responsive to the blockade of N-type calcium channels in a mammal suffering from excess activity of said channels by administering an effective amount of a compound of Formula I, or a pharmaceutically acceptable salt, prodrug or solvate thereof, as described herein.

A number of compounds useful in the present invention have not been heretofore reported. Thus, one aspect of the present invention is directed to novel compounds of Formula I, as well as their pharmaceutically acceptable salts, prodrugs and solvates.

Another aspect of the present invention is directed to the use of the novel compounds of Formula I, and their pharmaceutically acceptable salts, prodrugs and solvates, as blockers of N-type calcium channels.

A further aspect of the present invention is to provide a method for treating preventing or ameliorating stroke, neuronal damage resulting from head trauma, epilepsy, pain (e.g., acute pain, chronic pain, which includes, but is not limited to, neuropathic pain and inflammatory pain, or surgical pain), migraine, a mood disorder, schizophrenia, a neurodegenerative disorder (e.g., Alzheimers disease, amyotrophic lateral sclerosis (ALS), or Parkinson's disease), depression, anxiety, a psychosis, hypertension, or cardiac arrhythmia, by administering an effective amount of a compound of Formula I, or a pharmaceutically acceptable salt, prodrug or solvate thereof, to a mammal in need of such treatment, prevention or amelioration.

A further aspect of the present invention is to provide a pharmaceutical composition useful for treating, preventing or ameliorating a disorder responsive to the blockade of calcium ion channels, especially N-type calcium ion channels, said pharmaceutical composition containing an effective amount of a compound of Formula I, or a pharmaceutically acceptable salt, prodrug or solvate thereof, in a mixture with one or more pharmaceutically acceptable carriers.

Also, an aspect of the present invention is to provide a method of modulating calcium channels, especially N-type calcium channels, in a mammal, wherein said method comprises administering to the mammal an effective amount of at least one compound of Formula I, or a pharmaceutically acceptable salt, prodrug or solvate thereof.

A further aspect of the present invention is to provide radiolabeled compounds of Formula I and the use of such compounds, or their pharmaceutically acceptable salts, prodrugs or solvates, as radioligands for their binding site on the calcium channel.

A further aspect of the invention is to provide a method for screening a candidate compound for the ability to bind to a receptor using a radiolabeled compound of Formula I, which includes, but is not limited to, a $^3H$, $^{11}C$ and $^{14}C$ radiolabeled compound of Formula I, or a pharmaceutically acceptable salt, prodrug or solvate thereof. This method comprises a) introducing a fixed concentration of the radiolabeled compound to the receptor to form a mixture; b) titrating the mixture with a candidate compound; and c) determining the binding of the candidate compound to said receptor.

A further aspect of the invention is to provide the use of a compound of Formula I, or a pharmaceutically acceptable salt, prodrug or solvate thereof, in the manufacture of a medicament for treating, preventing or ameliorating stroke, neuronal damage resulting from head trauma, epilepsy, pain, migraine, a mood disorder, schizophrenia, a neurodegenerative disorder, depression, anxiety, a psychosis, hypertension, or cardiac arrhythmia in a mammal. In a preferred embodiment, the invention provides the use of a compound of Formula I, or a pharmaceutically acceptable salt, prodrug or solvate thereof, in the manufacture of a medicament for treating, preventing or ameliorating acute pain, chronic pain, or surgical pain.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention, as claimed.

DETAILED DESCRIPTION OF THE INVENTION

One aspect of the present invention is based on the use of compounds of Formula I, and the pharmaceutically acceptable salts, prodrugs and solvates thereof, as blockers of $Ca^{2+}$ channels. In view of this property, compounds of Formula I, and the pharmaceutically acceptable salts, prodrugs and solvates thereof, are useful for treating disorders responsive to the blockade of calcium ion channels. In one aspect, it has been found that certain compounds of Formula I, and the pharmaceutically acceptable salts, prodrugs and solvates thereof, selectively block N-type calcium ion channels and, thus, are useful for treating disorders responsive to the selective blockade of N-type calcium ion channels.

The compounds useful in this aspect of the invention are compounds represented by Formula I:

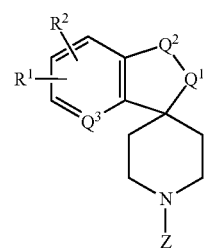

I or a pharmaceutically acceptable salt, prodrug or solvate thereof, wherein:

$R^1$ and $R^2$ are each independently selected from the group consisting of hydrogen, alkyl, alkoxy, halogen, and —C(O)Y, wherein Y is hydroxy, alkoxy, amino, alkylamino, or dialkylamino;

$Q^1$ is O, —C(O)—, $CR^{20}R$, or N—R;

$Q^2$ is —C(O)—, $CR^{21}R^{22}$, or N—$R^{26}$; and $Q^3$ is $CR^{23}$ or N; provided that when $Q^3$ is N, then $Q^1$ is $CR^{20}R^{24}$ and $Q^2$ is $CR^{21}R^{22}$;

when $Q^1$ is O or $CR^{20}R^{24}$, then $Q^2$ is —C(O)— or $CR^{21}R^{22}$, and $Q^3$ is $CR^{23}$;

when $Q^1$ is N—$R^{25}$, then $Q^2$ is —C(O)— and $Q^3$ is $CR^{22}$; and when $Q^2$ is N—$R^{26}$, then $Q^1$ is —C(O)— and $Q^3$ is $CR^{23}$;

$R^{20}$, $R^{21}$, $R^{22}$, and $R^{24}$ are each independently selected from the group consisting of hydrogen and alkyl; or $R^{20}$ and $R^{21}$ together form a bond and $R^{22}$ and $R^{24}$ are independently hydrogen or alkyl;

$R^{23}$ is hydrogen or alkyl;

$R^{25}$ and $R^{26}$ are independently selected from the group consisting of hydrogen, alkyl, hydroxyalkyl, alkoxyalkyl, haloalkyl, cycloalkyl, phenyl, benzyl, and phenethyl, wherein the phenyl ring of any of the phenyl, benzyl and phenethyl groups is optionally substituted with one or two substituents independently selected from the group consisting of alkyl, alkoxy, halogen, and haloalkyl;

Z is selected from the group consisting of $Z^1$, $Z^2$, $Z^3$, $Z^4$, and $Z^5$, wherein:

$Z^1$ is

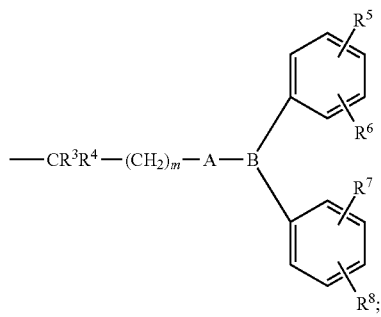

$Z^2$ is

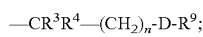

$Z^3$ is

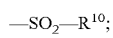

$Z^4$ is

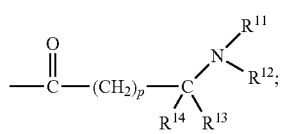

and $Z^5$ is

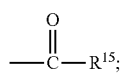

$R^3$ and $R^4$ are both hydrogen or together form =O;

$R^5$, $R^6$, $R^7$ and $R^8$ are each independently selected from the group consisting of hydrogen, alkyl, alkoxy, halogen, haloalkyl, haloalkoxy, hydroxy, hydroxyalkyl, cyano, amino, aminoalkyl, alkylamino, and dialkylamino;

$R^9$ is selected from the group consisting of phenyl optionally substituted with one or two substituents independently selected from the group consisting of alkyl, alkoxy, halogen, haloalkyl, haloalkoxy, hydroxy, hydroxyalkyl, cyano, amino, aminoalkyl, alkylamino, and dialkylamino, or two substituents in adjacent carbon atoms in the phenyl ring optionally form a bridge —O—$CH_2$—O—; and pyridyl optionally substituted with one or two substituents independently selected from the group consisting of alkyl, haloalkyl, halogen, haloalkoxy, and alkoxy; or -D-$R^9$ together forms

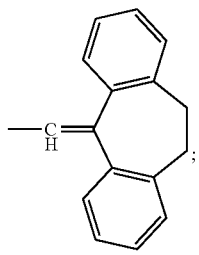 [SMILES: CC=C1c2ccccc2CCc2ccccc21]

$R^{10}$ is phenyl optionally substituted with one or two substituents independently selected from the group consisting of alkyl, alkoxy, halogen, haloalkyl, haloalkoxy, amino, alkylamino, dialkylamino, and alkylcarbonylamino; or 1,2,3,4-tetrahydroquinolinyl or 1,2,3,4-tetrahydroisoquinolinyl optionally substituted at the nitrogen atom with alkylcarbonyl or haloalkylcarbonyl;

$R^{11}$ and $R^{12}$ are each independently selected from the group consisting of hydrogen, alkyl, alkenyl, alkoxycarbonyl, hydroxyalkyl, haloalkyl, mercaptoalkyl, aminoalkyl;

phenyl optionally substituted with one or two substituents independently selected from the group consisting of alkyl, alkoxy, halogen, and haloalkyl; and benzyl, wherein the phenyl ring is optionally substituted with one or two substituents independently selected from the group consisting of alkyl, alkoxy, halogen, and haloalkyl;

$R^{13}$ is hydrogen and $R^{14}$ is selected from the group consisting of hydrogen, alkyl, hydroxyalkyl, alkoxyalkyl, haloalkyl, and aminoalkyl;

$R^{15}$ is selected from the group consisting of alkylthioalkyl, 2-benzo[b]thienyl, 3-benzo[b]thienyl, 1-benzo[c]thienyl, 3-benzo[c]thienyl, 2-benzofuryl, 3-benzofuryl, 1-isobenzofuryl, 3-isobenzofuryl, 4-morpholinyl, 4-thiomorpholinyl, 1-piperazinyl, 1-piperidinyl, and 1-pyrrolidinyl;

A is —C(O)—, $CH_2$, or is absent, and B is CH or N; or A-B is CH—C (where CH is attached to —$(CH_2)_m$—);

D is —C(O)— or is absent;

m is 0, 1, 2, 3, 4, or 5;

n is 0, 1, 2, or 3; and p is 0 or 1.

The groups $R^1$, $R^2$ and $R^5$-$R^8$, when they are not equal to H, each take the place of a hydrogen atom that would otherwise be present in any position on the aryl or heteroaryl ring to which the R group is attached. Similarly, the optional substituents attached to the phenyl and pyridyl rings as defined for $R^9$, and to the phenyl ring as defined for $R^{10}$, $R^{11}$, $R^{12}$, $R^{25}$ and $R^{26}$ each take the place of a hydrogen atom that would otherwise be present in any position on the phenyl or pyridyl rings.

One group of compounds useful in this aspect of the present invention are compounds of Formula I as defined above, with the following provisos when $Q^3$ is $CR^{23}$:

1) when $Q^1$ is O, $Q^2$ is —C(O)—, Z is $Z^1$, and B is CH, then $R^3$ and $R^4$ together form =O or A is —C(O)—;

2) when $Q^1$ is O, $Q^2$ is —C(O)—, Z is $Z^2$, and $R^9$ is optionally substituted phenyl, then $R^1$ and $R^4$ together form =O and D is —C(O)— when n is 1, 2, or 3 or D is absent when n is 0;

3) when $Q^1$ is $CR^{20}R^{24}$ and $Q^2$ is $CR^{21}R^{22}$ or —C(O)—, or $Q^1$ is $CR^{20}R^{24}$ or —C(O)— and $Q^2$ is $CR^{21}R^{22}$, Z is $Z^1$, A is $CH_2$ or absent, and B is CH, then $R^3$ and $R^4$ together form =O;

4) when $Q^1$ is $CR^{20}R^{24}$ and $Q^2$ is $CR^{21}R^{22}$ or —C(O)—, or $Q^1$ is $CR^{20}R^{24}$ or —C(O)— and $Q^2$ is $CR^{21}R^{22}$, Z is $Z^2$, n is 0 or 1, and D is absent, then $R^9$ is not an optionally substituted phenyl;

5) when $Q^1$ is $CR^{20}R^{24}$, $Q^2$ is $CR^{21}R^{22}$, and Z is $Z^3$, then $R^{10}$ is not an optionally substituted phenyl;

6) when $Q^1$ is O, $Q^2$ is $CR^{21}R^{22}$, Z is $Z^1$, B is CH, and A is $CH_2$ or absent, then $R^3$ and $R^4$ together form =O;

7) when $Q^1$ is O, $Q^2$ is $CR^{21}R^{22}$, Z is $Z^1$, B is CH and $R^3$ and $R^4$ are both hydrogen, then A is —C(O)—;

8) when $Q^1$ is O, $Q^2$ is $CR^{21}R^{22}$, Z is $Z^2$, and $R^9$ is optionally substituted phenyl, then $R^3$ and $R^4$ together form =O;

9) when $Q^1$ is O and $Q^2$ is $CR^{21}R^{22}$ or —C(O)—, or $Q^1$ is $CR^2R^2$ and $Q^2$ is $CR^{21}R^{22}$, where $R^{20}$ and $R^{21}$ together form a bond, and Z is $Z^2$, then -D-$R^9$ does not together form

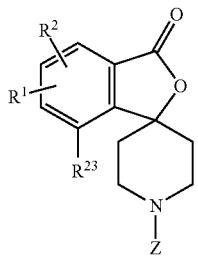

or 10) when $Q^1$ is —C(O)—, $Q^2$ is N—$R^{26}$, and Z is $Z^2$, then $R^1$ and $R^4$ together form =O.

In one embodiment, compounds useful in this aspect of the present invention are compounds of Formula I where $Q^1$-$Q^3$, $Z^1$-$Z^5$, $R^1$-$R^{15}$, $R^{20}$-$R^{23}$, A, B, D, Y, m, n, and p are as described above, with the provisos that when $Q^1$ is O, $Q^2$ is —C(O)—, and $Q^3$ is CH, and 1) Z is $Z^1$ and B is CH, then $R^3$ and $R^4$ together form =O or A is —C(O)—; or 2) Z is $Z^2$, then $R^3$ and $R^4$ together form =O and D is —C(O)—, or $R^3$ and $R^4$ together form =O, D is absent and n is 0;

or a pharmaceutically acceptable salt, prodrug or solvate thereof.

In one embodiment, compounds useful in the present invention are compounds of Formula I where $Q^1$ is O or $CHR^{20}$ (i.e., $CR^{20}R^{24}$, where $R^{24}$ is hydrogen); $Q^2$ is —C(O)— or $CR^{21}R^{22}$; and $Q^3$ is $CR^{23}$ or N; provided that when $Q^1$ is O, then $Q^2$ is —C(O)— and $Q^3$ is $CR^{23}$, wherein $R^{23}$ is hydrogen or alkyl; and when $Q^1$ is $CHR^{20}$, then $Q^2$ is $CR^{21}R^{22}$ and $Q^3$ is N, wherein $R^{20}$ and $R^{21}$ together form a bond, and $R^{22}$ is hydrogen or alkyl; or a pharmaceutically acceptable salt, prodrug or solvate thereof.

In compounds of Formula I where Z is $Z^4$, the carbon to which the —$NR^{11}R^{12}$ group is attached can be a chiral center. Accordingly, the configuration at that carbon atom can be (R) or (S), with (S) being preferred.

In one embodiment, compounds useful in the present invention are compounds of Formula I where $Q^1$ is O, $Q^2$ is —C(O)—, and $Q^3$ is $CR^{23}$, i.e, compounds of Formula II:

II wherein $R^1$, $R^2$, $R^{23}$, and Z are as defined above, and pharmaceutically acceptable salts, prodrugs and solvates thereof.

In a further embodiment, compounds useful in the present invention are compounds of Formula I where $Q^1$ is $CR^{20}R^{24}$, $Q^2$ is $CR^{21}R^{22}$, $Q^3$ is N, and $R^{20}$ and $R^{21}$ together form a bond, i.e, compounds of Formula III:

III wherein $R^1$, $R^2$, $R^{22}$, $R^{24}$ and Z are as defined above, and pharmaceutically acceptable salts, prodrugs and solvates thereof. Advantageously, $R^{22}$ and $R^{24}$ are both hydrogen. Useful compounds of Formula III include those where $R^{22}$ and $R^{24}$ are independently hydrogen or $C_{1-4}$ alkyl, preferably hydrogen, methyl or ethyl. Preferably, either $R^{22}$ or $R^{24}$ is hydrogen and the other one is hydrogen or methyl, and more preferably $R^{22}$ and $R^{24}$ are both hydrogen.

In a further embodiment, compounds useful in the present invention are compounds of Formula I where $Q^1$ is $CR^{20}R^{24}$, $Q^2$ is $CR^{21}R^{22}$, $Q^3$ is N, and $R^{20}$, $R^{21}$, $R^{22}$, and $R^{24}$ are each independently hydrogen or alkyl, i.e, compounds of Formula IV:

IV wherein $R^1$, $R^2$, and Z are as defined above, and pharmaceutically acceptable salts, prodrugs and solvates thereof. Useful compounds of Formula IV include those where $R^{20}$, $R^{21}$, $R^{22}$, and $R^{24}$ are each independently hydrogen or $C_{1-4}$ alkyl, preferably hydrogen, methyl or ethyl. Preferably, $R^{20}$ and $R^{21}$ are both hydrogen and $R^{22}$ and $R^{24}$ are independently hydrogen, methyl or ethyl, more preferably hydrogen or methyl. More preferably $R^{20}$, $R^{21}$, $R^{22}$, and $R^{24}$ are each hydrogen.

In a further embodiment, compounds useful in the present invention are compounds of Formula I where $Q^1$ is $CR^{20}R^{24}$, $Q^2$ is $CR^{21}R^{22}$, $Q^3$ is $CR^{23}$, and $R^{20}$, $R^{21}$, $R^{22}$, $R^{23}$ and $R^{24}$ are each independently hydrogen or alkyl, i.e, compounds of Formula V:

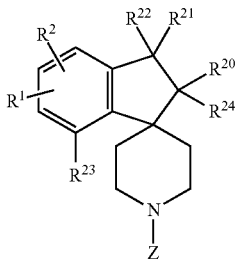

V wherein $R^1$, $R^2$, $R^{23}$, and Z are as defined above, and pharmaceutically acceptable salts, prodrugs and solvates thereof. Useful compounds of Formula V include those where $R^{20}$, $R^{21}$, $R^{22}$, and $R^{24}$ are each independently hydrogen or $C_{1-4}$ alkyl, preferably hydrogen, methyl or ethyl. Preferably, $R^{20}$ and $R^{21}$ are both hydrogen and $R^{22}$ and $R^{24}$ are independently hydrogen, methyl or ethyl, more preferably hydrogen or methyl. More preferably $R^{20}$, $R^{21}$, $R^{22}$, and $R^{24}$ are each hydrogen.

In a further embodiment, compounds useful in the present invention are compounds of Formula I where $Q^1$ is $CR^{20}R^{24}$, $Q^2$ is $CR^{21}R^{22}$, $Q^3$ is $CR^{23}$, $R^{20}$ and $R^{21}$ together form a bond, i.e, compounds of Formula VI:

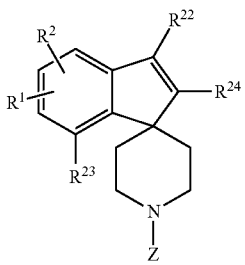

VI wherein $R^1$, $R^2$, $R^{22}$, $R^{23}$, $R^{13}$, and Z are as defined above, and pharmaceutically acceptable salts, prodrugs and solvates thereof. Useful compounds of Formula VI include those where $R^{22}$ and $R^{24}$ are independently hydrogen or $C_{1-4}$ alkyl, preferably hydrogen, methyl or ethyl. Preferably, either $R^{22}$ or $R^{24}$ is hydrogen and the other one is hydrogen or methyl, and more preferably $R^{22}$ and $R^{24}$ are both hydrogen.

In a further embodiment, compounds useful in the present invention are compounds of Formula I where $Q^1$ is O, $Q^2$ is $CR^{21}R^{22}$, and $Q^3$ is $CR^{23}$, i.e, compounds of Formula VII:

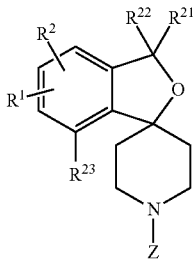

VII wherein $R^1$, $R^2$, $R^{22}$, $R^{21}$, and Z are as defined above, and pharmaceutically acceptable salts, prodrugs and solvates thereof. Useful compounds of Formula VII include those where $R^{21}$ and $R^{22}$ are independently hydrogen or $C_{1-4}$ alkyl, preferably hydrogen, methyl or ethyl. Preferably, $R^{21}$ is hydrogen and $R^{22}$ is hydrogen or methyl, and more preferably $R^{21}$ and $R^{22}$ are both hydrogen.

In a further embodiment, compounds useful in the present invention are compounds of Formula I where $Q^1$ is $N-R^{25}$, $Q^2$ is $-C(O)-$, and $Q^3$ is $CR^{23}$, i.e, compounds of Formula VIII:

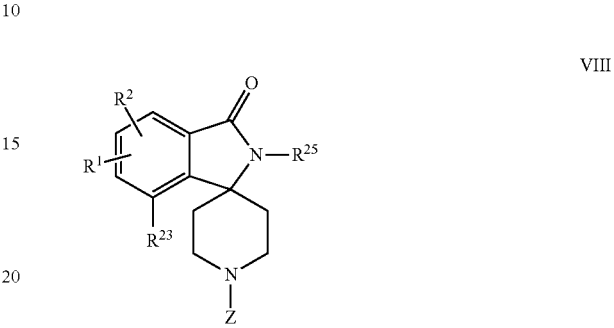

VIII wherein $R^1$, $R^2$, $R^{23}$, $R^{25}$, and Z are as defined above, and pharmaceutically acceptable salts, prodrugs and solvates thereof.

In a further embodiment, compounds useful in the present invention are compounds of Formula I where $Q^1$ is $-C(O)-$, $Q^2$ is $N-R^{26}$, and $Q^3$ is $CR^{23}$, i.e, compounds of Formula IX:

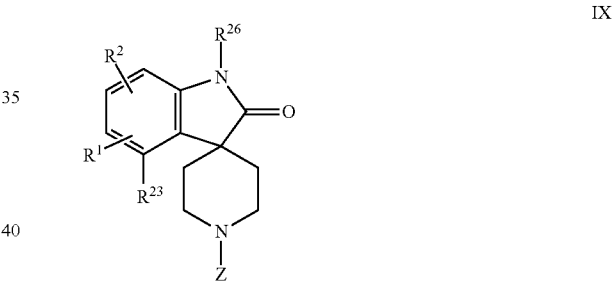

IX wherein $R^1$, $R^2$, $R^{23}$, $R^{26}$, and Z are as defined above, and pharmaceutically acceptable salts, prodrugs and solvates thereof.

Useful compounds of any of Formulae I-IX, as described above, include those where $R^1$ and $R^2$ are each independently hydrogen or $C_{1-4}$ alkyl. Preferably, $R^1$ and $R^2$ are both hydrogen.

In compounds of Formula I where $Q^3$ is $CR^{23}$, $R^{23}$ is preferably hydrogen or $C_{1-4}$ alkyl, more preferably hydrogen.

Useful compounds of any of Formulae I, VIII, and IX, include those where $R^{25}$ and $R^{26}$ are each independently selected from the group consisting of hydrogen, $C_{1-6}$ alkyl, hydroxy($C_{1-6}$)alkyl, $C_{1-6}$ alkoxy($C_{1-6}$)alkyl, halo($C_{1-6}$)alkyl, $C_{3-6}$ cycloalkyl, phenyl, benzyl, and phenethyl, wherein the phenyl ring of any of the phenyl, benzyl and phenethyl groups is optionally substituted with one or two substituents independently selected from the group consisting of $C_{1-6}$ alkyl, $C_{1-6}$ alkoxy, halogen, and halo($C_{1-6}$)alkyl; preferably each independently selected from the group consisting of hydrogen, $C_{1-4}$ alkyl, hydroxy($C_{1-4}$)alkyl, $C_{1-4}$ alkoxy($C_{1-4}$)alkyl, halo($C_{1-4}$)alkyl, $C_{3-5}$ cycloalkyl, phenyl, benzyl, and phenethyl, wherein the phenyl ring of any of the phenyl, benzyl and phenethyl groups is optionally substituted with one or two substituents independently selected from the group consisting of $C_{1-4}$ alkyl, $C_{1-4}$ alkoxy, halogen, and halo($C_{1-4}$) alkyl. More preferably $R^{25}$ and $R^{26}$ are independently selected from the group consisting of hydrogen; methyl; ethyl; propyl; isopropyl; butyl; tert-butyl; hydroxymethyl; hydroxyethyl; methoxymethyl; methoxyethyl; ethoxyethyl; fluoromethyl; difluoromethyl; trifluoromethyl; chloromethyl; chloroethyl; cyclopropyl; unsubstituted phenyl; unsubstituted benzyl; unsubstituted phenethyl; phenyl substituted with one or two substituents independently selected from the group consisting of methyl, ethyl, isopropyl, methoxy, ethoxy, halogen, fluoromethyl, difluoromethyl, and trifluoromethyl; benzyl substituted at the phenyl ring with one or two substituents independently selected from the group consisting of methyl, ethyl, isopropyl, methoxy, ethoxy, halogen, fluoromethyl, difluoromethyl, and trifluoromethyl; and phenethyl substituted at the phenyl ring with one or two substituents independently selected from the group consisting of methyl, ethyl, isopropyl, methoxy, ethoxy, halogen, fluoromethyl, difluoromethyl, and trifluoromethyl. Useful compounds of the invention include those where $R^{25}$ and $R^{26}$ are each independently hydrogen, unsubstituted benzyl, or benzyl substituted at the phenyl ring with one or two substituents independently selected from the group consisting of methyl, ethyl, isopropyl, methoxy, ethoxy, halogen, fluoromethyl, difluoromethyl, and trifluoromethyl. Advantageously, $R^{25}$ and $R^{26}$ are independently hydrogen or unsubstituted benzyl.

Useful compounds of Formula I that may be employed in the method of the present invention include those, as described above, where $R^3$ and $R^4$ are both hydrogen when Z is $Z^1$, A is $CH_2$ or absent and B is CH.

Further useful compounds include those where $Q^1$ is O, $Q^2$ is —C(O)—, $Q^3$ is $CR^{23}$ and $R^3$ and $R^4$ are both hydrogen when Z is $Z^1$, A is —C(O)—, $CH_2$, or absent and B is N.

Useful compounds where $R^3$ and $R^4$ are both hydrogen include those where Z is $Z^2$ and n is 0.

Further useful compounds include those where Z is $Z^2$ and -D-$R^9$ together forms

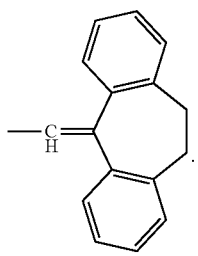 [SMILES: CC=C1c2ccccc2CCc2ccccc21]

Preferably, in these compounds both $R^3$ and $R^4$ are hydrogen. Preferably, in these compounds $Q^1$ is $CR^{20}R^{24}$, where $R^{24}$ is hydrogen, $Q^2$ is $CR^{21}R^{22}$, and $Q^3$ is N.

Useful compounds include those where $R^3$ and $R^4$ together form =O and Z is $Z^1$.

In one embodiment, compounds useful in the present invention are compounds of any one of Formulae I-IX where Z is $Z^1$. Preferably, $R^5$, $R^6$, $R^7$ and $R^8$ are each independently selected from the group consisting of hydrogen, alkyl, alkoxy, halogen, haloalkyl, hydroxy, cyano, amino, alkylamino, and dialkylamino. More preferably, $R^5$, $R^6$, $R^7$ and $R^8$ are each independently selected from the group consisting of hydrogen, $C_{1-6}$ alkyl, $C_{1-6}$ alkoxy, halogen, halo($C_{1-6}$)alkyl, hydroxy, cyano, amino, and di($C_{1-6}$) alkylamino; and more preferably independently selected from the group consisting of hydrogen, $C_{1-4}$ alkyl, $C_{1-4}$ alkoxy, halogen, halo($C_{1-3}$) alkyl, hydroxy, cyano, amino, and di($C_{1-3}$)alkylamino. Advantageously, $R^5$, $R^6$, $R^7$ and $R^8$ are each independently selected from the group consisting of hydrogen, methyl, ethyl, propyl, isopropyl, methoxy, ethoxy, halogen, especially fluorine, trifluoromethyl, hydroxy, cyano, and amino.

Useful compounds include those where $R^5$ and $R^7$ are both hydrogen and $R^6$ and $R^8$ are as defined above. Further useful compounds include those where $R^5$ and $R^7$ are both hydrogen and $R^6$ and $R^8$ are independently selected from the group consisting of hydrogen, methyl, ethyl, propyl, isopropyl, halogen, methoxy, ethoxy, trifluoromethyl, cyano, amino, and dimethylamino. Advantageously, $R^5$ and $R^7$ are both hydrogen and $R^6$ and $R^8$ are both fluorine. Preferably, either or both $R^6$ and $R^8$ are at the para-position of the respective phenyl rings.

In one embodiment, compounds useful in the present invention are compounds of any one of Formulae I-IX where Z is $Z^2$. Useful compounds include those where $R^9$ is phenyl optionally substituted with one or two substituents independently selected from the group consisting of alkyl, alkoxy, halogen, haloalkyl, haloalkoxy, hydroxy, hydroxyalkyl, cyano, amino, aminoalkyl, alkylamino, and dialkylamino; preferably independently selected from the group consisting of alkyl, alkoxy, halogen, haloalkyl, haloalkoxy, amino, alkylamino, and dialkylamino; and more preferably independently selected from the group consisting of $C_{1-6}$ alkyl, $C_{1-6}$ alkoxy, halogen, halo($C_{1-3}$)alkyl, halo($C_{1-3}$)alkyloxy, amino, $C_{1-3}$ alkylamino, and di($C_{1-3}$)alkylamino. Advantageously, $R^9$ is phenyl optionally substituted with one or two substituents independently selected from the group consisting of methyl, ethyl, propyl, isopropyl, methoxy, ethoxy, halogen, especially fluorine, trifluoromethyl, trifluoromethoxy, 2,2,2-trifluoroethoxy, and dimethylamino. Useful compounds include those where $R^9$ is phenyl substituted with one or two substituents as defined above.

Useful compounds include those where $R^9$ is pyridyl, especially 2- or 3-pyridyl, optionally substituted with one or two substituents independently selected from the group consisting of alkyl, haloalkyl, halogen, haloalkoxy, and alkoxy; preferably independently selected from the group consisting of alkyl, alkoxy, and haloalkoxy; and more preferably selected from the group consisting of $C_{1-6}$ alkyl, $C_{1-6}$ alkoxy, and halo($C_{1-3}$)alkyloxy. Advantageously, $R^9$ is pyridyl optionally substituted with one or two substituents independently selected from the group consisting of methyl, ethyl, propyl, isopropyl, methoxy, ethoxy, trifluoromethoxy, and 2,2,2-trifluoroethoxy. Useful compounds include those where $R^9$ is pyridyl substituted with one or two substituents as defined above.

In one embodiment, compounds useful in the present invention are compounds of any one of Formulae I-IX where Z is $Z^3$. Useful compounds include those where $R^{10}$ is phenyl optionally substituted with one or two substituents independently selected from the group consisting of alkyl, alkoxy, halogen, haloalkyl, haloalkoxy, amino, alkylamino, dialkylamino, and alkylcarbonylamino; preferably independently selected from the group consisting of $C_{1-4}$ alkyl, $C_{1-6}$ alkoxy, halogen, halo($C_{1-3}$)alkyl, halo($C_{1-3}$)alkyloxy, amino, $C_{1-3}$ alkylamino, di($C_{1-3}$)alkylamino, and $C_{1-3}$ alkylcarbonylamino; and more preferably independently selected from the group consisting of methyl, ethyl, propyl, isopropyl, methoxy, ethoxy, trifluoromethoxy, and 2,2,2-trifluoroethoxy.

Useful compounds include those where $R^{10}$ is 1,2,3,4-tetrahydroquinolinyl or 1,2,3,4-tetrahydroisoquinolinyl optionally substituted at the nitrogen atom with alkylcarbonyl or haloalkylcarbonyl; preferably optionally substituted with $C_{1-3}$ alkylcarbonyl or halo($C_{1-3}$)alkylcarbonyl. Advantageously, $R^{10}$ is 1,2,3,4-tetrahydroisoquinolinyl, preferably 1,2,3,4-tetrahydroisoquinolin-6-yl, optionally substituted at the nitrogen atom with halo($C_{1-3}$)alkylcarbonyl, preferably trifluoromethylcarbonyl or 2,2,2-trifluoroethylcarbonyl.

In one embodiment, compounds useful in the present invention are compounds of any one of Formulae I-IX where Z is $Z^4$. Preferably, $R^{11}$ and $R^{12}$ are each independently selected from the group consisting of hydrogen; alkyl; alkoxycarbonyl; phenyl optionally substituted with one or two substituents independently selected from the group consisting of alkyl, alkoxy, halogen and haloalkyl; and benzyl optionally substituted at the phenyl ring with one or two substituents independently selected from the group consisting of alkyl, alkoxy, halogen and haloalkyl. More preferably, $R^{11}$ and $R^{12}$ are each independently selected from the group consisting of $C_{1-6}$ alkyl; $C_{1-6}$ alkoxycarbonyl; phenyl optionally substituted with one or two substituents independently selected from the group consisting of $C_{1-4}$ alkyl, $C_{1-4}$ alkoxy, halogen, and halo($C_{1-3}$)alkyl; and benzyl optionally substituted at the phenyl ring with one or two substituents independently selected from the group consisting of $C_{1-4}$ alkyl, $C_{1-4}$ alkoxy, halogen, and halo($C_{1-3}$)alkyl. Advantageously, $R^{11}$ and $R^{12}$ are independently selected from the group consisting of methyl; ethyl; propyl; iso-propyl; butyl; tert-butyl; methoxycarbonyl; ethoxycarbonyl; propoxycarbonyl; iso-propoxycarbonyl; tert-butoxycarbonyl; phenyl optionally substituted with methyl, ethyl, iso-propyl, methoxy, ethoxy, halogen, fluoromethyl, difluoromethyl, or trifluoromethyl; and benzyl optionally substituted at the phenyl ring with methyl, ethyl, iso-propyl, methoxy, ethoxy, halogen, fluoromethyl, difluoromethyl, or trifluoromethyl.

$R^{14}$ is preferably selected from the group consisting of alkyl, hydroxyalkyl, alkoxyalkyl, haloalkyl, and aminoalkyl. More preferably, $R^{14}$ is selected from the group consisting of straight chain $C_{1-6}$ alkyl, branched chain $C_{3-6}$ alkyl, and hydroxy($C_{1-6}$)alkyl. Useful compounds include those where $R^{14}$ is methyl, ethyl, propyl, iso-propyl, butyl, tert-butyl, sec-butyl, or iso-butyl.

In one embodiment, compounds useful in the present invention are compounds of any one of Formulae I-IX where Z is $Z^5$. Preferably, $R^{15}$ is selected from the group consisting of 2-benzo[b]thienyl, 3-benzo[b]thienyl, 1-benzo[c]thienyl, 3-benzo[c]thienyl, 2-benzofuryl, 3-benzofuryl, 1-isobenzofuryl, and 3-isobenzofuryl; more preferably selected from the group consisting of 2-benzo[b]thienyl, 3-benzo[b]thienyl, 1-benzo[c]thienyl, and 3-benzo[c]thienyl.

Useful compounds of any of Formulae I-IX include those where m is 0, 1 or 2. In one aspect, useful compounds of the present invention include those where m is 0, 1, or 2 and A is $CH_2$ or —C(O)—.

Useful compounds of any of Formulae I-IX include those where n is 0, 1, or 2.

Preferably, p is 0.

In one embodiment, useful compounds of the present invention falling within the scope of Formula II include those represented by Formula X:

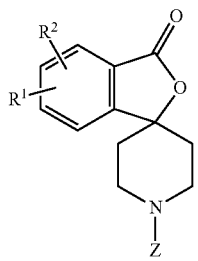

X or a pharmaceutically acceptable salt, prodrug, or solvate thereof, wherein $R^1$, $R^2$, and Z are as defined above. Advantageously, $R^1$ and $R^2$ are both hydrogen.

In one aspect, preferred compounds falling within the scope of Formula X are compounds represented by Formula XI:

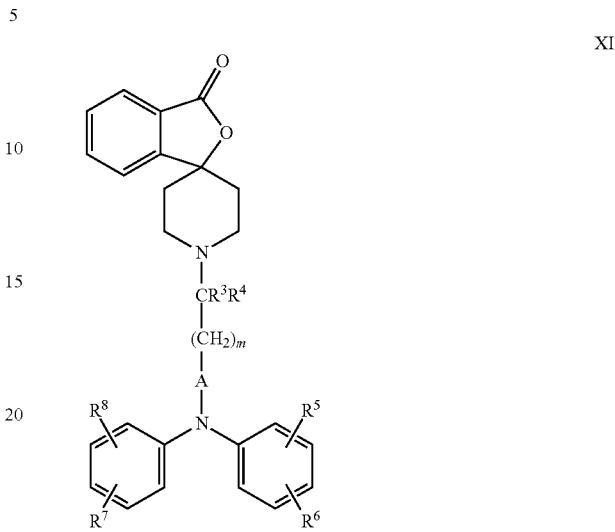

XI or a pharmaceutically acceptable salt, prodrug, or solvate thereof, wherein $R^3$-$R^8$, A, and m are as defined above. Preferred values for $R^3$-$R^8$, A, and m are those described above for Formula I. Especially useful compounds of Formula XI include those where $R^3$ and $R^4$ are both hydrogen. Advantageously, A is $CH_2$ or absent.

In one aspect of the present invention, preferred compounds falling within the scope of Formula X useful in the present invention are compounds represented by Formula XII:

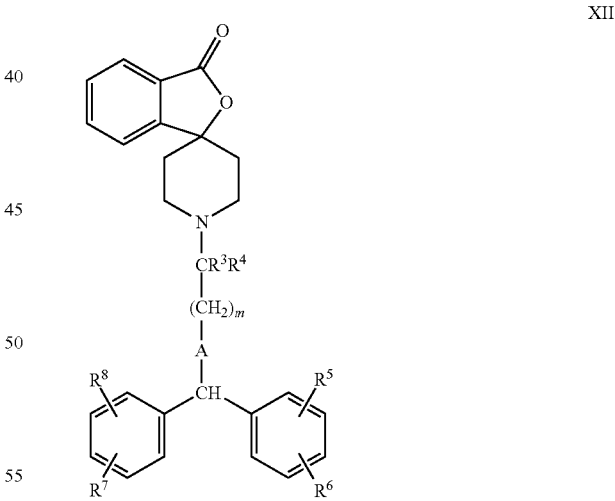

XII or a pharmaceutically acceptable salt, prodrug, or solvate thereof, wherein $R^3$-$R^8$, A, and m are as defined above. Another group of compounds useful in this aspect are compounds of Formula XII where either $R^1$ and $R^4$ together form =O or A is —C(O)—. Preferred values for $R^3$-$R^8$, A, and m are those described above for Formula 1.

Useful compounds of Formula XII include those where $R^3$ and $R^4$ together form =O and A is $CH_2$ or absent.

In one embodiment, useful compounds of the present invention falling within the scope of Formula III include those represented by Formula XIII:

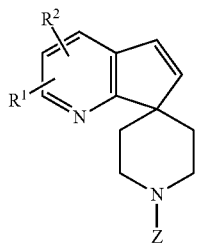

XIII or a pharmaceutically acceptable salt, prodrug, or solvate thereof, wherein $R^1$, $R^2$, and Z are as defined above. Advantageously, $R^1$ and $R^2$ are both hydrogen.

The invention also relates to fused and spirocycle compounds falling within the scope of Formula XIII represented by Formula XIV:

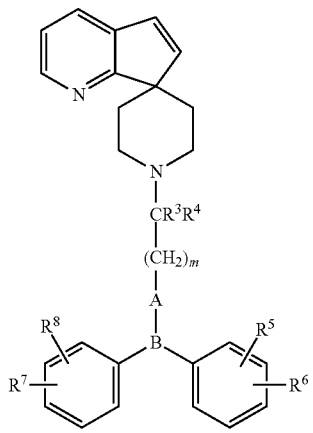

XIV or a pharmaceutically acceptable salt, prodrug or solvate thereof, wherein $R^3$-$R^8$, A, B, and m are as defined above. Preferred values for $R^3$-$R^8$, A, B, and m are those described above for Formula I.

Useful compounds of Formula XIV include those where $R^3$ and $R^4$ are both hydrogen. In these compounds, B is preferably CH. Advantageously, $R^3$ and $R^4$ are both hydrogen, B is CH, and A is $CH_2$ or absent in compounds of Formula XIV.

Further useful compounds of Formula XIV include those where $R^3$ and $R^4$ together form =O. In these compounds, B is preferably CH or A-B is CH=C.

In one embodiment, useful compounds of the present invention falling within the scope of Formula IV include those represented by Formula XV:

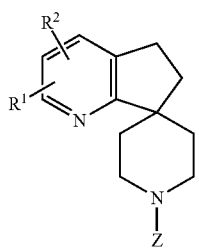

XV or a pharmaceutically acceptable salt, prodrug, or solvate thereof, wherein $R^1$, $R^2$, and Z are as defined above. Advantageously, $R^1$ and $R^2$ are both hydrogen.

In one embodiment, compounds useful in the present invention are compounds falling within the scope of Formula XV represented by Formula XVI:

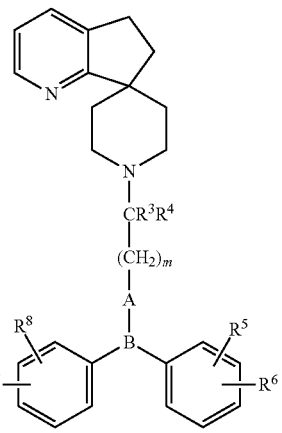

XVI or a pharmaceutically acceptable salt, prodrug or solvate thereof, wherein $R^3$-$R^8$, A, B, and m are as defined above. Preferred values for $R^3$-$R^8$, A, B, and m are those described above for Formula I.

Useful compounds of Formula XVI include those where $R^3$ and $R^4$ are both hydrogen. In these compounds, B is preferably CH. Advantageously, $R^3$ and $R^4$ are both hydrogen, B is CH, and A is $CH_2$ or absent in compounds of Formula XVI.

Further useful compounds of Formula XVI include those where $R^3$ and $R^4$ together form =O. In the compounds, B is preferably CH and A is $CH_2$ or absent.

In one embodiment, useful compounds of the present invention falling within the scope of Formula V include those represented by Formula XVII:

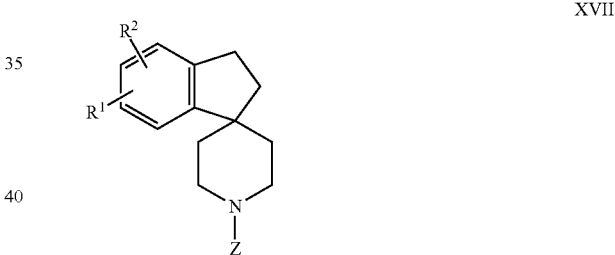

XVII or a pharmaceutically acceptable salt, prodrug, or solvate thereof, wherein $R^1$, $R^2$, and Z are as defined above. Advantageously, $R^1$ and $R^2$ are both hydrogen.

In one embodiment, compounds useful in the present invention are compounds falling within the scope of Formula XVII represented by Formula XVIII:

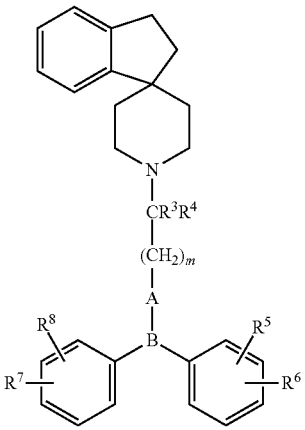

XVIII or a pharmaceutically acceptable salt, prodrug or solvate thereof, wherein $R^3$-$R^8$, A, B, and m are as defined above. Another group of compounds useful in this aspect are compounds of Formula XVIII where A is $CH_2$ or absent, B is CH, and $R^3$ and $R^4$ together form =O. Preferred values for $R^3$-$R^8$, A, B, and m are those described above for Formula I.

Useful compounds of Formula XVIII include those where A-B is CH=C.

In one embodiment, useful compounds of the present invention falling within the scope of Formula VI include those represented by Formula XIX:

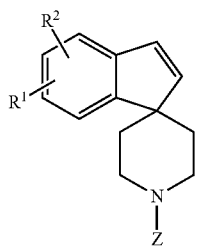

XIX or a pharmaceutically acceptable salt, prodrug, or solvate thereof, wherein $R^1$, $R^2$, and Z are as defined above. Advantageously, $R^1$ and $R^2$ are both hydrogen.

In one embodiment, compounds useful in the present invention are compounds falling within the scope of Formula XIX represented by Formula XX:

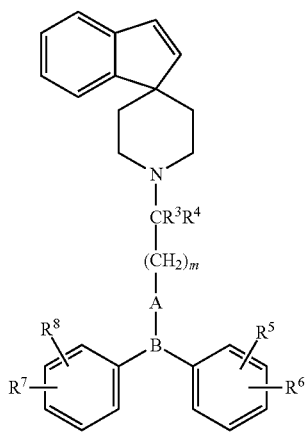

XX or a pharmaceutically acceptable salt, prodrug, or solvate thereof, wherein $R^3$-$R^8$, A, B, and m are as defined above. Another group of compounds useful in this aspect are compounds of Formula XX where A is $CH_2$ or absent, B is CH, and $R^3$ and $R^4$ together form =O. Preferred values for $R^3$-$R^8$, A, B, and m are those described above for Formula I.

Useful compounds of Formula XX include those where A-B is CH=C.

In one embodiment, useful compounds of the present invention falling within the scope of Formula VII include those represented by Formula XXI:

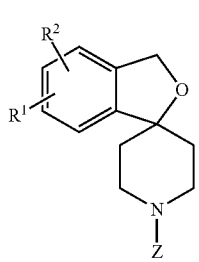

XXI or a pharmaceutically acceptable salt, prodrug, or solvate thereof, wherein $R^1$, $R^2$, and Z are as defined above. Advantageously, $R^1$ and $R^2$ are both hydrogen.

In one embodiment, compounds useful in the present invention are compounds falling within the scope of Formula XXI represented by Formula XXII:

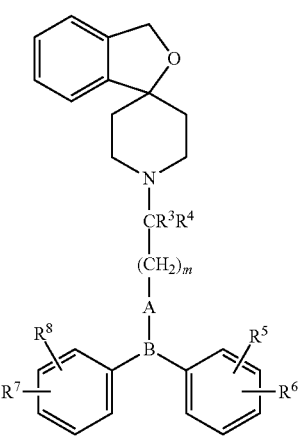

XXII or a pharmaceutically acceptable salt, prodrug or solvate thereof, wherein $R^3$-$R^8$, A, B, and m are as defined above. Another group of compounds useful in this aspect are compounds of Formula XXII where B is CH, A is $CH_2$ or absent, and $R^3$ and $R^4$ together form =O. A further group of useful compounds include compounds of Formula XXII where B is CH, $R^3$ and $R^4$ are both hydrogen, and A is —C(O)—. Preferred values for $R^3$-$R^8$, A, B, and m are those described above for Formula I.

Useful compounds of Formula XXII include those where $R^3$ and $R^4$ together form =O and A is $CH_2$ or absent.

In one embodiment, useful compounds of the present invention falling within the scope of Formula VIII include those represented by Formula XXIII:

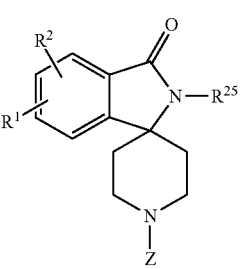

XXIII or a pharmaceutically acceptable salt, prodrug, or solvate thereof, wherein $R^1$, $R^2$, $R^{25}$ and Z are as defined above. Advantageously, $R^1$ and $R^2$ are both hydrogen.

In one embodiment, compounds useful in the present invention are compounds falling within the scope of Formula XXIII represented by Formula XXIV:

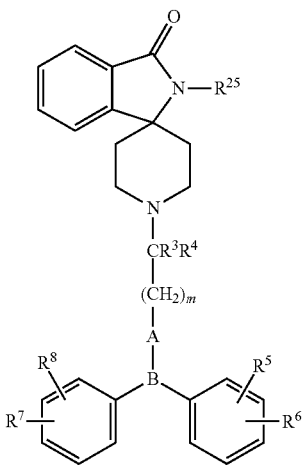

XXIV or a pharmaceutically acceptable salt, prodrug or solvate thereof, wherein $R^3$-$R^8$, A, B, and m are as defined above. Preferred values for $R^3$-$R^8$, $R^{25}$, A, B, and m are those described above for Formula I.

Useful compounds of Formula XXIV include those where $R^{25}$ is hydrogen or benzyl. In these compounds, B is preferably CH. Advantageously, $R^3$ and $R^4$ are both hydrogen, B is CH, and A is $CH_2$ or absent in compounds of Formula XXIV.

In one embodiment, useful compounds of the present invention falling within the scope of Formula IX include those represented by Formula XXV:

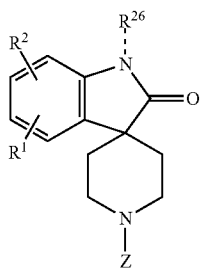

XXV or a pharmaceutically acceptable salt, prodrug, or solvate thereof, wherein $R^1$, $R^2$, $R^{26}$ and Z are as defined above. Advantageously, $R^1$ and $R^2$ are both hydrogen.

In one embodiment, compounds useful in the present invention are compounds falling within the scope of Formula XXV represented by Formula XXVI:

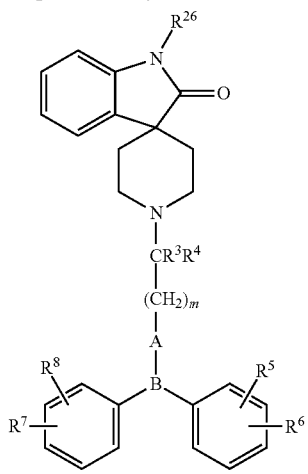

XXVI or a pharmaceutically acceptable salt, prodrug or solvate thereof, wherein $R^3$-$R^8$, A, B, and m are as defined above.

Preferred values for $R^3$-$R^8$, $R^{26}$, A, B, and m are those described above for Formula I.

Useful compounds of Formula XXVI include those where $R^{26}$ is hydrogen or benzyl. In these compounds, B is preferably CH. Advantageously, $R^3$ and $R^4$ are both hydrogen, B is CH, and A is $CH_2$ or absent in compounds of Formula XXVI.

Exemplary compounds that may be employed in the methods of the present invention include:

1,3-dihydro-1'-[4,4-bis(4-fluorophenyl)butyl]-spiro[isobenzofuran-1,4'-piperidine]-3-one;
1,3-dihydro-1'-(3,3-diphenylpropanoyl)-spiro[isobenzofuran-1,4'-piperidine]-3-one;
1,3-dihydro-1'-[4,4-bis(4-fluorophenyl)butanoyl]-spiro[isobenzofuran-1,4'-piperidine]-3-one;
1,3-dihydro-1'-{2-[N,N-bis(4-fluorophenyl)aminocarbonyl]ethyl}-spiro[isobenzofuran-1,4'-piperidine]-3-one;
1,3-dihydro-1'-{2-[N,N-bis(4-fluorophenyl)aminocarbonyl]ethan-1-oyl)}-spiro[isobenzofuran-1,4'-piperidine]-3-one;
1,3-dihydro-1'-[N,N-bis(4-fluorophenyl)aminocarbonylmethyl]-spiro[isobenzofuran-1,4'-piperidine]-3-one;
1,3-dihydro-1'-{3-[N,N-bis(4-fluorophenyl)amino]propyl}-spiro[isobenzofuran-1,4'-piperidine]-3-one;
1,3-dihydro-1'-[4-(4-fluorophenyl)-4-oxobutanoyl]-spiro[isobenzofuran-1,4'-piperidine]-3-one;
1,3-dihydro-1'-(4-trifluoromethylphenylsulfonyl)-spiro-[isobenzofuran-1,4'-piperidine]-3-one;
1,3-dihydro-1'-(4-methoxy-3-trifluoromethylbenzoyl)-spiro[isobenzofuran-1,4'-piperidine]-3-one;
1,3-dihydro-1'-[6-(2,2,2-trifluoroethoxy)pyridin-3-ylcarbonyl]-spiro[isobenzofuran-1,4'-piperidine]-3-one;
1,3-dihydro-1'-(6-methoxypyridin-3-ylcarbonyl)-spiro-[isobenzofuran-1,4'-piperidine]-3-one;
1,3-dihydro-1'-[4-methyl-2-(N-methyl-N-tert-butoxycarbonylamino)-pentanoyl]-spiro[isobenzofuran-1,4'-piperidine]-3-one;
1,3-dihydro-1'-{4-methyl-2-[N-methyl-N-(4-methoxybenzyl)amino]-pentanoyl)}-spiro[isobenzofuran-1,4'-piperidine]-3-one;
and the pharmaceutically acceptable salts, prodrugs and solvates thereof.

Other exemplary compounds useful in the methods of the present invention include:
1-(4,4-bis(4-fluorophenyl)buty)-spiro[piperidine-4,5'-cyclopenta[b]pyridine];
1-(3,3-diphenylpropanoyl)-spiro[piperidine-4,5'-cyclopenta[b]pyridine];
1-(4,4-bis(4-fluorophenyl)-but-3-enoyl)-spiro[piperidine-4,5'-cyclopenta[b]pyridine];
1-(4,4-bis(4-fluorophenyl)butanoyl)-spiro[piperidine-4,5'-cyclopenta[b]pyridine];
1-(4-dimethylaminobenzoyl)-spiro[piperidine-4,5'-cyclopenta[b]pyridine];
1-(4-isopropylbenzyl)-spiro[piperidine-4,5'-cyclopenta[b]pyridine];
1-(4-methoxy-3-trifluoromethylbenzyl)-spiro[piperidine-4,5'-cyclopenta[b]pyridine];
1-(4-isopropylbenzoyl)-spiro[piperidine-4,5-cyclopenta[b]pyridine];
1-(4-methoxybenzyl)-spiro[piperidine-4,5'-cyclopenta[b]pyridine];
1-[2-(10,11-dihydro-5H-dibenzo[a,d]cyclohepten-5-yl-methenyl)ethyl]-spiro[piperidine-4,5'-cyclopenta[b]pyridine];
1-(benzo[b]thiophen-2-ylcarbonyl)-spiro[piperidine-4,5'-cyclopenta[b]pyridine];

1-(N-trifluoromethylcarbonyl-1,2,3,4-tetrahydroisoquinolin-6-yl-sulfonyl)-spiro[piperidine-4,5'-cyclopenta[b]pyridine];
1-(4-trifluoromethylphenylsulfonyl)-spiro[piperidine-4,5'-cyclopenta[b]pyridine];
and the pharmaceutically acceptable salts, prodrugs and solvates thereof.

Further exemplary compounds useful in the methods of the present invention include:
1-[4,4-bis(4-fluorophenyl)butyl]-6',7'-dihydro-spiro[piperidine-4,5'-cyclopenta[b]pyridine];
1-[4,4-bis(4-fluorophenyl)butanoyl]-6',7'-dihydro-spiro[piperidine-4,5'-cyclopenta[b]pyridine];
1-(4-iso-propylbenzyl)-6',7'-dihydro-spiro[piperidine-4,5'-cyclopenta[b]pyridine];
1-(3-trifluoromethyl-4-methoxyphenyl)-6',7'-dihydro-spiro[piperidine-4,5'-cyclopenta[b]pyridine];
and the pharmaceutically acceptable salts, prodrugs and solvates thereof.

Further exemplary compounds useful in the methods of the present invention include:
1-[4,4-bis(4-fluorophenyl)but-3-enoyl]-spiro[piperidine-4,1'-indene];
1-[4,4-bis(4-fluorophenyl)butanoyl]-spiro[piperidine-4,1'-indene];
1-(methoxybenzyl)-spiro[piperidine-4,1'-indene];
1-(3-trifluoromethyl-4-methoxybenzoyl)-spiro[piperidine-4,1-indene];
1-[4,4-bis(4-fluorophenyl)butanoyl]-spiro[piperidine-4,1'-indane];
1,3-dihydro-1'-[4,4-bis(4-fluorophenyl)butyl]-spiro[isobenzofuran-1,4'-piperidine];
and the pharmaceutically acceptable salts, prodrugs and solvates thereof.

Further exemplary compounds useful in the methods of the present invention include:
2-benzyl-2,3-dihydro-1'-[4,4-bis(fluorophenyl)butyl]-spiro[isoindole-1,4'-piperidine]-3-one;
2,3-dihydro-1'-[4,4-bis(fluorophenyl)butyl]-spiro[isoindole-1,4'-piperidine]-3-one;
2,3-dihydro-1'-[4,4-bis(4-fluorophenyl)butyl]-spiro[indole-3,4'-piperidine];
1-benzyl-2,3-dihydro-1'-[4,4-bis(4-fluorophenyl)butyl]-spiro[indole-3,4'-piperidine];
and the pharmaceutically acceptable salts, prodrugs and solvates thereof.

Useful halo or halogen groups include fluorine, chlorine, bromine and iodine.

Useful cycloalkyl groups are selected from $C_{3-12}$ cycloalkyl, preferably $C_{3-6}$ cycloalkyl. Typical cycloalkyl groups include cyclopropyl, cyclobutyl, cyclopentyl, and cyclohexyl.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, iso-butyl, 3-pentyl, hexyl and octyl groups.

Useful alkenyl groups are $C_{2-6}$ alkenyl groups, preferably $C_{2-4}$ alkenyl. Typical $C_{2-4}$ alkenyl groups include ethenyl, propenyl, isopropenyl, butenyl, and sec-butenyl.

Useful haloalkyl groups include $C_{1-10}$ alkyl groups substituted by one or more fluorine, chlorine, bromine or iodine atoms (e.g., fluoromethyl, difluoromethyl, trifluoromethyl, pentafluoroethyl, 1,1-difluoroethyl and trichloromethyl groups).

Useful hydroxyalkyl groups include $C_{1-10}$ alkyl groups substituted by hydroxy (e.g., hydroxymethyl, hydroxyethyl, hydroxypropyl and hydroxybutyl groups).

Useful alkoxy groups include oxygen substituted by one of the $C_{1-10}$ alkyl groups mentioned above.

Useful alkoxycarbonyl groups include carbonyl groups, —C(O)—, substituted by any of the above mentioned alkoxy groups (e.g., methoxycarbonyl, ethoxycarbonyl, propoxycarbonyl, iso-propoxycarbonyl, and tert-butoxycarbonyl).

Useful haloalkoxy groups include oxygen substituted by one of the $C_{1-10}$ haloalkyl groups mentioned above (e.g., fluoromethoxy, difluoromethoxy, and trifluoromethoxy).

Useful alkylamino and dialkylamino groups are —NHR$^{27}$ and —NR$^{27}$R$^{28}$, wherein R$^{27}$ and R$^{28}$ are each independently selected from a $C_{1-10}$ alkyl group.

Useful alkylcarbonyl groups include carbonyl groups, —C(O)—, substituted by any of the above mentioned alkyl groups (e.g., methylcarbonyl, i.e., methanoyl, ethylcarbonyl, propoxycarbonyl, iso-propoxycarbonyl, and tert-butoxycarbonyl).

Useful alkylcarbonylamino groups include carbonylamino groups, —C(O)NH—, substituted with any of the above mentioned alkyl groups (e.g., methylcarbonylamino and ethylcarbonylamino).

Useful haloalkylcarbonyl groups include carbonyl groups substituted with any of the above mentioned haloalkyl groups (e.g., trifluoromethylcarbonyl).

Useful mercaptoalkyl groups include any of the abovementioned $C_{1-10}$ alkyl groups substituted by a —SH group.

Useful alkylthioalkyl groups include any of the abovementioned $C_{1-10}$ alkyl groups substituted by a —S($C_{1-10}$)alkyl group, and preferably substituted by a —S($C_{1-4}$)alkyl group.

As used herein, the term "amino" or "amino group" refers to —NH$_2$.

As used herein, the term "optionally substituted" refers to a group that may be unsubstituted or substituted.

The invention disclosed herein is also meant to encompass prodrugs of any of the disclosed compounds. As used herein, prodrugs are considered to be any covalently bonded carriers that release the active parent drug in vivo. Non-limiting examples of prodrugs include esters or amides of compounds of Formula I-XXVI having hydroxyalkyl or aminoalkyl as a substituent, and these may be prepared by reacting such parent compounds with anhydrides such as succinic anhydride.

The invention disclosed herein is also meant to encompass the in vivo metabolic products of the disclosed compounds. Such products may result, for example, from the oxidation, reduction, hydrolysis, amidation, esterification and the like, of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also intended to encompass the disclosed compounds being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, and preferably $^3$H, $^{11}$C, and $^{14}$C. Isotopically-labeled compounds of the present invention can be prepared by methods known in the art.

The present invention is also directed specifically to $^3$H, $^{11}$C, or $^{14}$C radiolabeled compounds of any of Formulae I-XXVI, as well as their pharmaceutically acceptable salts, prodrugs and solvates, and the use of any such compounds as radioligands for their binding site on the calcium channel. For example, one use of the labeled compounds of the invention is the characterization of specific receptor binding. Another use of a labeled compound of the present invention is an alternative to animal testing for the evaluation of structure-activity relationships. For example, the receptor assay may be performed at a fixed concentration of a labeled compound of the invention and at increasing concentrations of a test compound in a competition assay. For example, a tritiated compound of any of Formulae I-XXVI can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol.* 1, *Labeled Compounds (Part A)*, Chapter 6 (1987). $^{14}$C-labeled compounds can be prepared by employing starting materials having a $^{14}$C carbon.

Some of the compounds disclosed herein may contain one or more asymmetric centers and may thus give rise to enantiomers, diastereomers, and other stereoisomeric forms. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The invention disclosed herein also encompasses the use of salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of any of the disclosed compounds. One type of solvate is a hydrate. Solvates do not significantly alter the physiological activity or toxicity of the compounds, and as such may function as pharmacological equivalents.

Since compounds of Formulae I-XXVI are blockers of calcium ($Ca^{2+}$) channels, a number of diseases and conditions mediated by calcium ion influx can be treated by employing these compounds. The present invention is thus directed generally to a method for treating, preventing or ameliorating a disorder responsive to the blockade of calcium channels, and particularly the selective blockade of N-type calcium channels, in an animal suffering from, or at risk of suffering from, said disorder, said method comprising administering to the animal an effective amount of a compound represented by any of defined Formulae I-XXVI, or a pharmaceutically acceptable salt, prodrug or solvate thereof.

The present invention is further directed to a method of modulating calcium channels, especially N-type calcium channels, in an animal in need thereof, said method comprising administering to the animal at least one compound represented by any of defined Formulae I-XXVI, or a pharmaceutically acceptable salt, prodrug or solvate thereof.

More specifically, the present invention provides a method of treating, preventing or ameliorating stroke, neuronal damage resulting from head trauma, epilepsy, pain (e.g., acute pain or chronic pain, which includes, but is not limited to, neuropathic pain and inflammatory pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia. In one embodiment, the invention provides a method of treating pain. In another embodiment, the type of pain treated is chronic pain. In another embodiment, the type of pain treated is neuropathic pain. In another embodiment, the type of pain treated is inflammatory pain. In another embodiment, the type of pain treated is acute pain. In each instance, such method of treatment, prevention, or amelioration requires administering to an animal in need of such treatment, prevention or amelioration an amount of a compound of the present invention that is therapeutically effective in achieving said treatment, prevention or amelioration. In one embodiment, the amount of such compound is the amount that is effective as to block calcium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, *Inflammatory Pain*, In: *Textbook of Pain*, Wall and Melzack eds., 3rd ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigemninal neuralgia, phantom pain, causalgia, and reflex sympathetic dystrophy and lower back pain. The chronic neuropathic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present invention is also directed to the use of a compound represented by any of defined Formulae I-XXVI, or a pharmaceutically acceptable salt, prodrug or solvate thereof, in the manufacture of a medicament for treating, preventing or ameliorating a disorder responsive to the blockade of calcium channels (e.g., any of the disorders listed above) in an animal suffering from said disorder. In one embodiment, the disorder is responsive to the selective blockade of N-type calcium channels.

Furthermore, the present invention is directed to a method of modulating calcium channels, especially N-type calcium channels, in an animal in need thereof, said method comprising administering to the animal at least one compound represented by any of defined Formulae I-XXVI.

The present invention is also directed to the use of a compound represented by any of defined Formulae I-XXVI, or a pharmaceutically acceptable salt, prodrug or solvate thereof, in the manufacture of a medicament, in particular a medicament for modulating calcium channels, especially N-type calcium channels, in an animal in need thereof.

Synthesis of Compounds

The compounds of the present invention may be prepared using methods known to those skilled in the art in view of this disclosure. For example, compounds of Formula I where Z is $Z^1$ and $R^3$ and $R^4$ are both hydrogen can be prepared as shown in Scheme 1:

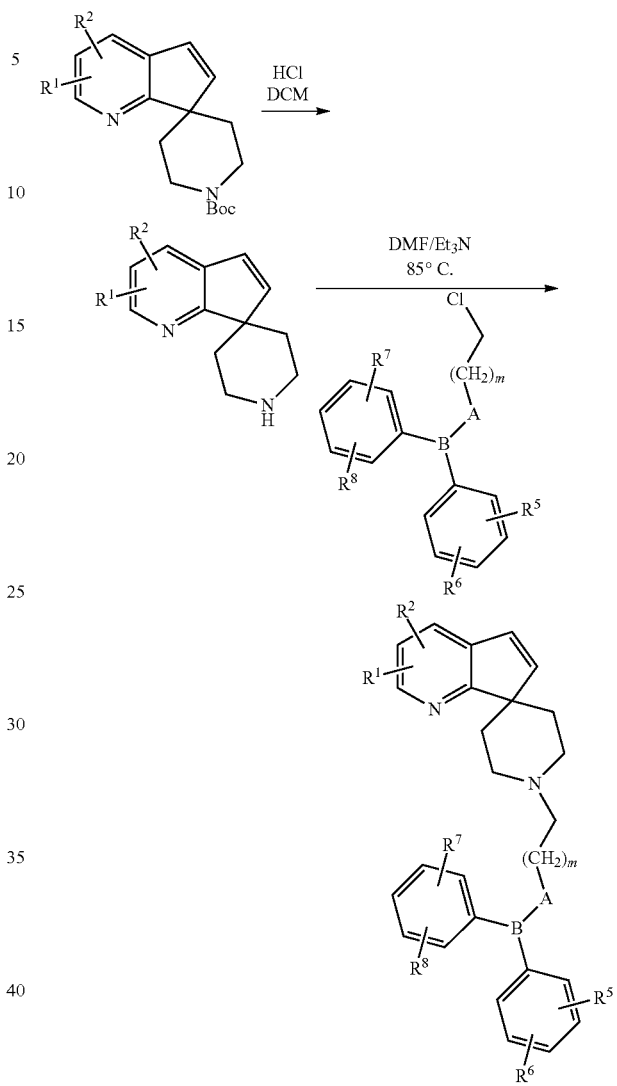

Scheme 1 wherein $R^1$, $R^2$, $R^5$-$R^8$, A, B, and m are as defined above. The method of Scheme 1 can also be used for preparing any corresponding compounds of Formulae I-IX where Z is $Z^1$.

Compounds of Formula I where Z is $Z^1$ and $R^3$ and $R^4$ together form =O can be prepared as shown in Scheme 2:

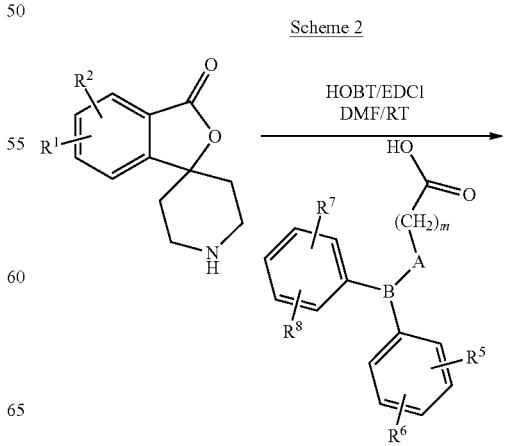

Scheme 2

-continued

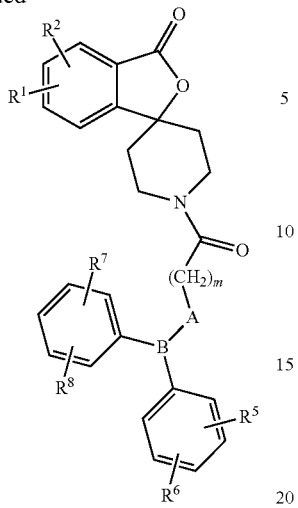

wherein $R^1$, $R^2$, $R^5$-$R^8$, A, B, and m are as defined above. In preparing any corresponding compounds of Formula I where $Q^1$ is $CR^{20}R^{24}$, where $R^{24}$ is hydrogen, $Q^2$ is $CR^{21}R^{22}$ and $Q^3$ is N, advantageously DMAP/EDCI in DMF is used as the reagent. The method of Scheme 2 can be also used for preparing any corresponding compounds of Formulae I-IX where Z is $Z^1$.

Compounds of Formula I where Z is $Z^2$ and $R^3$ and $R^4$ are both hydrogen can be prepared as shown in Scheme 3:

Scheme 3

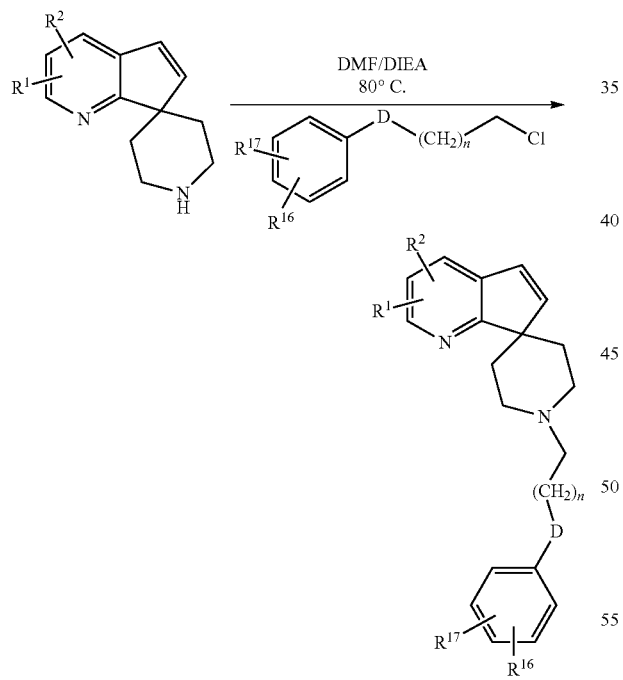

wherein $R^1$, $R^2$, D, and n are as described above and $R^{16}$ and $R^{17}$ are independently selected from the group consisting of hydrogen, alkyl, alkoxy, halogen, haloalkyl, haloalkoxy, hydroxy, hydroxyalkyl, cyano, amino, aminoalkyl, alkylamino, and dialkylamino, or $R^{16}$ and $R^{17}$ in adjacent carbon atoms form a bridge —O—CH$_2$—O—. The method of Scheme 3 can be also used for preparing any corresponding compounds of Formulae I-IX where Z is $Z^2$.

Compounds of Formula I where Z is $Z^2$ and $R^3$ and $R^4$ together form =O can be synthesized as shown in Scheme 4:

Scheme 4

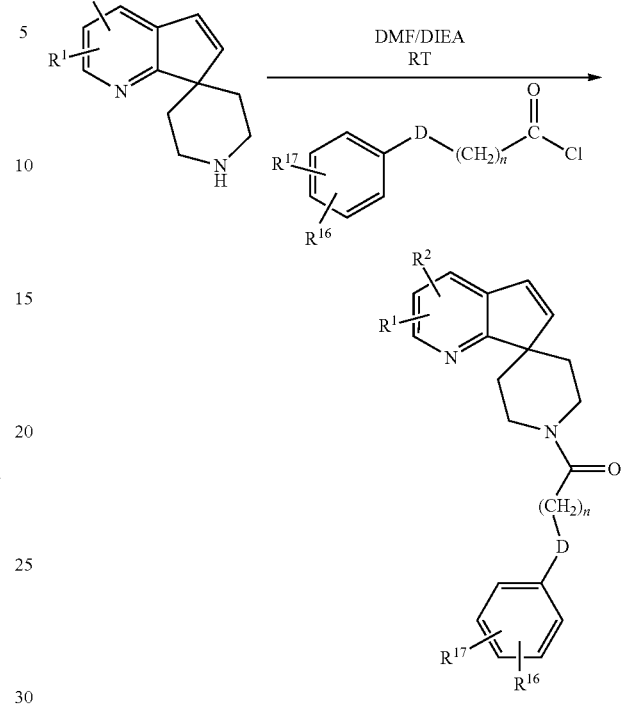

wherein $R^1$, $R^2$, D, and n are as described above and $R^{16}$ and $R^{17}$ are independently selected from the group consisting of hydrogen, alkyl, alkoxy, halogen, haloalkyl, haloalkoxy, hydroxy, hydroxyalkyl, cyano, amino, aminoalkyl, alkylamino, and dialkylamino, or $R^{16}$ and $R^{17}$ together form a bridge —O—CH$_2$—O—. The method of Scheme 4 can be also used for preparing any corresponding compounds of Formulae I-IX where Z is $Z^2$.

Compounds of Formula I where Z is $Z^3$ can be prepared, for example, as shown in Scheme 5:

Scheme 5

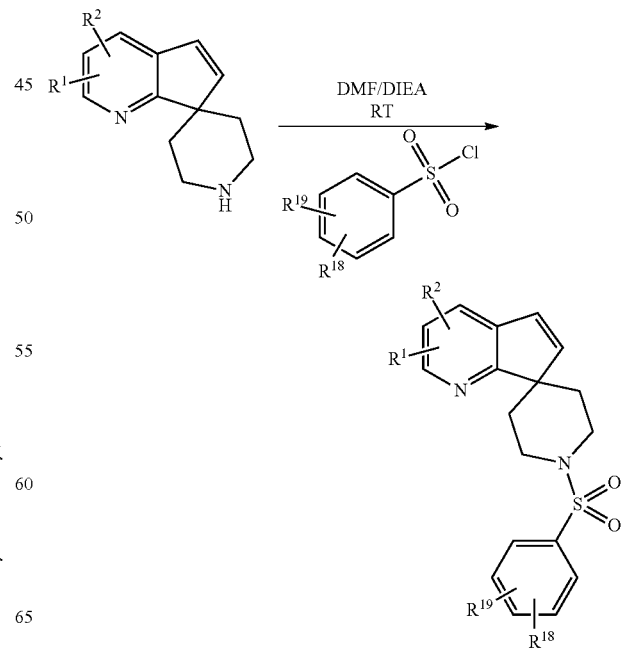

wherein $R^1$ and $R^2$ are as described above and $R^{18}$ and $R^{19}$ are independently selected from the group consisting of hydrogen, alkyl, alkoxy, halogen, haloalkyl, haloalkoxy, amino, alkylamino, dialkylamino, and alkylcarbonylamino. The method of Scheme 5 can be also used for preparing corresponding compounds of any of Formulae I-IX where Z is $Z^3$.

Compounds of Formula I-IX where Z is $Z^4$ can be prepared, inter alia, by using the method described in Example 10 below.

Compounds of Formula I-IX where Z is $Z^5$ can be prepared using methods similar to those described in Schemes 4 and 5 above.

Testing of Compounds

Compounds of the present invention were assessed by calcium mobilization and/or electrophysiological assays for calcium channel blocker activity. One aspect of the present invention is based on the use of the compounds herein described as N-type calcium channel blockers. In one aspect of the present invention, it has been found that certain compounds herein described show selectivity as N-type calcium channel blockers. Based upon this property, these compounds are considered useful in treating, preventing, or ameliorating stroke, neuronal damage resulting from head trauma, migraine, epilepsy, a mood disorder, schizophrenia, a neurodegenerative disorder (such as, e.g., Alzheimer's disease, ALS, or Parkinson's disease), a psychosis, depression, anxiety, hypertension, or cardiac arrhythmia. The compounds of the present invention are also considered to be effective in treating, preventing or ameliorating pain, such as acute pain, chronic pain, which includes but is not limited to neuropathic pain and inflammatory pain, or surgical pain.

More specifically, the present invention is directed to compounds of Formulae I-XXVI that are blockers of calcium channels. According to the present invention, those compounds having preferred N-type calcium channel blocking properties exhibit an $IC_{50}$ of about 100 µM or less in the calcium mobilization and/or electrophysiological assays described herein. Preferably, the compounds of the present invention exhibit an $IC_{50}$ of 10 µM or less. More preferably, the compounds of the present invention exhibit an $IC_{50}$ of about 6 µM or less. Most preferably, the compounds of the present invention exhibit an $IC_{50}$ of about 1.0 µM or less. The compounds of the present invention can be tested for their N-type and L-type $Ca^{2+}$ channel blocking activity by the following calcium mobilization and/or electrophysiological assays.

In one embodiment, compounds useful in the present invention are those represented by any one of Formulae I-XXVI that exhibit selectivity for N-type calcium channels over L-type calcium channels in the calcium mobilization and/or electrophysiological assays described herein. The phrase "selectivity for N-type calcium channels over L-type calcium channels" is used herein to mean that the ratio of an $IC_{50}$ for L-type channel blocking activity for a compound of the present invention over an $IC_{50}$ for N-type channel blocking activity for the same compound is more than 1, i.e., LTCC $IC_{50}$/NTCC $IC_{50}$>1. Preferably, compounds of the present invention exhibit an LTCC $IC_{50}$/NTCC $IC_{50}$ ratio of about 2 or more, about 10 or more, about 20 or more, about 30 or more, about 50 or more, or about 100 or more.

Calcium Mobilization and Electrophysiological Assay Protocols:

Cell Maintenance and Differentiation.

Unless noted otherwise, cell culture reagents were purchased from Mediatech of Herndon, Md. IMR32 cells (American Type Culture Collection, ATCC, Manassas, Va.) were routinely cultured in growth medium consisting of minimum essential medium containing 10% fetal bovine serum (FBS, Hyclone, Logan, Utah), 100 U/mL penicillin, 100 g/mL streptomycin, 2 mM L-glutamine, 1 mM sodium pyruvate, and 1×MEM non-essential amino acids. 80-90% confluent flasks of cells were differentiated using the following differentiation medium: Growth medium plus 1 mM dibutyryl cyclic AMP (Sigma, St. Louis, Mo.), and 2.5 µM bromodeoxyuridine (Sigma). Cells were differentiated for 8 days by replacing differentiation medium every 2-3 days.

A7r5 (ATCC) cells were maintained and routinely cultured in A7r5 growth medium consisting of Dulbecco's Modified Eagles Medium containing 10% FBS, 100 U/mL penicillin, 100 µg/mL streptomycin, 4 mM L-glutamine, and 0.15% sodium bicarbonate. 80-90% confluent flasks of cells were differentiated using the following differentiation medium: A7r5 Growth Medium plus 1 mM dibutyryl cyclic AMP (Sigma). Cells were differentiated for 8 days by replacing differentiation medium every 2-3 days.

Recombinant human embryonal kidney cells (HEK293, ATCC) stably transfected with either N-type calcium channel (NTCC) subunits ($\alpha 1b$, $\alpha 2\delta$, and $\beta 3$) or L-type calcium channel (LTCC) subunits ($\alpha 1c$, $\alpha 2\delta$, and $\beta 1$) were routinely cultured in growth medium consisting of Dulbecco's Modified Eagles Medium containing 10% FBS, 100 U/mL penicillin, 100 µg/mL streptomycin, 4 mM L-glutamine, 500 µg/mL geneticin (G418), 20 µg/mL Blasticidin S (InVivogen, San Diego, Calif.) and 500 µg/mL zeocin (InVivogen).

FLIPR Calcium Mobilization Assay for N-type Calcium Channel.

One day prior to performing this assay, differentiated IMR32 cells were treated with 1× CellStripper, and seeded on poly-D-lysine-coated 96-well clear-bottom black plates (Becton Dickinson, Franklin Lakes, N.J.) at 200,000 cells/well. On the day of the assay, the cell plates were washed with IMR32 buffer (127 mM NaCl, 1 mM KCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then pre-stimulated with KCl and loaded as follows: 0.05 mL of IMR32 buffer, 0.05 mL of each compound tested diluted in IMR32 buffer containing 20 µM nitrendipine (Sigma), and 0.1 mL KCl dissolved in IMR32 buffer, plus Fluo-4 were added (3 µM final concentration, Molecular Probes, Eugene, Oreg.). Final test compound concentrations ranged from about 846 pM to about 17 µM, final nitrendipine concentration was 5 µM, and final KCl concentration was 90 mM. After 1 hour, the cells were washed twice with 0.05 mL of each compound tested in nitrendipine-containing IMR32 buffer (no KCl or Fluo-4), and then replaced with 0.1 mL of each compound tested in nitrendipine-containing IMR32 buffer. Plates were then transferred to a Fluorimetric Imaging Plate Reader ($FLIPR^{96}$, Molecular Devices, Inc., Sunnyvale, Calif.) for assay. The FLIPR measured basal Fluo-4 fluorescence for 315 seconds (i.e., 5 minutes and 15 seconds), then added 0.1 mL KCl agonist dissolved in IMR32 buffer and measured fluorescence for another 45 seconds. Final test compound concentrations on the cells after FLIPR read ranged from about 846 pM to about 17 µM, final nitrendipine concentration was 5 µM, and final KCl concentration was 90 mM. Data were collected over the entire time course and analyzed using Excel, Graph Pad Prism (version 3.02, Graph Pad, San Diego, Calif.), or an in-house non-linear regression analysis software.

FLIPR Calcium Mobilization Assay for L-Type Calcium Channel.

One day prior to performing this assay, HEK293 cells stably expressing recombinant rat L-type calcium channel (LTCC) subunits ($\alpha 1c$, $\alpha 2\delta$, and $\beta 1$) are trypsinized, then seeded on poly-D-lysine-coated 96-well clear-bottom black plates (Becton Dickinson, Franklin Lakes, N.J.) at 75,000 cells/well. On the day of the assay, the plates are washed with LTCC wash buffer (127 mM NaCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then loaded with 0.1 mL of LTCC wash buffer containing Fluo-4 (3 µM final concentration, Molecular Probes, Eugene, Oreg.). After 1 hour, the cells are washed with 0.1 mL LTCC wash buffer and resuspended in 0.05 mL LTCC assay buffer (same composition as LTCC wash buffer). Plates are then transferred to a FLIPR[96] for assay. The FLIPR measures basal Fluo-4 fluorescence for 15 seconds, then adds 0.05 mL of each compound tested diluted in LTCC assay buffer at final concentrations ranging from about 846 pM to about 17 µM. Fluo-4 fluorescence is then measured for 5 minutes. 0.1 mL KCl agonist dissolved in LTCC assay buffer is then added to the cells to produce a final concentration of 90 mM KCl, and fluorescence is measured for another 45 seconds. Data are collected over the entire time course and analyzed using Excel, Graph Pad Prism, or an in-house regression analysis software.

Alternative FLIPR Calcium Mobilization Assay for L-type Calcium Channel.

Alternatively, the following cell line and procedure was used for the FLIPR calcium mobilization assay for L-type calcium channel. One day prior to performing this assay, differentiated A7r5 cells were trypsinized, then seeded on tissue culture treated 96-well clear-bottom black plates (Becton Dickinson, Franklin Lakes, N.J.) at a dilution of 1:1 from a confluent T150 $cm^2$ flask. On the day of the assay, the plates were washed with A7r5 wash buffer (127 mM NaCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then loaded with 0.1 mL of A7r5 wash buffer containing Fluo-4 (3 µM final concentration, Molecular Probes, Eugene, Oreg.). After 1 hour, the cells were washed with 0.1 mL A7r5 wash buffer and resuspended in 0.05 mL A7r5 assay buffer that was composed of A7r5 wash buffer plus 50 M valinomycin (Sigma). Plates were then transferred to a FLIPR[96] for assay. The FLIPR measured basal Fluo-4 fluorescence for 15 seconds, then added 0.05 mL of each compound tested diluted in A7r5 assay buffer at final concentrations ranging from about 846 pM to about 17 µM. Fluo-4 fluorescence was then measured for 5 minutes. 0.1 mL KCl agonist dissolved in A7r5 assay buffer is then added to the cells to produce a final concentration of 90 mM KCl, and fluorescence was measured for another 45 seconds. Data were collected over the entire time course and analyzed using Excel, Graph Pad Prism, or an in-house regression analysis software.

Cloning of N- and L-Type Calcium Channel Subunit Open Reading Frame cDNAs.

Five cDNAs encoding subunits of the rat N- or L-type calcium channels were cloned by PCR amplification in order to reconstitute functional channels in a heterologous system. These were the alpha1b (α1b), beta1 (β1), beta3 (β3), alpha2delta (α2δ), and alpha1c (α1c) subunit cDNAs. The alpha1b subunit cDNA has been described by Dubel et al. in *Proc. Natl. Acad. Sci. U.S.A* 89: 5058-5062 (1992). The beta1 subunit cDNA has been described by Pragnell et al. in *FEBS Lett.* 291: 253-258 (1991). The beta3 subunit cDNA has been described by Castellano et al. in *J. Biol. Chem.* 268: 12359-12366 (1993). The alpha2delta subunit cDNA has been described by Kim et al. in *Proc. Natl. Acad. Sci. U.S.A.* 89: 3251-3255 (1992). The alpha1c subunit cDNA has been described by Koch et al. in *J. Biol. Chem.* 265: 17786-17791 (1990).

The 7.0 kb cDNA containing the entire α1b open reading frame (ORF) was PCR amplified as two overlapping cDNA fragments, i.e., a 2.7 kb 5' fragment and a 4.4 kb 3' fragment. The 5' fragment was amplified from rat brain cDNA using primers 1 (SEQ ID NO:1, TABLE 1) and 2 (SEQ ID NO:2, TABLE 1), and the 3' fragment was amplified from rat spinal cord cDNA using primers 3 (SEQ ID NO:3, TABLE 1) and 4 (SEQ ID NO:4, TABLE 1). The two fragments were joined by ligation at a common restriction site to create the entire 7.0 kb cDNA. This ORF encodes the protein isoform generated by alternative splicing termed "+A ΔSFMG ΔET" according to the nomenclature of Lin et al. (*Neuron* 18: 153-166 (1997)). The entire cDNA was sequenced with redundant coverage on both strands. The cDNA was then inserted into the mammalian expression vector pcDNA6.2DEST (Invitrogen, Carlsbad Calif.) by homologous recombination using the Gateway system (Invitrogen).

The 1.8 kb cDNA encoding the β1 subunit, the 1.45 cDNA encoding the beta3 subunit, and the 3.3 kb cDNA encoding the alpha2delta subunit were cloned by PCR amplification from rat spinal cord cDNA (β1) or brain cDNA (β3, α2δ). Primers 5 (SEQ ID NO:5, TABLE 1) and 6 (SEQ ID NO:6, TABLE 1) were used for the β1 cDNA amplification; primers 7 (SEQ ID NO:7, TABLE 1) and 8 (SEQ ID NO:8, TABLE 1) were used for the β3 cDNA amplification; and primers 9 (SEQ ID NO:9, TABLE 1) and 10 (SEQ ID NO:10, TABLE 1) were used for the α2δ cDNA amplification. PCR products were subcloned and fully sequenced on both strands. Clones matching the reference sequence (β1: NM_017346; β3: NM_012828; α2δ: M86621) and the gene's GenBank rat genomic DNA sequences were recombined into the mammalian expression vector pcDNA3.2DEST (β1, β3) or pcDNA3.1-Zeo (α2δ), which had been modified to a vector compatible with the Gateway recombination system using the Gateway vector adaptor kit (Invitrogen). Proper recombination was confirmed by sequencing of recombinogenic regions. For β3 expression vector, proper protein expression was confirmed by Western blot analysis of lysates of transfected HEK293 cells using a rabbit polyclonal antiserum directed against the rat β3 subunit (USA Biological).

The 6.5 kb cDNA encoding the L-type calcium channel α1c subunit was cloned by PCR amplification from rat heart cDNA using primers 11 (SEQ ID NO: 11, TABLE 1) and 12 (SEQ ID NO:12, TABLE 1). The PCR fragment was subcloned and fully sequenced on both strands to confirm its identity. A clone matching consensus reference sequence M59786 and rat genomic DNA sequences was recombined into the mammalian expression vector pcDNA6.2DEST. Sequences around the recombinogenic region were sequenced to confirm accurate recombination into the expression vector.

TABLE 1

| PRIMER SEQUENCE | SEQ ID NO. |
|---|---|
| CACC ATG GTC CGC TTC GGG GAC | 1 |
| CCG TTC AGT GGC CTC CTC C | 2 |
| C TAG CAC CAG TGA TCC TGG TCTG | 3 |
| AGT GCG TTG TGA GCG CAG TA | 4 |
| CAC CAT GGT CCA GAA GAG CGG | 5 |
| TCTCAGCGGATGTAGACGCCT | 6 |
| CAC CAT GTA TGA CGA CTC CTA C | 7 |

TABLE 1-continued

| PRIMER SEQUENCE | SEQ ID NO. |
|---|---|
| GGT GGT CAG TAG CTG TCC TTA GG | 8 |
| CAC CAT GGC TGC TGG CTG CCT | 9 |
| AGA GGG TCA CCA TAG ATA GTG TCT G | 10 |
| CACCATGATTCGGGCCTTCGCT | 11 |
| AGCCTGCGGACTACAGGTTGCTGAC | 12 |

N-type Recombinant Cell Line Development.

N-type calcium channel expressing HEK-293 cells were created in two stages. Stage 1 was created as follows. The rat α1b, and β3 cDNA expression constructs (2.5 µg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 µg/mL blasticidin and 500 g/mL geneticin, and incubated for 3 weeks at 37° C., 5% $CO_2$, 95% humidity. Plates containing ≤1 clone per well were cultured until wells positive for single clones were confluent. Individual clones were then arrayed into columns of a destination 96-well plate, and partly split into 6-well plates for culture maintenance. Array plates were washed once with IMR32 buffer and cells loaded for 1 hour with 0.1 mL of IMR32 buffer containing Fluo-4 (3 µM final concentration, Molecular Probes). Then they were washed twice with 0.1 mL of IMR32 buffer, and replaced with 0.1 mL IMR32 buffer. Plates were then transferred to a FLIPR[96] for assay. The FLIPR measured basal Fluo-4 fluorescence for 315 seconds, then added 0.1 mL KCl agonist dissolved in IMR32 buffer and measured fluorescence for another 45 seconds. Final KCl concentration was 90 mM. Data were collected over the entire time course and analyzed using Excel, Graph Pad Prism, or Activity Base (version 5.1, IDBS, Parsippany, N.J.) software. The clone with the greatest signal-to-noise ratio, best stability of response with passage number, and best adhesion to PDL precoated plates (Becton Dickinson) was expanded, characterized and used for stage 2 cell line development.

Stage 2 of N-type cell line development was carried out as follows. The rat α2δ cDNA expression construct (5 µg each) was transfected into the stage 1 N-type clonal cell line by Lipofectamine Plus reagent (Invitrogen), as per manufacturer's instructions. 24 hours later, cells were split in limiting dilution into multiple 96-well plates in selection media containing 20 µg/mL blasticidin, 500 µg/mL geneticin, and 250 µg/mL zeocin and incubated for 3 weeks at 37° C., 5% $CO_2$, 95% humidity. Plates containing ≤1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded, characterized and tested in electrophysiology for the best current size, N-type pharmacology, N-type characteristic current-voltage relationship and kinetics as described below.

L-type Recombinant Cell Line Development.

L-type calcium channel expressing HEK-293 cells were created in two stages. Stage 1 was created as follows. The rat α1c, and β1 cDNA expression constructs (2.5 µg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 µg/mL blasticidin and 500 µg/mL geneticin, and incubated for 3 weeks at 37° C., 5% $CO_2$, 95% humidity. Plates containing ≤1 clone per well were cultured until wells positive for single clones were confluent. Individual clones were then arrayed into columns of a destination 96-well plate, and partly split into 6-well plates for culture maintenance. Array plates were washed once with LTCC wash (or assay) buffer and cells loaded for 1 hour with 0.1 mL of LTCC buffer containing Fluo-4 (3 µM final concentration, Molecular Probes). Then they were washed twice with 0.1 mL of LTCC buffer, and replaced with 0.1 mL LTCC buffer. Plates were then transferred to a FLIPR[96] for assay. The FLIPR measured basal Fluo-4 fluorescence for 315 seconds, then added 0.1 mL KCl agonist dissolved in LTCC buffer and measured fluorescence for another 45 seconds. Final KCl concentration was 90 mM. Data were collected over the entire time course and analyzed using Excel, Graph Pad Prism, or Activity Base software. The clone with the greatest signal-to-noise ratio, best stability of response with passage number, and best adhesion to PDL precoated plates (Becton Dickinson) was expanded, characterized and used for stage 2 cell line development.

Stage 2 of L-type cell line development was carried out as follows. The rat α2δ cDNA expression construct (5 µg each) was transfected into the stage 1 L-type clonal cell line by Lipofectamine Plus reagent (Invitrogen), as per manufacturer's instructions. 24 hours later, cells were split in limiting dilution into multiple 96-well plates in selection media containing 20 µg/mL blasticidin, 500 µg/mL geneticin, and 250 µg/mL zeocin and incubated for 3 weeks at 37° C., 5% $CO_2$, 95% humidity. Plates containing ≤1 clone per well were cultured and handled according to the same steps and procedures described above for the stage 1 cell line. The three clones with the greatest signal-to-noise ratio, best stability of response with passage number, and best adhesion to PDL precoated plates (Becton Dickinson) were expanded and characterized.

N-type Electrophysiology in Recombinant Cells.

For electrophysiological recording, the cells expressing α1b, β3 and α2δ subunits were seeded on 35-mm culture Petri dishes at a density of approximately $10^4$ cells/dish and kept in an incubator for up to three days for subsequent recordings. For recordings, the dishes were positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings were made using conventional patch-clamp techniques (Hamill et al., *Pfluegers Arch.* 391: 85-100 (1981)) at room temperature (22-24° C.). The patch-clamp pipettes were pulled from WPI, thick-walled borosilicate glass (WPI, Sarasota, Fla.). Currents were recorded using an Axopatch 200A amplifier (Axon Instruments, Union City, Calif.) and were leak-subtracted (P/4), low-pass filtered (1 kHz, 4-pole Bessel), digitized (20-50-µs intervals), and stored using Digidata 1200 B interface and Pclamp8.0/ Clampex software (Axon Instruments, Union City, Calif.). The pipettes were back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranged from 2 to 3 MOhm and was compensated by 75-80% by the built-in electronic circuitry.

Currents were elicited by stepping from a holding potential of −90 mV to 0 mV for 20 ms every 20 sec. At the −90 mV membrane voltage about 50% of channels were in the inactivated state, and thus contact with a blocker would involve interaction with both resting and inactivated channels. Every drug was applied at 3 to 4 concentrations increasing in a cumulative manner. Fractional inhibition levels in steady-state were used to draw the partial inhibition concentration curves to get the $IC_{50}$ (i.e. concentration causing 50% reduction in the size of the response) values at −90 mV.

Stock solutions of each test compound were prepared using DMSO. Serial dilutions to desired concentrations were done with bath solution; concentration of DMSO in final solutions was 0.1%. Drugs were applied by gravity flow using a plane multi-barrel array shooter positioned 0.5 mm apart from the cell.

All curve fittings were carried out using Origin software (version 5.0, Microcal). A Hill equation was fit to the concentration-inhibition curves to determine $IC_{50}$ values.

N-type Electrophysiology in Neuronal Cells.

To determine dissociation constants in resting versus inactivated state for N-type calcium channels, neuronal cells that endogenously express N-type calcium channels can be used. For electrophysiological recording, the neuronal cells expressing N-type calcium channels are seeded on 35-mm culture Petri dishes at a density of approximately $10^4$ cells/dish and kept in an incubator for up to three days for subsequent recordings. For recordings, the dishes are positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings are made using conventional patch-clamp techniques (Hamill et al., *Pfluegers Arch.* 391: 85-100 (1981)) at room temperature (22-24° C.). The patch-clamp pipettes are pulled from WPI, thick-walled borosilicate glass (WPI, Sarasota, Fla.). Currents are recorded using an Axopatch 200A amplifier (Axon Instruments, Union City, Calif.) and leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes are back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranges from 2 to 3 MOhm and is compensated by 75-80% by the built-in electronic circuitry.

Currents are elicited by stepping from a holding potential of −90 mV to 0 mV for 20 ms every 10 sec. At the −90 mV membrane voltage a proportion of channels is in the inactivated state, and thus contact with a blocker would involve interaction with both resting and inactivated channels. This protocol is used as a first tier screen. For dissection of two components of inhibition (resting block with the apparent dissociation constant $K_r$ and inactivated state block with $K_i$), steady-state inactivation curves are collected using a double-pulse protocol. Three-second long depolarizing pre-pulse incrementing in 10 mV steps is followed by a 10 ms test pulse to 0 mV.

Stock solutions of each test compound are prepared using DMSO. Serial dilutions to desired concentrations are done with bath solution; concentration of DMSO in final solutions is 0.1%. Drugs are applied by gravity flow using a plane multi-barrel array shooter positioned ~1 mm apart from the cell.

All curve fittings can be carried out using Origin software (version 5.0, Microcal). A Hill equation is used to fit the concentration-response curves and to determine $IC_{50}$ values. A Boltzman equation is used to fit inactivation curves, returning half-inactivation voltage, $V_{0.5}$, slope p and the amplitude of current at the most negative voltage where eventually all channels are in the resting state. These parameters are used to calculate the apparent dissociation constants: $K_r=((Ab/Ac)/(1-(Ab/Ac))[b])$ where [b] is the drug concentration, Ac is the maximum test current amplitude in control conditions and Ab is the maximum test current amplitude in the presence of a blocker; $K_i=[b]/((exp(-(dx/p))*(1+([b]/K_r))-1)$ where dx is the difference between half-inactivation voltage $V_{0.5}$ in the presence and absence of drug and p is the slope.

In Vivo Pharmacology

The compounds of the present invention can be tested for in vivo anticonvulsant activity after i.v., p.o., or i.p. injection using any of a number of anticonvulsant tests in mice or rats, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/see, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

The compounds can be tested for their antinociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period mice are weighed and given either the compound of interest administered i.p. or p.o., or the appropriate volume of vehicle (e.g., 10% Tween-80) as control. Fifteen minutes after the i.p. dosing, and 30 minutes after the p.o. dosing mice are injected with formalin (20 L of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value<0.05 is considered significant. Compounds are considered to be efficacious for treating acute and chronic pain if they have activity in blocking both the early and second phase of formalin-induced paw-licking activity.

Compounds can be tested for their potential to treat chronic pain (i.e., antiallodynic and antihyperalgesic activities) using the Chung model of peripheral neuropathy (Kim and Chung, *Pain* 50: 355-363 (1992)). Male Sprague-Dawley rats weighing between 200-225 g are anesthetized with halothane (1-3% in a mixture of 70% air and 30% oxygen), and their body temperature controlled during anesthesia through use of a homeothermic blanket. A 2-cm dorsal midline incision is then made at the L5 and L6 level, and the para-vertebral muscle groups retracted bilaterally. L5 and L6 spinal nerves are then exposed, isolated, and tightly ligated with 6-0 or 7-0 silk suture. A sham operation is performed exposing the contralateral L5 and L6 spinal nerves, without ligating, as a negative control.

Tactile Allodynia:

Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to mammal, e.g. human, orally at a dose of from about 0.0025 to about 1500 mg per kg body weight of the mammal, or an equivalent amount of a pharmaceutically acceptable salt, prodrug or solvate thereof, per day to treat the particular disorder. A useful oral dose of a compound of the present invention administered to a mammal is from about 0.0025 to about 50 mg per kg body weight of the mammal, or an equivalent amount of the pharmaceutically acceptable salt, prodrug or solvate thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily as one or more tablets, each containing from about 0.01 to about 50 mg of the compound, or an equivalent amount of a pharmaceutically acceptable salt or solvate thereof.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

In one embodiment, a pharmaceutical composition of the present invention can be administered orally and is formulated into tablets, dragees, capsules or an oral liquid preparation. In one embodiment, the oral formulation comprises extruded multiparticulates comprising the compound of the invention.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal or transmucosal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

A method of the present invention, such as a method for treating, preventing, or ameliorating a disorder responsive to the blockade of calcium channels in an animal in need thereof, can further comprise administering a second therapeutic agent to the animal in combination with a compound of the present invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

A compound of the present invention (i.e., the first therapeutic agent) and the other therapeutic agent can act additively or, in one embodiment, synergistically. In one embodiment, a compound of the present invention is administered concurrently with a second therapeutic agent; for example, a single composition comprising an effective amount of a compound of Formulae I-XXVI, and an effective amount of the second therapeutic agent can be administered. Accordingly, the present invention further provides a pharmaceutical composition comprising a combination of a compound of the present invention, the second therapeutic agent, and a pharmaceutically acceptable carrier. Alternatively, a first pharmaceutical composition comprising an effective amount of a compound of any of Formulae I-XXVI and a second pharmaceutical composition comprising an effective amount of the second therapeutic agent can be concurrently administered. In another embodiment, an effective amount of a compound of the present invention is administered prior or subsequent to administration of an effective amount of the second therapeutic agent. In this embodiment, the compound of the present invention is administered while the second therapeutic agent exerts its therapeutic effect, or the second therapeutic agent is administered while the compound of the present invention exerts its preventive or therapeutic effect for treating, preventing, or ameliorating a disorder or condition.

The second therapeutic agent can be, but is not limited to, an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs in Remington: The Science and Practice of Pharmacy* Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocomine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproelozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramin, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating or preventing an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar, steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine funmarate; haloperidol; haloperidol decanoate; loxapine succinate; molindone hydrochloride; pimozide; and ziprasidone.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-HT3 receptor antagonists such as odansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the present invention is preferably manufactured in a manner which is itself known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such a suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

1-(4,4-Bis(4-fluorophenyl)butyl)-spiro[piperidine-4, 5'-cyclopenta[b]pyridine] (10)

a) To a solution of 25.0 g (209.8 mmol) of the pyridine compound 1 in 200 mL of dichloromethane (DCM) at 0° C. was added m-chloroperbenzoic acid (m-CPBA) portionwise. The resulting mixture was stirred at 0° C. for 2 hours, warmed to room temperature and stirred for an additional 7 hours. After this period, a saturated solution of 50 mL of aqueous $Na_2S_2O_3$ was added and the mixture was stirred for 0.5 hour. A saturated solution of 50 mL of aqueous $NaHCO_3$ was added slowly to this mixture. The layers were separated, and the aqueous layer was extracted with 500 mL of DCM. The organic layers were combined and washed with 100 mL of brine solution and dried with anhydrous $Na_2SO_4$. The organic layer was then concentrated to give 21.3 g of the N-oxide 2 as a white solid.

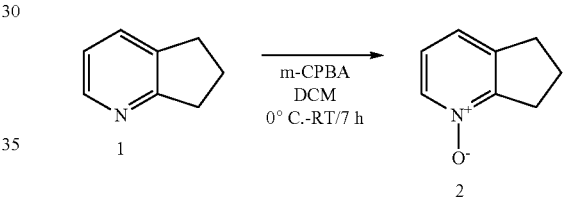

b) A 20 g portion of the N-oxide 2 was dissolved in 161.5 mL of acetic anhydride/water solution (99:1). The resulting pink solution was stirred at room temperature for 10 hours and then heated to 100° C. for 3.5 hours. After this period, the reaction mixture was cooled to room temperature and the acetate 3 was isolated from the crude mixture by using vacuum distillation (16.2 g).

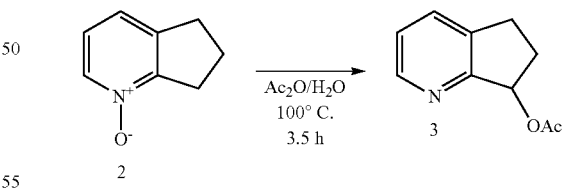

c) Concentrated sulfuric acid (12.0 mL) was added portionwise with vigorous stirring to 10.2 g of acetate 3 at room temperature. After the addition was complete, the reaction mixture was heated to 125° C. for 2 hours. The reaction mixture was then cooled to room temperature and poured into 100 g of ice. A 50 g portion of 50% aqueous NaOH solution was added slowly to the reaction mixture. The aqueous layer was extracted with 100 mL of ether three times. The organic layer was dried over $K_2CO_3$ and concentrated to give 6.2 g of compound 4 as an orange oil.

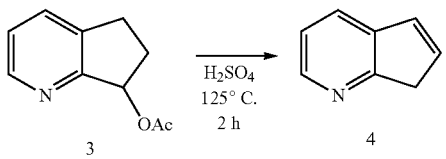 [SMILES: CC(=O)OC1CCc2cccnc21 ; C1=Cc2cccnc2C1]

d) To a stirred solution of the pyridyl compound 4 (6.0 g, 51.22 mmol) in THF (25 mL) at 0° C. was added 102.44 mL (102.44 mmol) of LiHMDS (5). The resulting mixture was stirred at 0° C. for 1 hour and transferred via cannula to a THF (50 mL) solution of compound 6 at 0° C. The resulting reaction mixture was stirred at 0° C. for 1 hour and at room temperature for 12 hours. The solvent was removed by rotary evaporator and the residue was purified by flash chromatography using a gradient of ethyl acetate/hexane as eluent to give 3.2 g of the BOC-protected spirocycle 7. MS: m/z 287. $^1$H NMR (400 MHz, CDCl$_3$): δ 8.38-8.33 (m, 1H), 7.59-7.54 (m, 1H), 7.17-7.11 (m, 1H), 6.89-6.75 (m, 2H), 4.34-4.12 (m, 2H), 3.33-3.17 (m, 2H), 2.15-2.04 (m, 2H), 1.49 (s, 9H), 1.42-1.31 (m, 2H).

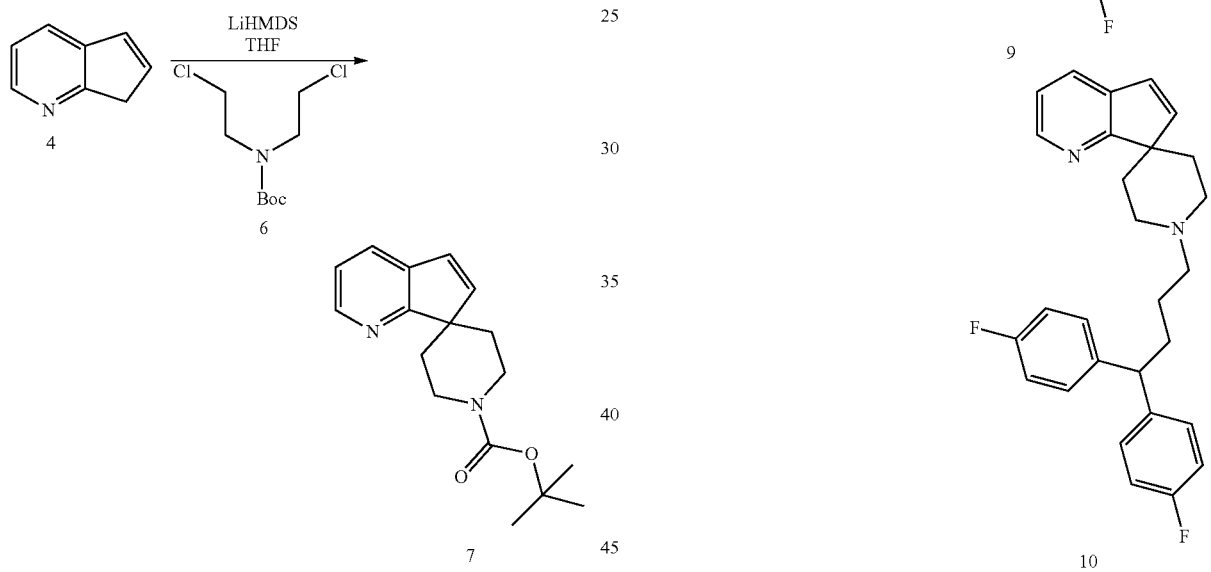

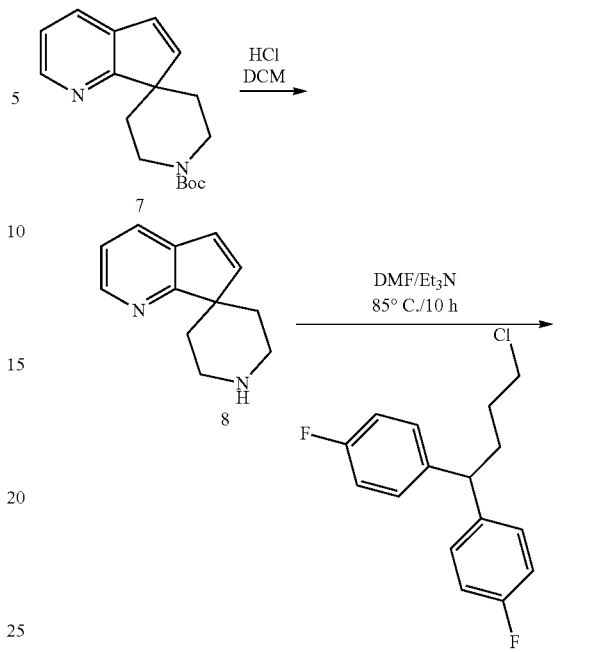

e) 1-(4,4-Bis(4-fluorophenyl)butyl)-spiro[piperidine-4,5'-cyclopenta[b]pyridine] (10): 5 mL of 2M HCl in ether (Aldrich) was added to the BOC protected spirocycle 7 (0.62 g, 2.17 mmol) dissolved in 3 mL of DCM. The resulting mixture was stirred at room temperature for 10 hours and the volatiles were removed by flushing with nitrogen gas followed by rotary evaporator to give the spirocycle 8, that was redissolved in 6.0 mL of DMF. 0.6 mL (4.34 mmol) of triethylamine and 0.73 g (2.59 mmol) of the alkyl chloride 9 (Across) were added to the DMF solution of the compound 8 at room temperature. The resulting mixture was stirred at 85° C. for 10 hours. The solvent was removed by Genevac®, and the resulting crude sample was purified by column chromatography using a gradient of ethyl acetate/hexane as eluent to give 0.2 g of the title compound 10. MS: m/z 430. $^1$H NMR (400 MHz, CDCl$_3$): δ 8.27-8.22 (m, 1H), 7.58-7.53 (m, 1H), 7.19-7.08 (m, 1H), 6.99-6.91 (m, 4H), 6.87 (s, 2H), 6.75-6.70 (m, 1H), 6.50-6.43 (m, 1H), 3.94-3.77 (m, 3H), 3.63-3.42 (br s, 2H), 3.27-3.15 (m, 2H), 2.61-2.39 (br s, 2H), 2.16-2.04 (m, 2H), 1.84-1.72 (m, 2H), 1.70-1.47 (br s, 2H).

Example 2

1,3-Dihydro-1'-[4,4-bis(4-fluorophenyl)butyl]-spiro[isobenzofuran-1,4'-piperidine]-3-one (12)

To a DMF (3.0 mL) solution of 0.4 g (1.97 mmol) of the spirocycle 11 (Arch corporation) at room temperature was added 0.4 g (1.97 mmol) of the alkyl chloride 9 (Across) and 0.6 mL (5.9 mmol) of triethyl amine. The resulting mixture was stirred at 85° C. for 10 hours. The solvent was removed by Genevac® and the resulting crude sample was purified by column chromatography using a gradient of ethyl acetate/hexane as eluent to give 90 mg of the title compound 12. MS: m/z 447. $^1$H NMR (400 MHz, DMSO): δ 7.84-7.67 (m, 3H), 7.61-7.52 (m, 1H), 7.39-7.26 (s, 4H), 7.16-7.02 (m, 4H), 6.57 (s, 1H), 4.04-3.93 (m, 1H), 2.88-2.75 (m, 2H), 2.52-2.35 (m, 5H), 2.32-2.11 (m, 4H), 2.07-1.93 (m, 2H), 1.62-1.50 (m, 2H), 1.42-1.27 (m, 2H).

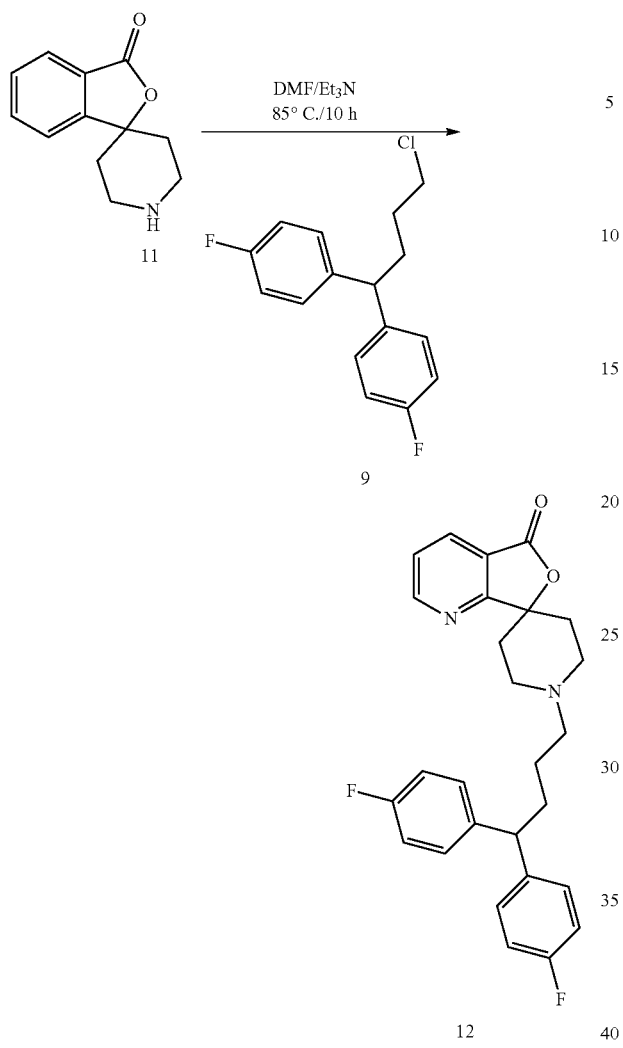

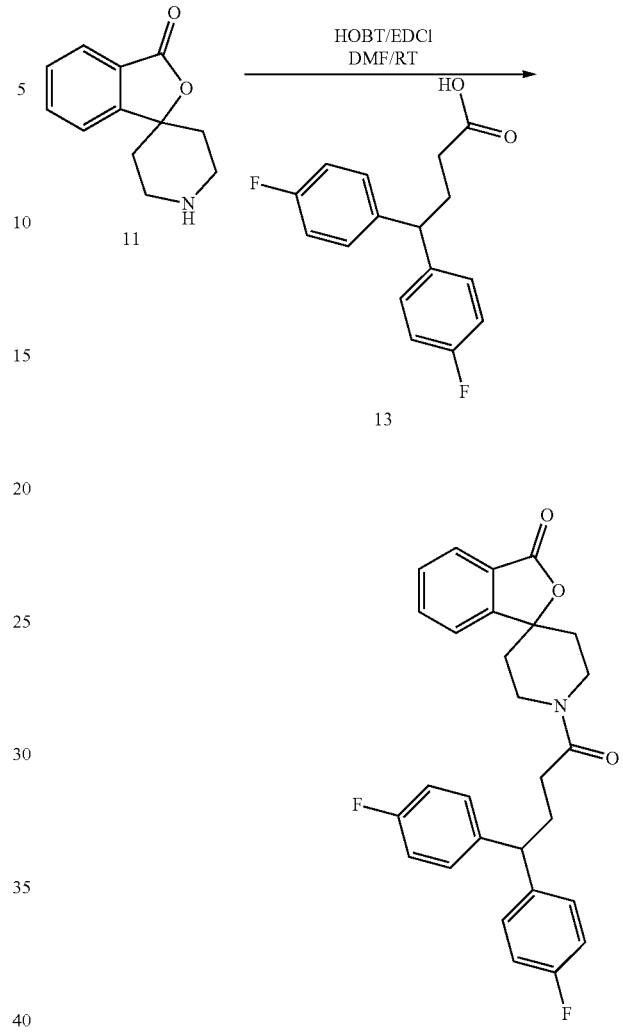

Example 3

1,3-Dihydro-1'-[4,4-bis(4-fluorophenyl)butanoyl]-spiro[isobenzofuran-1,4'-piperidine]-3-one (14)

To a DCM (5.0 mL) solution of 0.1 g (0.42 mmol) of the spirocycle 11 (Arch corporation) at room temperature was added 0.12 g (0.42 mmol) of the acid 13 (prepared as described in Collec. Czech. Chem. Comm. 38, 1973, 3879-3901) followed by 57 mg (0.42 mmol) of 1-hydroxybenzotriazole (HOBT) and 88 mg (0.46 mmol) of N-ethyl-dimethylaminopropyl carbodiimide hydrochloride (EDCI). The resulting reaction mixture was stirred at room temperature for 3 hours and the volatiles were removed by using Genevac®. The resulting crude sample was purified by column chromatography using a gradient of ethyl acetate/hexane as eluent to give 30 mg of the title compound 14. MS: m/z 461. $^1$H NMR (400 MHz, CDCl$_3$): δ 7.93-7.87 (m, 1H), 7.73-7.65 (m, 1H), 7.59-7.51 (m, 1H), 7.35-7.31 (m, 1H), 7.24-7.16 (m, 4H), 7.03-6.92 (m, 4H), 4.81-4.67 (m, 1H), 4.03-3.95 (m, 1H), 3.76-3.68 (m, 1H), 3.54-3.43 (m, 1H), 3.12-3.01 (m, 1H), 2.45-2.23 (m, 4H), 2.08-1.86 (m, 2H).

Example 4

1-(4,4-bis(4-fluorophenyl)butanoyl)-spiro[piperidine-4,5'-cyclopenta[b]pyridine] (15)

To a DMF (5.0 mL) solution of 0.08 g (0.43 mmol) of the spirocycle 8 at room temperature was added 0.12 g (0.43 mmol) of the acid 13 (prepared as described in Collec. Czech. Chem. Comm. 38, 1973, 3879-3901) followed by 0.11 g (0.86 m mol) of 4-dimethylaminopyridine (DMAP) and 0.17 g (0.86 mmol) of EDCI. The resulting reaction mixture was stirred at room temperature for 48 hours and the volatiles were removed by using Genevac®. The resulting crude sample was purified by column chromatography using a gradient of ethyl acetate/hexane as eluent to give 50 mg of the title compound 15. MS: m/z 444. $^1$H NMR (400 MHz, CDCl$_3$): δ 8.35-8.31 (m, 1H), 7.58-7.52 (m, 1H), 7.24-7.17 (m, 4H), 7.16-7.10 (m, 1H), 7.02-6.94 (m, 4H), 6.82-6.74 (m, 2H), 4.57-4.48 (m, 1H), 4.04-3.95 (m, 1H), 3.95-3.87 (m, 1H), 3.40-3.26 (m, 2H), 2.45-2.34 (m, 2H), 2.34-2.25 (m, 2H), 2.04-1.91 (m, 2H), 1.51-1.35 (m, 2H).

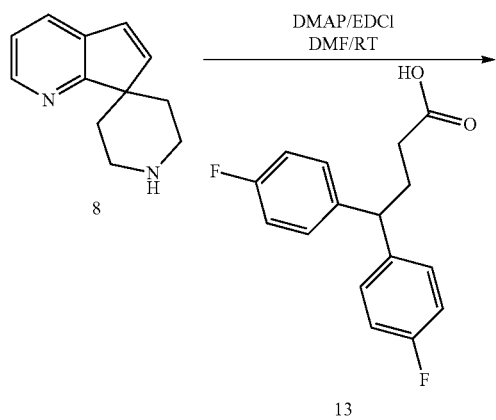

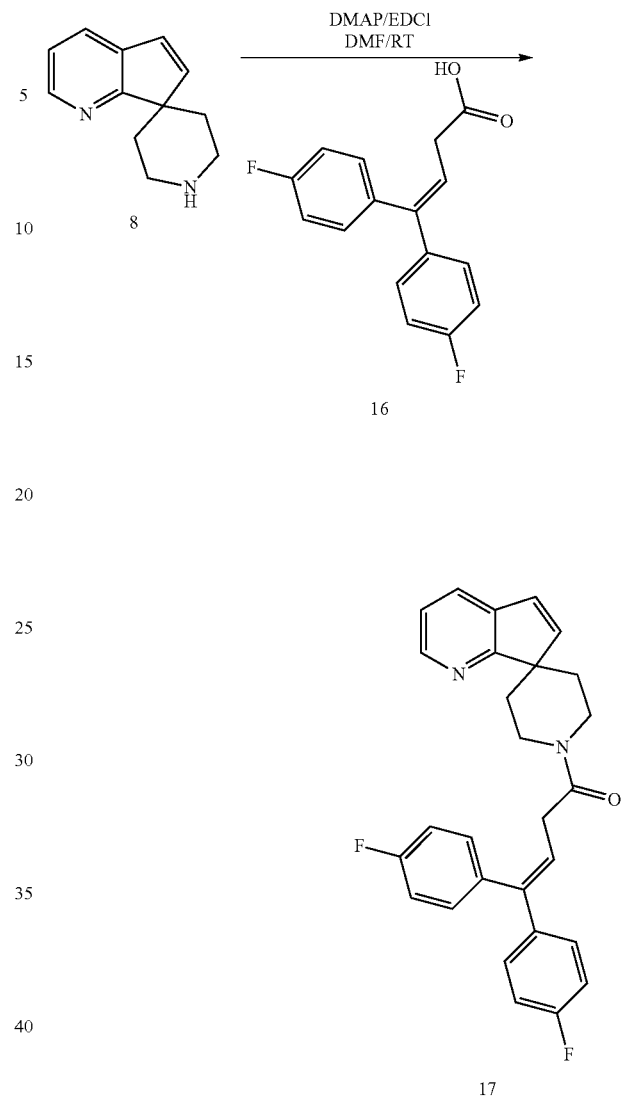

Example 5

1-(4,4-bis(4-fluorophenyl)but-3-enoyl)-spiro[piperidine-4,5'-cyclopenta[b]pyridine] (17)

To a DMF (10 mL) solution of 0.14 g (0.73 mmol) of the spirocycle 8 at room temperature was added 0.2 g (0.73 mmol) of the acid 16 (prepared as described in *Collec. Czech. Chem. Comm.* 38, 1973, 3879-3901) followed by 0.19 g (1.46 mmol) of DMAP and 0.21 g (1.10 mmol) of EDCI. The resulting reaction mixture was stirred at room temperature for 12 hours and the volatiles were removed by using Genevac®. The resulting crude sample was purified by column chromatography using a gradient of ethyl acetate/hexane as eluent to give 0.30 g of the title compound 17. MS: m/z 442. $^1$H NMR (400 MHz, CDCl$_3$): δ 8.35-8.32 (m, 1H), 7.59-7.54 (m, 1H), 7.26-7.05 (m, 7H), 7.01-6.92 (m, 2H), 6.82-6.74 (m, 2H), 6.33-6.26 (m, 1H), 4.56-4.44 (m, 1H), 3.95-3.84 (m, 1H), 3.46-3.28 (m, 2H), 3.27-3.18 (m, 2H), 2.07-1.89 (m, 2H), 1.55-1.37 (m, 2H).

Example 6

1-(4-methoxybenzyl)-spiro[piperidine-4,5'-cyclopenta[b]pyridine] (19)

To a DMF (12.0 mL) solution of 0.20 g (1.1 mmol) of the spirocycle 8 at room temperature was added 0.17 g (1.1 mmol) of the alkyl chloride 18 (Aldrich) and 0.37 mL (2.15 mmol) of diisopropylethylamine (DIEA). The resulting mixture was stirred at 80° C. for 12 hours. The solvent was removed by Genevac® and the resulting crude sample was purified by column chromatography using a gradient of ethyl acetate/hexane as eluent to give 0.1 g the title compound 19. MS: m/z 306. $^1$H NMR (CDCl$_3$): δ 8.38-8.33 (m, 1H), 7.54-7.49 (m, 1H), 7.34-7.28 (m, 2H), 7.12-7.06 (m, 1H), 6.95-6.89 (m, 1H), 6.89-6.83 (m, 2H), 6.76-6.71 (m, 1H), 3.79 (s, 3H), 3.58 (s, 2H), 3.05-2.98 (m, 2H), 2.41-2.29 (m, 4H), 1.35-1.23 (m, 2H).

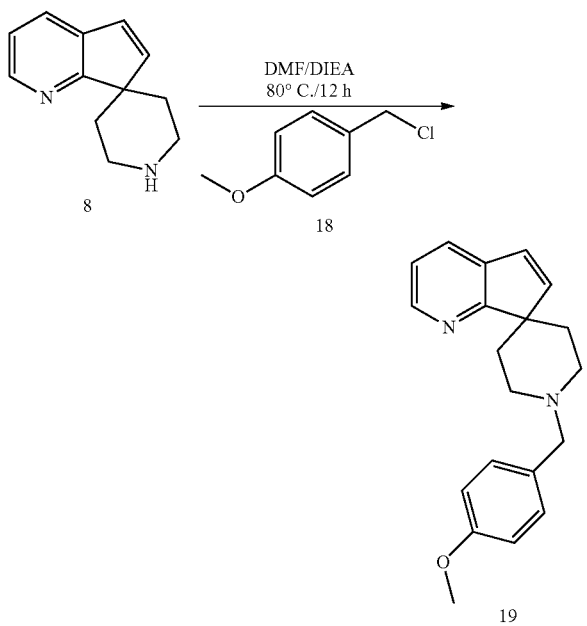

Example 7

1-(4-isopropylbenzoyl)-spiro[piperidine-4,5'-cyclopenta[b]pyridine] (21)

To a DMF (12.0 mL) solution of 0.20 g (1.1 mmol) of the spirocycle 8 at room temperature was added 0.23 g (1.1 mmol) of the alkyl bromide 20 (Aldrich) and 0.37 mL (2.15 mmol) of DIEA. The resulting mixture was stirred at 80° C. for 12 hours. The solvent was removed by Genevac® and the resulting crude sample was purified by column chromatography using a gradient of ethyl acetate/hexane as eluent to give 20 mg of the title compound 21. MS: m/z 318. $^1$H NMR (CDCl$_3$): δ 8.40-8.33 (m, 1H), 7.57-7.50 (m, 1H), 7.36-7.28 (m, 2H), 7.22-7.15 (m, 2H), 7.14-7.07 (m, 1H), 6.97-6.91 (m, 1H), 6.78-6.72 (m, 1H), 3.62 (s, 2H), 3.09-3.00 (m, 2H), 2.96-2.85 (m, 1H), 2.45-2.30 (m, 4H), 1.35-1.20 (m, 8H).

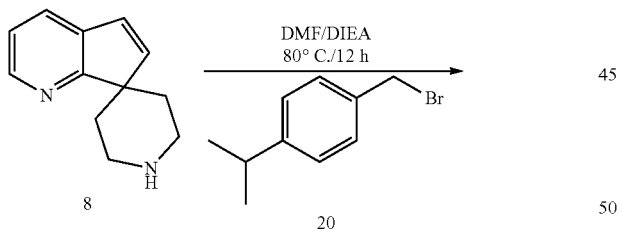

Example 8

1-(4-dimethylaminobenzoyl)-spiro[piperidine-4,5'-cyclopenta[b]pyridine] (23)

To a DCM (12.0 mL) solution of 99 mg (0.54 mmol) of the spirocycle 8 at room temperature was added 98 mg (0.54 mmol) of the acid chloride 22 (Aldrich) and 0.14 ml (0.81 mmol) of DIEA. The resulting mixture was stirred at room temperature for 4 hours. The solvent was removed by Genevac® and the resulting crude sample was purified by column chromatography using a gradient of ethyl acetate/hexane as eluent to give 18.0 mg of the title compound 23. MS: m/z 333. $^1$H NMR (CDCl$_3$): δ 8.39-8.34 (m, 1H), 7.60-7.55 (m, 1H), 7.46-7.41 (m, 2H), 7.18-7.12 (m, 1H), 6.89-6.79 (m, 2H), 6.72-6.65 (m, 2H), 4.42 (s, 2H), 3.55-3.42 (m, 2H), 2.99 (s, 6H), 2.19-2.09 (m, 2H), 1.54-1.44 (m, 2H).

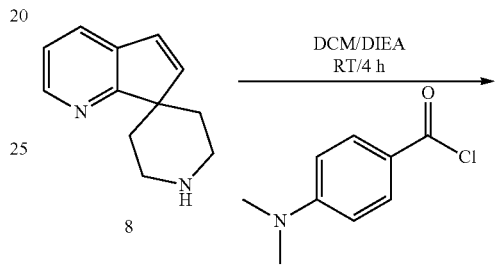

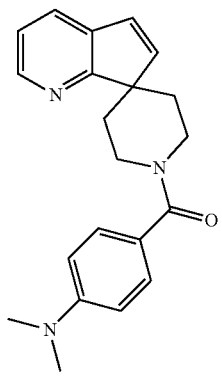

Example 9

1-(4-trifluoromethylphenylsulfonyl)-spiro[piperidine-4,5'-cyclopenta[b]pyridine] (25)

To a DCM (12.0 mL) solution of 99 mg (0.54 mmol) of the spirocycle 8 at room temperature was added 132 mg (0.54 mmol) of the sulfonyl chloride 24 (Aldrich) and 0.14 mL (0.81 mmol) of DIEA. The resulting mixture was stirred at room temperature for 12 hours. The solvent was removed by Genevac® and the resulting crude sample was purified by column chromatography using a gradient of ethyl acetate/hexane as eluent to give 30.0 mg of the title compound 25. MS: m/z 394. $^1$H NMR (CDCl$_3$): δ 8.25-8.19 (m, 1H), 8.02-7.94 (m, 2H), 7.89-7.82 (m, 2H), 7.56-7.50 (m, 1H), 7.14-7.07 (m, 1H), 6.77-6.71 (m, 1H), 6.56-6.50 (m, 1H), 3.92-3.82 (m, 2H), 3.17-3.07 (m, 2H), 2.12-2.01 (m, 2H), 1.72-1.61 (m, 2H).

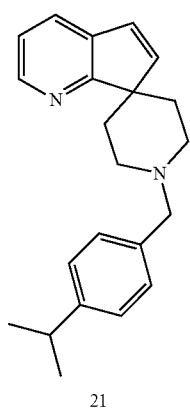

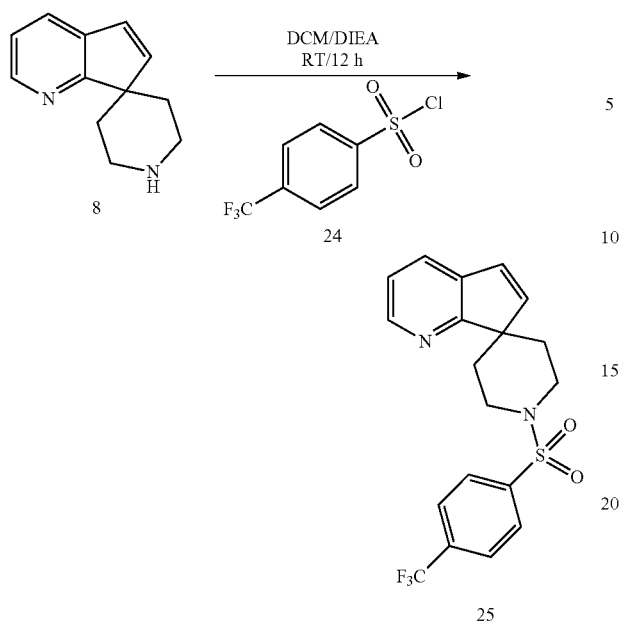

Example 10

1-(4-methyl-2-methylaminopentanoyll)-spiro[piperidine-4,5'-cyclopenta[b]pyridine] (28)

To a DMF (5.0 mL) solution of 0.5 g (2.69 mmol) of the spirocycle 8 at room temperature was added 0.66 g (2.69 mmol) of the acid 26 followed by 0.68 g (5.38 mmol) of DMAP and 1.03 g (5.38 mmol) of EDCI. The resulting reaction mixture was stirred at room temperature for 48 hours and then the volatiles were removed by using Genevac®. The resulting crude sample was purified by column chromatography using a gradient of ethyl acetate/hexane as eluent to give the compound 27 that was dissolved in a solution of 5 mL of trifluoroacetic acid and 15 mL of DCM. The resulting mixture was stirred at room temperature for 2 hours and then the volatiles were removed by using Genevac®. The resulting crude sample was purified by column chromatography using a gradient of ethyl acetate/hexane as eluent to give the title compound 28. MS: m/z 313. $^1$H NMR (CDCl$_3$): δ 8.37-8.32 (m, 1H), 7.61-7.55 (m, 1H), 7.19-7.13 (m, 1H), 6.85-6.73 (m, 2H), 4.65-4.44 (m, 1H), 4.26-4.12 (m, 1H), 3.63-3.37 (m, 3H), 2.46-2.30 (m, 4H), 2.15-1.81 (m, 3H), 1.65-1.29 (m, 4H), 0.99-0.75 (m, 6H).

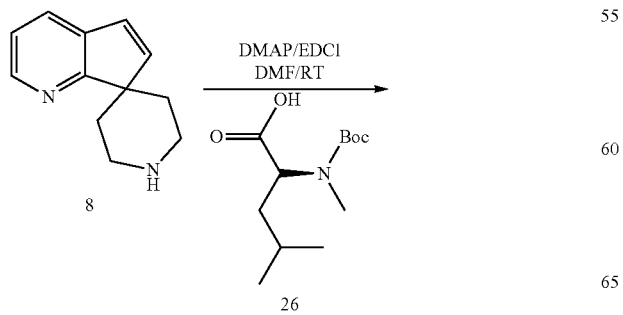

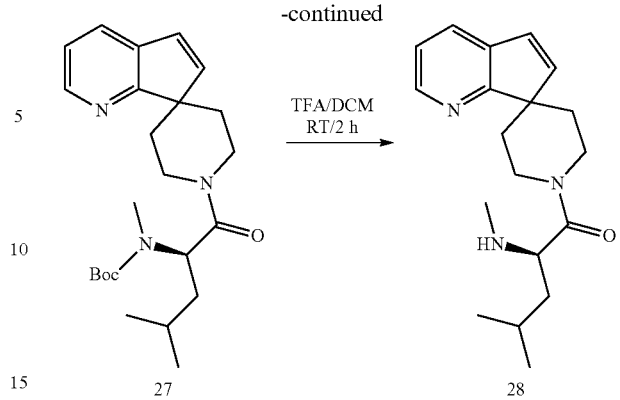

Example 11

1-[4,4-Bis(4-fluorophenyl)butyl]-6',7'-dihydro-spiro[piperidine-4,5'-cyclopenta[b]pyridine] (31)

a) 1-Tert-butoxycarbonyl-6',7'-dihydro-spiro[piperidine-4,5'-cyclopenta[b]pyridine] (29): To the BOC-protected spirocycle 7 (0.35 g, 1.22 mmol) dissolved in 10 mL of methanol under nitrogen atmosphere was added 41 mg of palladium/Charcoal (5%, Aldrich). The nitrogen atmosphere was replaced with hydrogen gas. The resulting mixture was stirred at room temperature for 6 hours and then filtered through a pad of celite. The methanol solution (200 mL) was concentrated and the resulting residue was purified by column chromatography using a gradient of ethyl acetate/hexane as eluent to give 0.35 g of compound 29. MS: m/z 289. $^1$H NMR (CDCl$_3$): δ 8.45-8.36 (m, 1H), 7.56-7.48 (m, 1H), 7.11-6.94 (m, 1H), 4.28-3.99 (m, 2H), 3.19-2.82 (m, 4H), 2.23-1.88 (m, 4H), 1.47 (s, 9H).

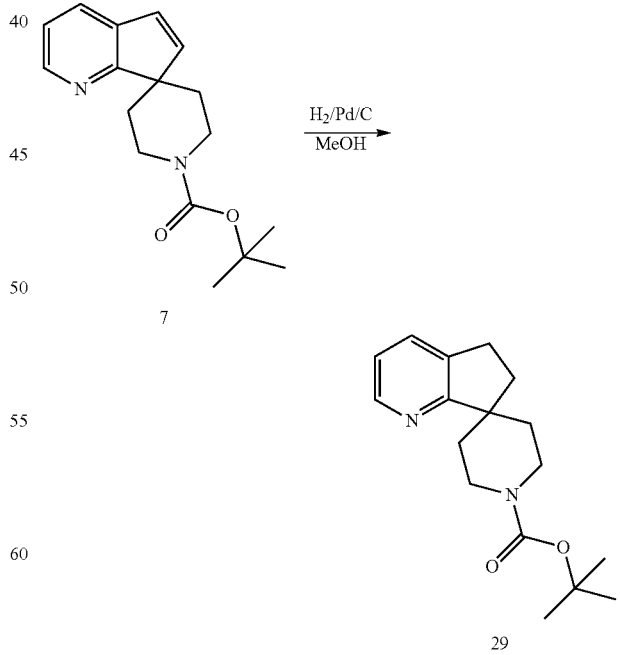

b) 1-[4,4-Bis(4-fluorophenyl)butyl]-6',7'-dihydro-spiro[piperidine-4,5'-cyclopenta[b]pyridine] (31): To 0.32 g (1.10 mmol) of 1-tert-butoxycarbonyl-6',7'-dihydro-spiro[piperidine-4,5'-cyclopenta[b]pyridine] (29) in 3 mL of DCM was added 5 mL of 2M HCl in ether (Aldrich). The resulting mixture was stirred at room temperature for 10 hours and then the volatiles were removed by flushing with nitrogen gas followed by evaporation by rotary evaporator to give the unprotected spirocycle 30 that was redissolved in 6.0 mL of DMF. To the DMF solution of compound 30 at room temperature was added 0.3 mL (2.44 mmol) of triethylamine and 0.34 g (1.22 mmol) of the alkyl chloride 9 (Across). The resulting mixture was stirred at 85° C. for 10 hours. The solvent was removed by Genevac® and the resulting crude sample was purified by column chromatography using a gradient of ethyl acetate/hexane as eluent to give 50 mg of the title compound 31. MS: m/z 432. $^1$H NMR (CDCl$_3$): δ 8.34-8.20 (m, 1H), 7.52-7.43 (m, 1H), 7.17-7.11 (m, 4H), 7.10-7.05 (m, 1H), 6.98-6.91 (m, 4H), 6.85 (s, 1H), 3.91-3.82 (m, 1H), 3.67-3.56 (m, 2H), 3.32 (br s, 2H), 3.09 (br s, 3H), 2.88 (s, 3H), 2.13-1.97 (m, 9H), 1.70 (s, 2H).

Example 12

1-[4,4-bis(4-fluorophenyl)but-3-enoyl]-spiro[piperidine-4,1'-indene] (33)

To a DMF solution of 0.4 g (2.20 mmol) of the spiroindene 32 (Arch corporation) at room temperature was added 0.6 g (2.20 mmol) of the acid 16 (prepared as described in *Collec. Czech. Chem. Comm.* 38, 1973, 3879-3901) followed by 0.3 g (2.20 mmol) of HOBT and 0.46 g (2.4 mmol) of EDCI. The resulting reaction mixture was stirred at room temperature for 6 hours and the volatiles were removed by using Genevac®. The resulting crude sample was purified by column chromatography using a gradient of ethyl acetate/hexane as eluent to give 0.82 g of the title compound 33. MS: m/z 441. $^1$H NMR (CDCl$_3$): δ 7.35-7.31 (m, 1H), 7.45-7.15 (m, 5H), 7.12-7.05 (m, 2H), 7.01-6.94 (m, 2H), 6.83-6.79 (m, 2H), 6.33-6.28 (m, 1H), 4.73-4.62 (m, 1H), 3.76-3.66 (m, 1H), 3.34-3.18 (m, 3H), 3.07-2.95 (m, 1H), 2.06-1.85 (m, 2H), 1.44-1.26 (m, 2H).

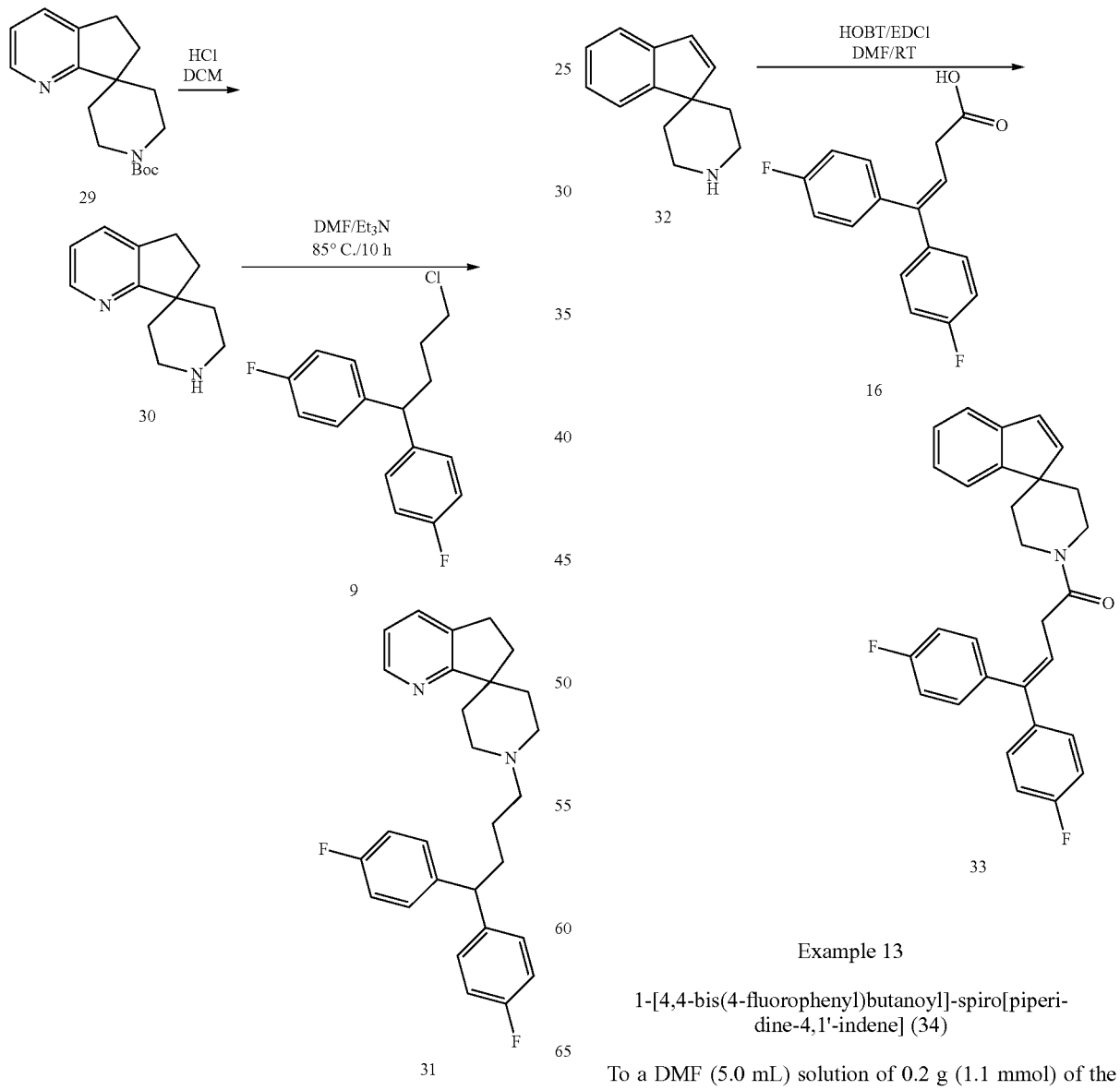

Example 13

1-[4,4-bis(4-fluorophenyl)butanoyl]-spiro[piperidine-4,1'-indene] (34)

To a DMF (5.0 mL) solution of 0.2 g (1.1 mmol) of the spiroindene 32 (Arch corporation) at room temperature was added 0.3 g (1.1 mmol) of the acid 13 (prepared as described in *Collec. Czech. Chem. Comm.* 38, 1973, 3879-3901) followed by 0.15 g (1.1 mmol) of HOBT and 0.21 g (1.1 mmol) of EDCI. The resulting reaction mixture was stirred at room temperature for 6 hours and then the volatiles were removed by using Genevac®. The resulting crude sample was purified by column chromatography using a gradient of ethyl acetate/hexane as eluent to give 0.1 g of the title compound 34. MS: m/z 443. $^1$H NMR (CDCl$_3$): δ 7.35-7.32 (m, 1H), 7.29-7.24 (m, 1H), 7.24-7.18 (m, 5H), 7.02-6.95 (m, 4H), 6.83-6.79 (m, 2H), 4.72-4.62 (m, 1H), 4.05-3.94 (m, 1H), 3.81-3.71 (m, 1H), 3.33-3.21 (m, 1H), 3.05-2.91 (m, 1H), 2.48-2.26 (m, 3H), 2.04-1.82 (m, 2H), 1.43-1.28 (m, 2H).

column chromatography using a gradient of ethyl acetate/hexane as eluent to give 0.5 g of the title compound 35. MS: m/z 445. $^1$H NMR (CDCl$_3$): δ 7.24-7.17 (m, 7H), 7.10-7.07 (m, 1H), 7.02-6.95 (m, 4H), 4.67-4.57 (m, 1H), 4.04-3.93 (m, 1H), 3.68-3.58 (m, 1H), 3.18-3.06 (m, 1H), 2.98-2.85 (m, 2H), 2.82-2.71 (m, 1H), 2.44-2.33 (m, 2H), 2.33-2.24 (m, 2H), 2.14-1.99 (m, 2H), 1.82-1.61 (m, 2H), 1.61-1.48 (m, 3H).

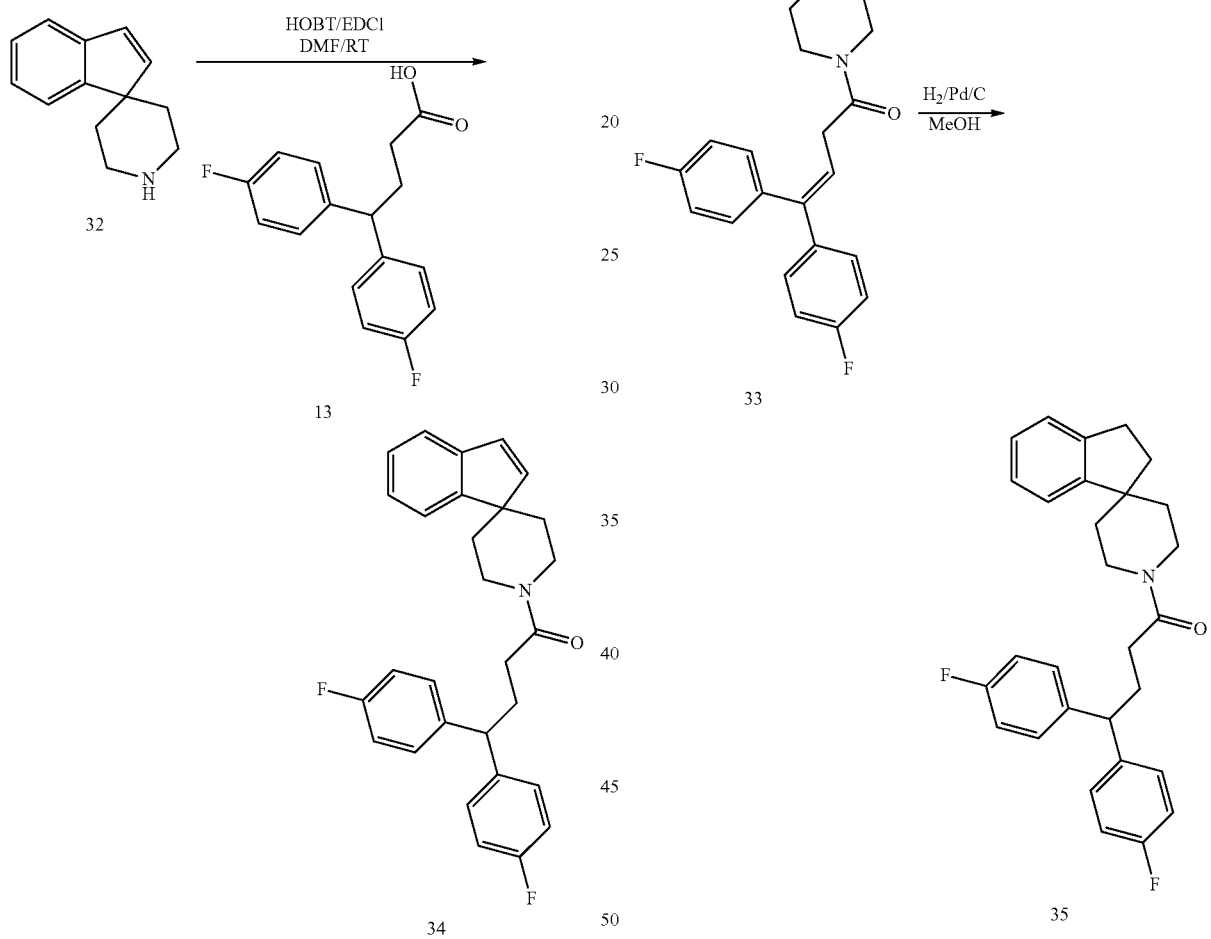

Example 14

1-[4,4-bis(4-fluorophenyl)butanoyl]-spiro[piperidine-4,1'-indane] (35)

0.50 g (1.13 mmol) of 1-[4,4-bis(4-fluorophenyl)but-3-enoyl]-spiro[piperidine-4,1'-indene] (33) was dissolved in 20 mL of methanol under nitrogen atmosphere and then 200 mg of palladium/Charcoal (5%, Aldrich) was added. The nitrogen atmosphere was replaced with hydrogen gas. The resulting mixture was stirred at room temperature for 6 hours and filtered through a pad of celite. The methanol solution (200 mL) was concentrated and the resulting residue purified by

Example 15

1-[4,4-bis(4-fluorophenyl)butanoyl]-6',7'-dihydro-spiro[piperidin-4,5'-cyclopenta[b]pyridine] (36)

To a DMF (5.0 mL) solution of 0.29 g (1.25 mmol) of the compound 30 at room temperature was added 0.2 g (1.25 mmol) of the acid 13 (prepared as described in *Collec. Czech. Chem. Comm.* 38, 1973, 3879-3901) followed by 0.18 g (1.45 mmol) of DMAP and 0.28 g (1.45 mmol) of EDCI. The resulting reaction mixture was stirred at room temperature for 10 hours and then the volatiles were removed by using Genevac®. The resulting crude sample was purified by column chromatography using a gradient of ethyl acetate/hexane as eluent to give 40 mg of the title compound 36. MS: m/z 446. $^1$H NMR (CDCl$_3$): δ 8.39-8.35 (m, 1H), 7.52-7.46 (m, 1H), 7.23-7.14 (m, 4H), 7.09-7.02 (m, 1H), 7.02-6.93 (m, 4H), 4.55-4.45 (m, 1H), 4.02-3.93 (m, 1H), 3.78-3.67 (m, 1H), 3.21-3.08 (m, 1H), 3.05-2.94 (m, 1H), 2.94-2.84 (m, 2H), 2.41-2.31 (m, 2H), 2.30-2.22 (m, 2H), 2.19-2.09 (m, 1H), 2.07-1.86 (m, 3H), 1.55-1.43 (m, 2H).

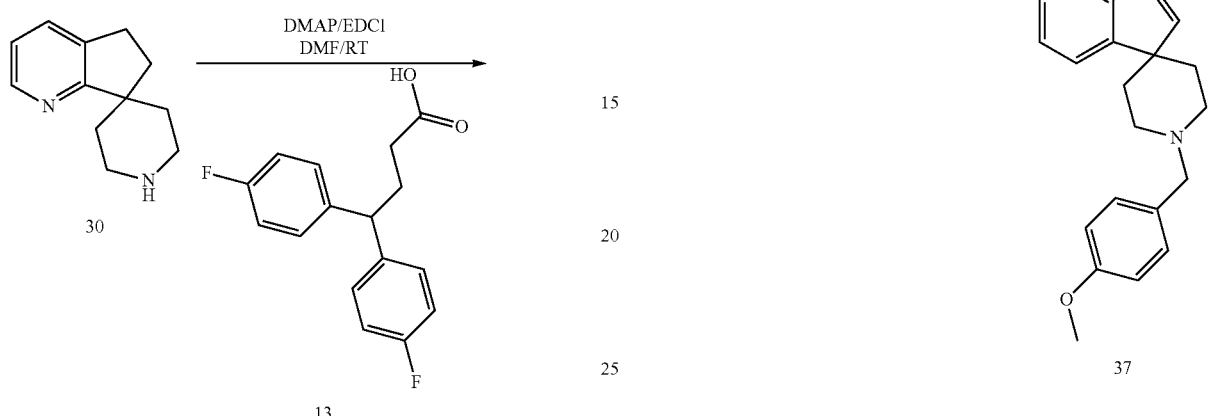

Example 16

1-(4-methoxybenzyl)-spiro[piperidine-4,1'-indene] (37)

To a DMF (5.0 mL) solution of 0.10 g (0.45 mmol) of the spirocycle 32 (Arch Corporation) at room temperature was added 0.085 g (0.54 mmol) of the alkyl chloride 18 (Aldrich) and 0.12 mL (1.1 mmol) of triethylamine. The resulting mixture was stirred at 80° C. for 12 hours. The solvent was removed by Genevac® SS and the resulting crude sample was purified by column chromatography using a gradient of ethyl acetate/hexane as eluent to give 31 mg of the title compound 37. MS: m/z 305. $^1$H NMR (CDCl$_3$): δ 7.40-7.37 (d, 1H), 7.32-7.28 (m, 3H), 7.25-7.16 (m, 2H), 6.91-6.83 (m, 3H), 6.75-6.72 (m, 2H), 3.82 (s, 3H), 3.59 (s, 2H), 3.01-2.94 (m, 2H), 2.39-2.30 (m, 2H), 2.24-2.14 (m, 2H), 1.39-1.30 (m, 2H).

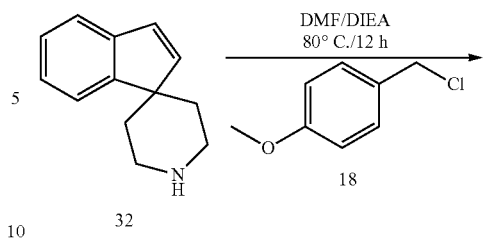

Example 17

1-(4-iso-propylbenzyl)-6',7'-dihydro-spiro[piperidine-4,5'-cyclopenta[b]pyridine] (38)

To a DMF (7.0 mL) solution of 0.30 g (1.33 mmol) of the spirocycle 30 at room temperature was added 0.28 g (1.33 mmol) of the alkyl bromide 20 (Aldrich) and 0.42 mL (2.99 mmol) of triethylamine. The resulting mixture was stirred at 80° C. for 12 hours. The solvent was removed by Genevac® and the resulting crude sample was purified by column chromatography using a gradient of ethyl acetate/hexane as eluent to give 50 mg of the title compound 38. MS: m/z 320. $^1$H NMR (CDCl$_3$): δ 8.43-8.37 (m, 1H), 7.50-7.45 (m, 1H), 7.35-7.27 (m, 2H), 7.20-7.15 (m, 2H), 7.05-7.01 (m, 1H), 3.54 (s, 2H), 2.95-2.82 (m, 5H), 2.27-2.11 (m, 4H), 2.09-2.01 (m, 2H), 1.52-1.41 (m, 2H), 1.29-1.20 (m, 6H).

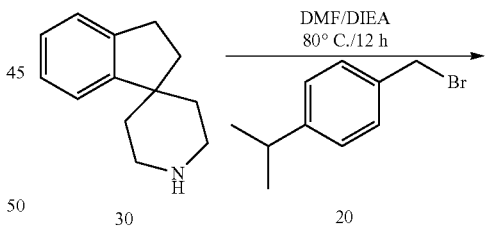

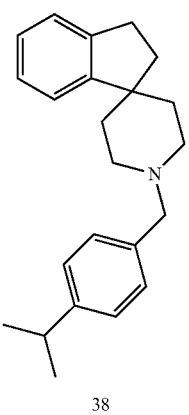

Example 18

1-(3-trifluoromethyl-4-methoxyphenyl)-6',7'-dihydro-spiro[piperidine-4,5'-cyclopenta[b]pyridine] (40)

To a DMF (7.0 mL) solution of 0.30 g (1.33 mmol) of the spirocycle 30 at room temperature was added 0.36 g (1.33 mmol) of the alkyl bromide 39 (Matrix Scientific) and 0.42 mL (2.99 mmol) of triethylamine. The resulting mixture was stirred at 80° C. for 12 hours. The solvent was removed by Genevac® and the resulting crude sample was purified by column chromatography using a gradient of ethyl acetate/hexane as eluent to give 80 mg of the title compound 40. MS: m/z 376. $^1$H NMR (CDCl$_3$): δ 8.43-8.38 (m, 1H), 7.56-7.45 (m, 3H), 7.06-7.00 (m, 1H), 6.98-6.93 (m, 1H), 3.90 (s, 3H), 3.51 (s, 2H), 2.90-2.82 (m, 4H), 2.25-2.10 (m, 4H), 2.09-2.02 (m, 2H), 1.50-1.43 (m, 2H).

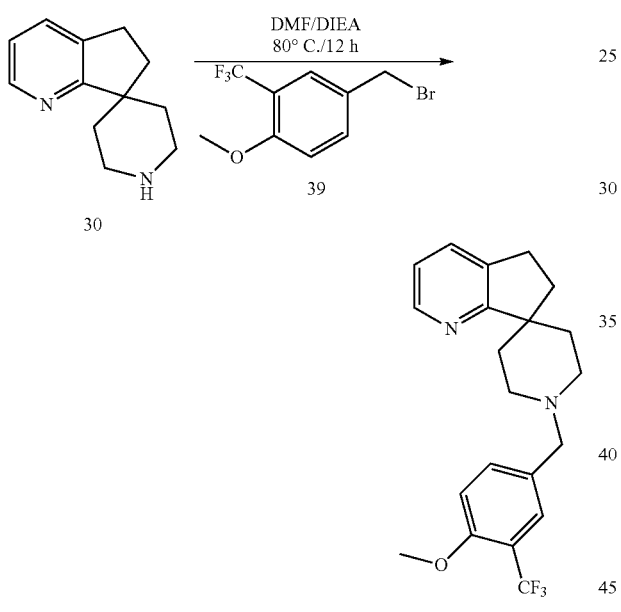

Example 19

1,3-Dihydro-1'-[4,4-bis(4-fluorophenyl)butyl]-spiro[isobenzofuran-1,4'-piperidine (42)

To a DMF (10.0 mL) solution of 0.25 g (1.1 mmol) of the spirocycle 41 (Arch corporation) at room temperature was added 0.31 g (1.1 mmol) of the alkyl chloride 9 (Across) and 0.29 mL (1.65 mmol) of diisopropylethyl amine. The resulting mixture was stirred at 80° C. for 10 hours. The solvent was removed by Genevac® and the resulting crude sample was purified by column chromatography using a gradient of ethyl acetate/hexane as eluent to give 40 mg of the title compound 42. MS: m/z 433. $^1$H NMR (CDCl$_3$): δ 7.34-7.27 (m, 3H), 7.23-7.15 (m, 5H), 7.02-6.95 (m, 4H), 5.06 (s, 2H), 3.97-3.89 (m, 1H), 3.40-3.29 (m, 2H), 3.10-2.99 (m, 2H), 2.99-2.91 (m, 2H), 2.79-2.65 (m, 2H), 2.16-2.05 (m, 2H), 1.92-1.77 (m, 4H).

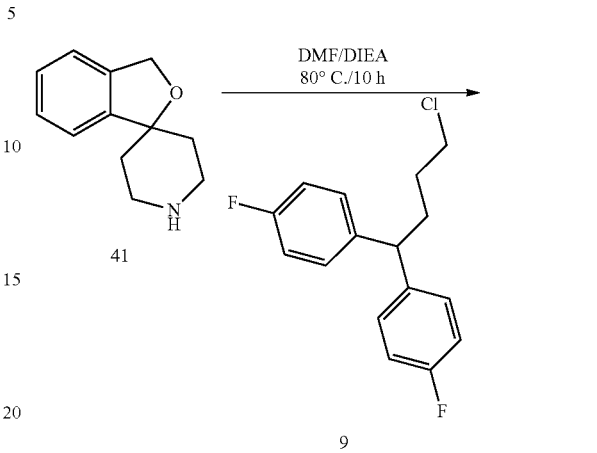

Example 20

2-Benzyl-2,3-dihydro-1'-[4,4-bis(4-fluorophenyl)butyl]-spiro[isoindole-1,4'-piperidine]-3-one (51)

a) To a solution of 1.1 g (5.6 mmol) of 1-tert-butoxycarbonyl-4-piperidone 43 in 20 mL of toluene at room temperature was added 0.6 g (5.57 mmol) of benzyl amine 44. The resulting mixture was stirred at 80° C. for 3 hours and then the volatiles removed. The resulting crude sample was redissolved in 30 mL of toluene and acid chloride 46 (1.13 g, 4.24 mmol) was added to the mixture followed by 0.96 mL (6.9 mmol) of triethylamine. The resulting reaction mixture was stirred at 80° C. for 12 hours. The mixture was cooled to room temperature and diluted with 100 mL of ethyl acetate. This solution was washed with aqueous NaHCO$_3$. The layers were separated and the organic layer was dried (Na$_2$SO$_4$) and then concentrated to give a crude sample that was purified by column chromatography using a gradient of ethyl acetate/hexane as eluent to give 1.6 g of the compound 47.

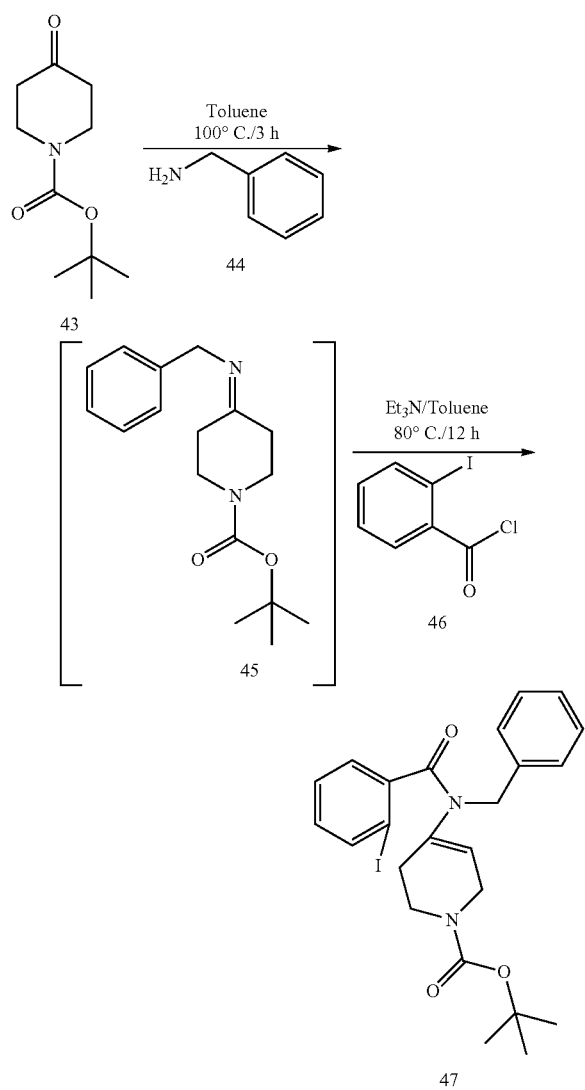

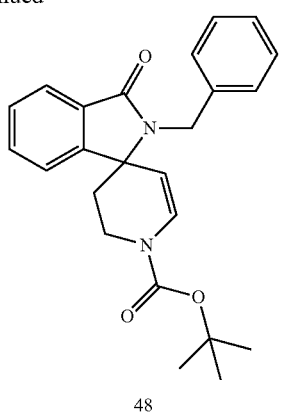

c) To a stirred solution of compound 48 (1.1 g, 2.82 mmol) in MeOH (40 mL) at room temperature under nitrogen was added 0.4 g of Pd(OH)$_2$ on Carbon. The nitrogen gas was replaced with hydrogen gas and the resulting reaction mixture was stirred at room temperature for 20 hours. The solids were filtered over a pad of celite and the methanol solution was concentrated to give 0.8 g of compound 49 that was redissolved in a solution of 10 mL of trifluoroacetic acid and 30 mL of DCM. The resulting solution was stirred at room temperature for 1 hour and the volatiles were removed by using Genevac®. The resulting crude sample was purified by column chromatography using a gradient of ethyl acetate/hexane as eluent to give 0.6 g of compound 50.

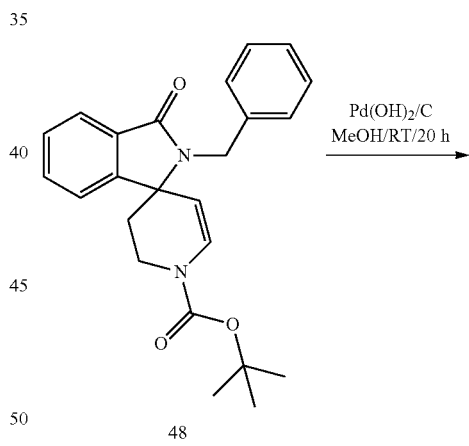

b) A 3.0 g portion of compound 47 was dissolved in 10 mL of acetonitrile and 260 mg (1.16 mmol) of Pd(OAc)$_2$, 243 mg (0.93 mmol) of PPh$_3$, 1.28 g (9.7 mmol) K$_2$CO$_3$, and 1.86 g (5.79 mmol) were added to it. The mixture was stirred at 80° C. for 12 hours and then the volatiles were removed by using Genevac®. The resulting crude sample was purified by column chromatography using a gradient of ethyl acetate/hexane as eluent to give 1.1 g of compound 48.

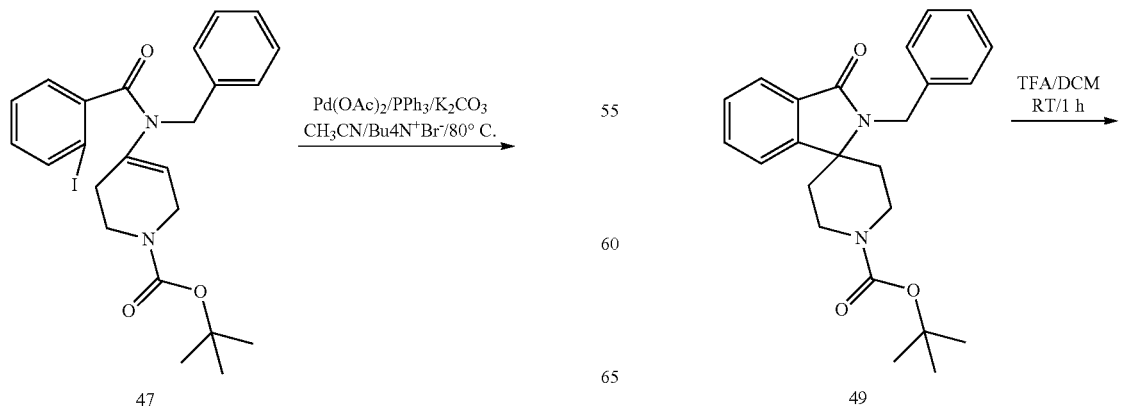

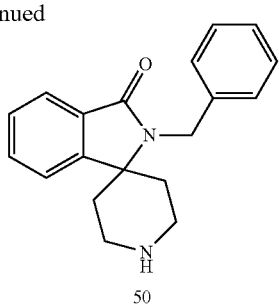

50 d) 2-Benzyl-2,3-dihydro-1'-[4,4-bis(4-fluorophenyl)butyl]spiro[isoindole-1,4'-piperidine]-3-one (51): To a DMF (10.0 mL) solution of 0.61 g (2.1 mmol) of the spirocycle 50 at room temperature was added 0.6 g (2.1 mmol) of the alkyl chloride 9 (Across) and 0.5 mL (2.6 mmol) of diisopropylethyl amine. The resulting mixture was stirred at 85° C. for 10 hours. The solvent was removed by Genevac® and the resulting crude sample was purified by column chromatography using a gradient of ethyl acetate/hexane as eluent to give 126 mg of the title compound 51. MS: m/z 536. $^1$H NMR (CDCl$_3$): δ 7.99-7.93 (m, 1H), 7.85-7.80 (m, 1H), 7.55-7.48 (m, 2H), 7.32-7.19 (m, 5H), 7.19-7.12 (m, 4H), 7.00-6.92 (m, 4H), 4.80 (s, 2H), 3.92-3.83 (m, 1H), 2.89-2.78 (m, 2H), 2.65-2.54 (m, 2H), 2.54-2.45 (m, 2H), 2.28-2.14 (m, 2H), 2.08-1.97 (m, 2H), 1.53-1.35 (m, 4H).

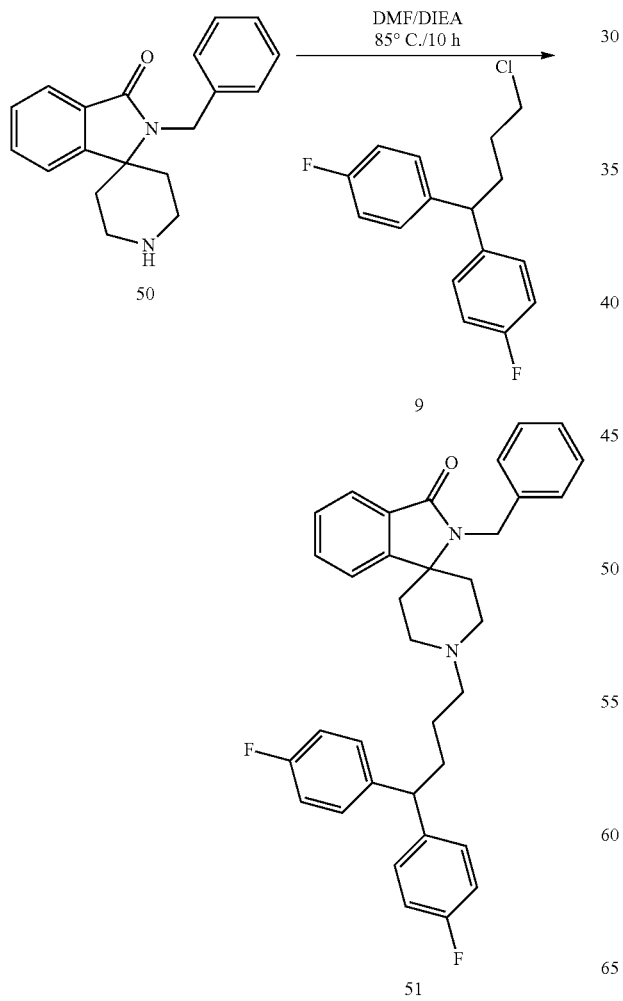

1-Benzyl-2,3-dihydro-1'-[4,4-bis(4-fluorophenyl)butyl]-spiro[indole-3,4'-piperidine]-2-one can be prepared according to the above described procedure using 1-benzyl-2,3-dihydro-1'-tert-butoxycarbonyl-spiro[indole-3,4'-piperidine]-2-one (57) prepared in Example 21, step c, as a starting material. LC: 97.4%. MS: m/z=537.3, 538.2 (M+H). $^1$H NMR (CDCl$_3$): δ 7.37-7.33 (m, 1H), 7.33-7.22 (m, 5H), 7.21-7.12 (m, 5H), 7.03-6.94 (m, 5H), 6.73-6.69 (m, 1H), 4.92-4.85 (s, 1H), 3.94-3.86 (m, 1H), 2.97-2.85 (m, 2H), 2.72-2.61 (m, 2H), 2.58-2.49 (m, 2H), 2.11-2.01 (m, 2H), 2.01-1.84 (m, 4H), 1.58-1.47 (m, 2H).

Example 21

2,3-Dihydro-1'-[4,4-bis(4-fluorophenyl)butyl]-spiro[indole-3,4'-piperidine]-2-one (60)

a) To a solution of 10.0 g (58.13 mmol) of 2-bromoaniline 52 in 80 mL of 1,2-dichloroethane at room temperature was added 5.8 mL (58.13 mmol) of benzaldehyde 53. The resulting mixture was stirred at room temperature for 10 hours. After this period, the reaction mixture was diluted with 300 mL DCM and washed with saturated aqueous NaHCO$_3$. The layers were separated and the organic layer was dried (Na$_2$SO$_4$) and concentrated to give a crude sample that was purified by column chromatography using a gradient of ethyl acetate/hexane as eluent to give 6.2 g of compound 54.

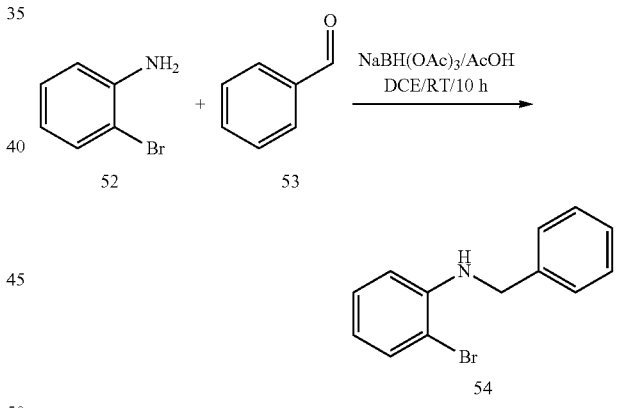

b) To a stirred solution of the acid 55 (6.4 g, 27.9 mmol) and pyridine (5.5 mL, 68.06 mmol) in DCM (36 mL) at room temperature was added 2.6 mL (35.1 mmol) of SOCl$_2$. The resulting mixture was stirred at room temperature for 1 hour and a mixture of compound 54 (4.0 g, 15.26 mmol), triethylamine (7.5 mL, 53.87 mmol), and DMAP (187 mg, 1.53 mmol) in DCM (36 mL) were added to it. The reaction mixture was stirred at room temperature for 12 hours. After this period, the reaction mixture was diluted with 300 mL of DCM and washed with saturated aqueous NaHCO$_3$. The layers were separated and the organic layer was dried (Na$_2$SO$_4$) and concentrated to give a crude sample that was purified by column chromatography using a gradient of ethyl acetate/hexane as eluent to give 3.9 g of compound 56.

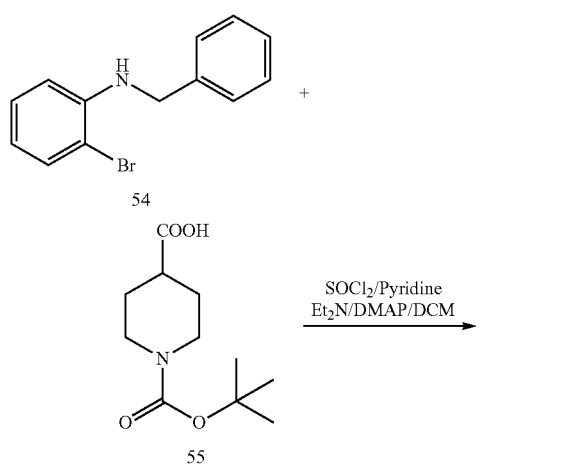

54

55

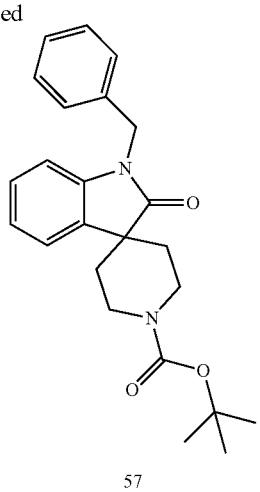

57 d) 2,3-Dihydro-1'-tert-butoxycarbonyl-spiro[indole-3,4'-piperidine]-2-one (58): To a 30 mL of $NH_3$ that is condensed at −78° C. was added 300 mg of sodium metal. The mixture was stirred at −78° C. for 5 minutes and a solution of compound 57 (1.1 g, 2.8 mmol) in 6 mL of THF was added to the mixture. The resulting reaction mixture was stirred for 1 hour and the reaction was quenched with 10 mL of methanol. The excess $NH_3$ was evaporated at room temperature and then the volatiles were removed by using Genevac®. The resulting crude sample was purified by column chromatography using a gradient of ethyl acetate/hexane as eluent to give 0.8 g of compound 58.

56 c) 1-Benzyl-2,3-dihydro-1'-tert-butoxycarbonyl-spiro[indole-3,4'piperidine]-2-one (57): A 2.5 g (5.28 mmol) portion of compound 56, NaOtBu (761 mg, 7.92 mmol), and 2,2'-bis(diphenylphosphino)-1,1'-binaphthyl (BINAP) (Aldrich) (246 mg, 0.395 mmol) was dissolved in 10 mL of dioxane under nitrogen. The reaction mixture was stirred at room temperature for 5 minutes and then $Pd_2(dba)_3$ (242 mg, 0.264 mmol) was added to the mixture. The reaction mixture stirred at 95° C. for 5 hours and then the volatiles were removed by using Genevac®. The resulting crude sample was purified by column chromatography using a gradient of ethyl acetate/hexane as eluent to give 1.1 g of compound 57.

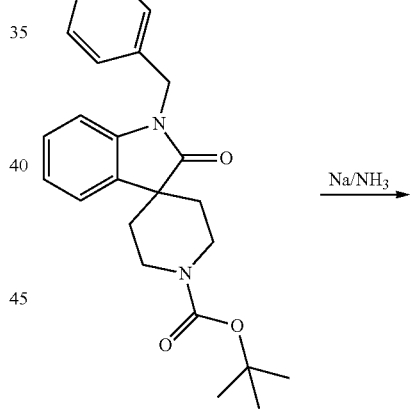

57

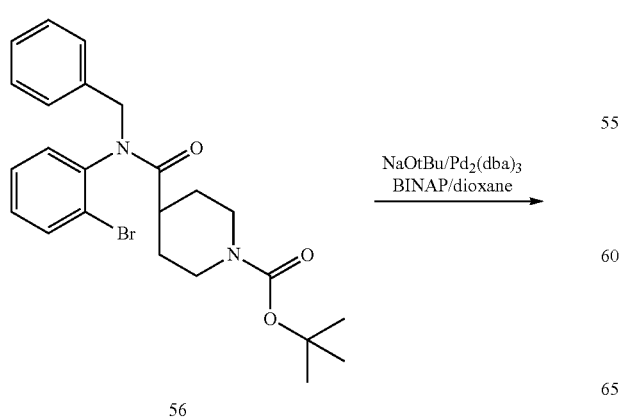

56

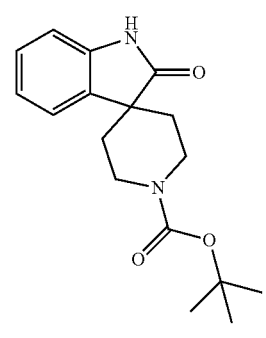

58 e) 2,3-Dihydro-spiro[indole-3,4'-piperidine]-2-one (59): A 1.1 g (2.8 mmol) portion of compound 58 was treated with 50 mL of 2 N HCl in ether (Aldrich) at room temperature for 6 hours. After this period, the volatiles were removed by rotary evaporator to give 0.7 g of compound 59 as a white solid.

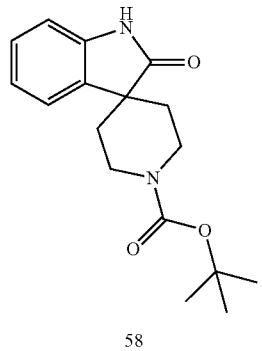

f) 2,3-Dihydro-1'-[4,4-bis(4-fluorophenyl)butyl]-spiro[indole-3,4'-piperidine]-2-one (60): To a DMF (10.0 mL) solution of 0.3 g (1.63 mmol) of the spirocycle 59 at room temperature was added 0.5 g (1.63 mmol) of the alkyl chloride 9 (Across) and 0.7 mL (4 mmol) of diisopropylethyl amine. The resulting mixture was stirred at 85° C. for 10 hours. The solvent was removed by Genevac® and the resulting crude sample was purified by column chromatography using a gradient of ethyl acetate/hexane as eluent to give 126 mg of the title compound 60. MS: m/z 447. $^1$H NMR (CDCl$_3$): δ 7.37-7.28 (m, 2H), 7.24-7.13 (m, 4H), 7.06-6.87 (m, 4H), 6.87-6.82 (m, 1H), 3.92-3.88 (m, 1H), 2.89-2.79 (m, 2H), 2.69-2.59 (m, 2H), 2.56-2.49 (m, 2H), 2.10-2.00 (m, 2H), 1.98-1.79 (m, 3H), 1.63-1.44 (m, 2H).

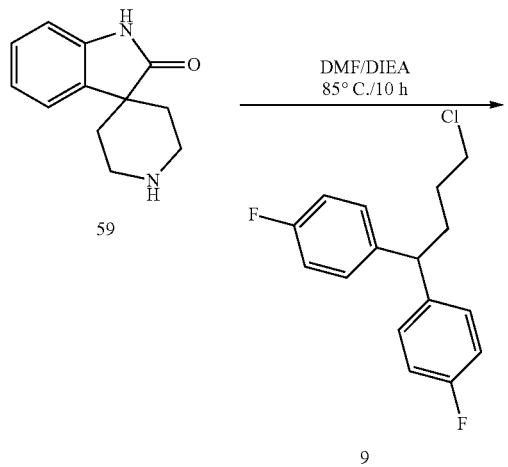

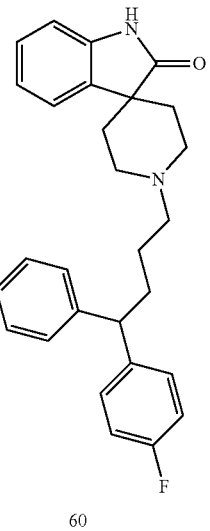

2,3-Dihydro-1'-[4,4-bis(4-fluorophenyl)butyl]-spiro[isoindole-1,4'-piperidine]-3-one can be prepared according to the above described procedure using 2-benzyl-2,3-dihydro-1'-tert-butoxycarbonyl-spiro[isoindole-1,4'-piperidine]-3-one (48) prepared in Example 20 as a starting material. LC: 100%. MS: m/z=447.3, 448.2 (M+H). $^1$H NMR (CDCl$_3$): δ 7.34-7.79 (m, 1H), 7.61-7.54 (m, 1H), 7.50-7.38 (m, 2H), 7.22-7.14 (m, 4H), 7.02-6.94 (m, 4H), 6.78-6.72 (s, 1H), 3.93-3.84 (m, 1H), 3.04-2.91 (m, 2H), 2.50-2.39 (m, 2H), 2.29-2.15 (m, 2H), 2.15-1.99 (m, 4H), 1.61-1.52 (m, 2H), 1.53-1.45 (m, 2H).

Example 22

1,3-Dihydro-1'-{3-[N,N-bis(4-fluorophenyl)amino]propyl}-spiro[isobenzofuran-1,4'-piperidine]-3-one (68)

a) A 250-mL round bottom flask was charged with Pd$_2$(dba)$_3$ (100 mg), a ligand (300 mg; Aldrich), and Cs$_2$CO$_3$ (2.0 g), followed by tert-butanol (25 mL) and 1,4-dioxane (50 mL). After the mixture was stirred for 5 minutes, 4-fluoroaniline (61) (1.0 g, 4.5 mmol) and compound 62 (0.6 g, 5.4 mmol) were added to the flask. The flask was then flushed with argon, heated, and stirred at 100° C. for 15 hours. When the reaction was complete, the flask was removed from the heat and allowed to cool to ambient temperature. The residue was concentrated under vacuum and purified by flash silica column chromatography isocratically (ethyl acetate/hexanes, 1:9) to give compound 63 as a yellow oil (0.7 g, yield 70%).

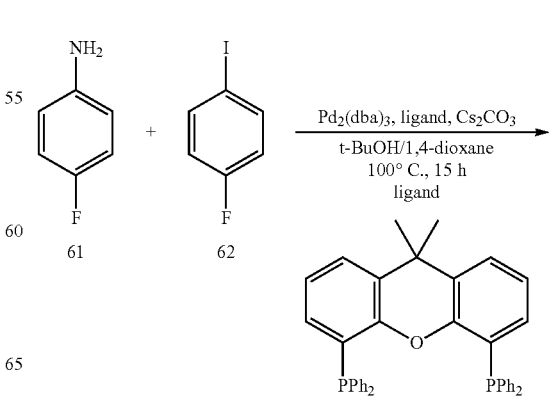

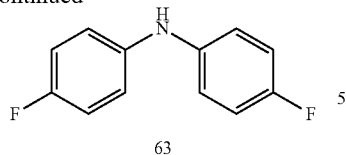

b) A 50-mL round bottom flask was charged with compound 63 (0.4 g, 1.95 mmol) and compound 64 (0.6 mL, 2.3 mmol; Aldrich) in DMF (6 mL). The mixture was stirred at ambient temperature for 5 minutes, and then NaH (60 mg, 60% in mineral oil) was added. The reaction mixture was heated to 70° C. for 4 hours. When the reaction was complete, the mixture was quenched with water (20 mL), transferred to an extraction funnel, and extracted with ethyl acetate (2×20 mL). The organic layers were combined and dried over $Na_2SO_4$ and concentrated in vacuo. The residue was purified by flash silica column chromatography isocratically (ethyl acetate/hexanes, 3:100) to give compound 65 as a colorless oil (0.5 g, yield 98%).

c) In a 50 mL vial, compound 65 was re-dissolved in acetonitrile (10 mL) at ambient temperature, and one mL of HF (48% aq.) was added. The vial was then shaken at ambient temperature for 2 hours. When the reaction was complete, the reaction mixture was neutralized with 2N aq. NaOH and extracted with ethyl acetate (2×10 mL). The solvents were removed in vacuuo to leave the product 66 as a colorless oil. The product was used in the next step without further purification.

d) In a 50-mL vial, the crude product 66 (0.3 g, 1.1 mmol) was dissolved in DCM (5 mL) and triethylamine (TEA) (0.2 mL). $MeSO_2Cl$ (0.12 mL, 1.5 mmol) was added to the reaction mixture and the mixture was shaken at ambient temperature for 12 hours. When the reaction was complete, the product was purified by flash silica column chromatography isocratically with ethyl acetate/hexanes (1:4), to afford compound 67 as a colorless oil (0.35 g, yield 92%).

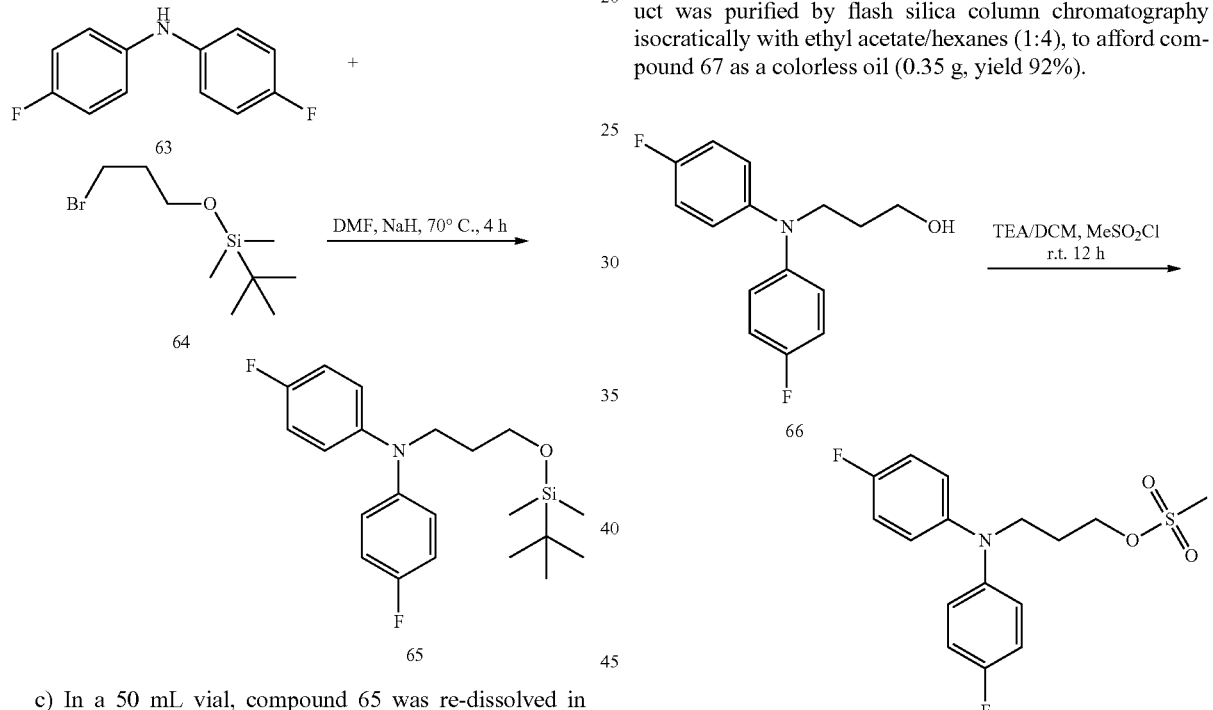

e) In a 20 mL sealed vial, compound 67 (50 mg, 0.15 mmol) was dissolved in 2 mL of acetonitrile, followed by addition of compound 11 (50 mg, 0.21 mmol) as its HCl salt, $K_2CO_3$ (30 mg, 0.21 mmol), and $Et_3N$ (0.1 mL, 0.7 mmol). The mixture was heated to reflux for 6 hours. When the reaction was complete, the residue was concentrated to dryness under vacuum. The desired compound was partitioned with 5 mL of water and ethyl acetate (2×10 mL). The organic solution was dried over $MgSO_4$, and concentrated under vacuum. The crude residue was purified by flash silica column chromatography with an isocratic eluent of DCM/MeOH (98:2), to afford the title compound 68 as a white solid (40 mg, yield 60%). LC: 100%. MS: m/z=449.2, 450.3 (M+H). $^1$H NMR ($CDCl_3$): δ 7.92-7.85 (m, 1H), 7.72-7.64 (m, 1H), 7.57-7.48 (m, 1H), 7.45-7.39 (m, 1H), 7.28-6.82 (m, 8H), 3.80-3.63 (m, 2H), 2.95-2.85 (m, 2H), 2.58-2.44 (m, 4H), 2.26-2.13 (m, 2H), 1.93-1.79 (m, 2H), 1.78-1.66 (m, 2H).

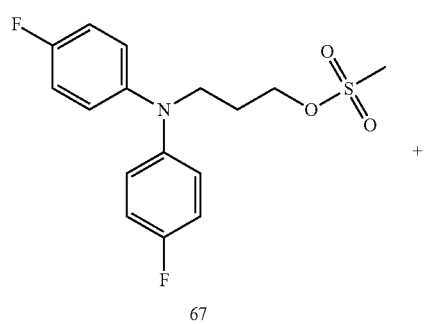

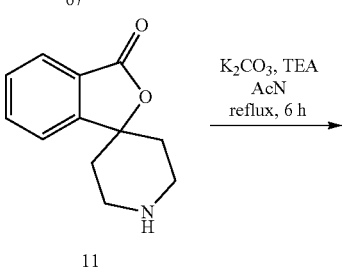

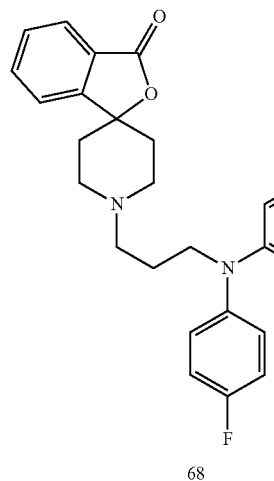

Example 23

1,3-Dihydro-1'-[N,N,-bis(4-fluorophenyl)aminocarbonylmethyl]-spiro[isobenzofuran-1,4'-piperidine]-3-one (71)

a) A 50-mL vial was charged with compound 63 (0.2 g, 0.98 mmol) and compound 69 (110 mg, 0.98 mmol; Aldrich) in 2 mL of toluene and the mixture was heated to 80° C. for 3 hours with stirring. When the reaction was complete, the resulting compound was purified on a bed of silica gel isocratically with EtOAc/hexanes (2:10) to afford compound 70 as a white solid (240 mg, yield 74%).

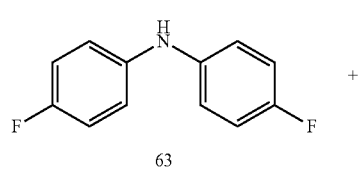

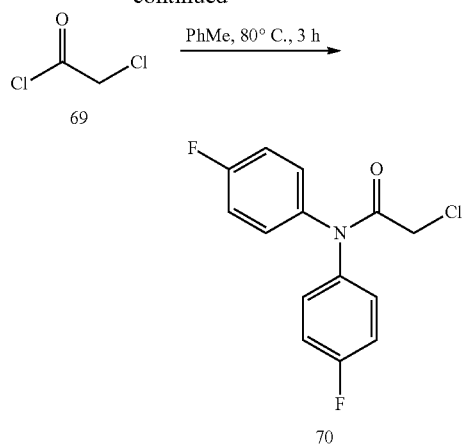

b) A 50-mL vial was charged with compound 70 (40 mg, 0.14 mmol) and compound 11 (34 mg, 0.14 mmol, Arch corporation) in 2 mL of AcN and the mixture was heated to 80° C. for 4 hours with stirring. When the reaction was complete, the resulting compound was purified on a bed of silica gel isocratically with EtOAc/Hexanes (2:10) to afford the title compound 71 as a white solid (20 mg, yield 32%). LC: 100%. MS: m/z=449.2, 450.1 (M+H). $^1$H NMR (CDCl$_3$): δ 7.90-7.84 (m, 1H), 7.71-7.64 (m, 1H), 7.56-7.49 (m, 1H), 7.45-7.38 (m, 1H), 7.36-6.97 (m, 8H), 3.26-3.18 (m, 2H), 3.11-3.00 (m, 2H), 2.66-2.54 (m, 2H), 2.41-2.27 (m, 2H), 1.77-1.63 (m, 2H).

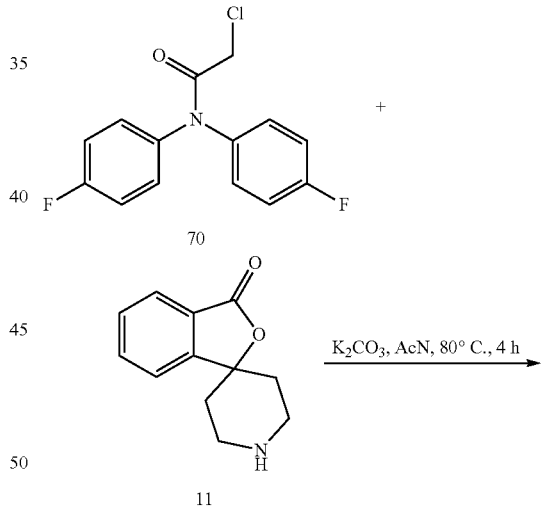

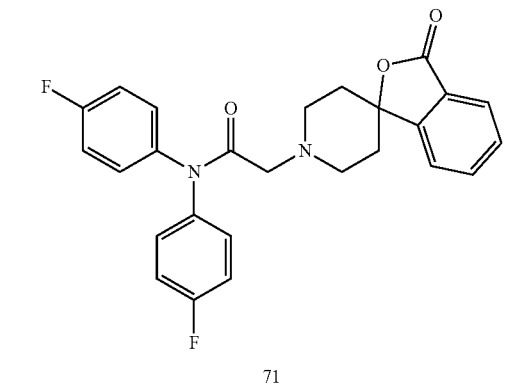

Example 24

1,3-Dihydro-1'-{2-[N,N,-bis(4-fluorophenyl)aminocarbonyl]ethan-1-oyl}-spiro[isobenzofuran-1,4'-piperidine]-3-one (75)

a) A 50-mL vial was charged with compound 63 (0.3 g, 1.46 mmol) and compound 72 (0.2 g, 1.46 mmol; Aldrich) in 1 mL of toluene and the mixture was heated to 80° C. for 3 hours with stirring. When the reaction was complete, the resulting compound was purified on a bed of silica gel isocratically with EtOAc/hexanes (3:7) to afford compound 70 as a colorless oil (0.4 g, yield 89%).

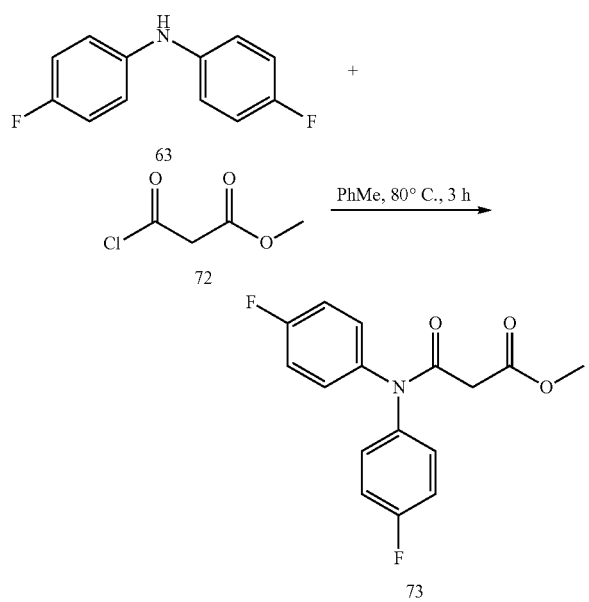

b) A 20-mL vial was charged with compound 73 (0.3 g, 0.98 mmol) and dissolved in 4 mL of MeOH. One mL of aq. LiOH (1N aq., 1 mmol) was added to the mixture and was allowed to react at ambient temperature for 5 hours with shaking. When the reaction was complete, the reaction was quenched with 5 mL of 2N aq. HCl and the compound was extracted with 2×5 mL of DCM. The organic layer was dried over Na$_2$SO$_4$, concentrated under vacuum, and was purified on a bed of silica gel isocratically with EtOAc/DCM (1:1) to afford compound 74 as a colorless oil (0.25 g, yield 87%).

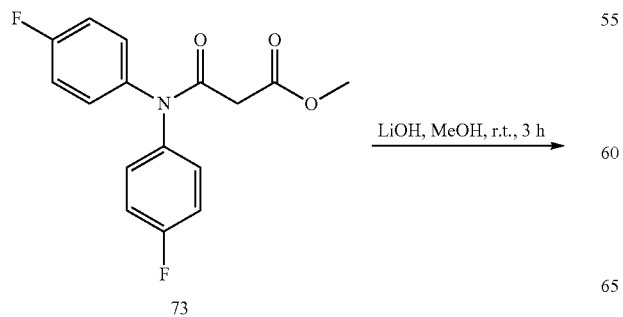

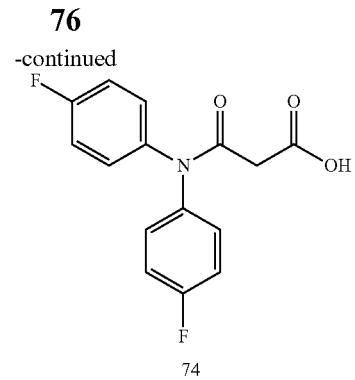

c) A 20-mL vial was charged with compound 74 (0.1 g, 0.34 mmol), compound 11 (82 mg, 0.34 mmol), DMAP (10 mg), HOBt (20 mg), and TEA (0.2 mL), and dissolved in 4 mL of DCM. The mixture was cooled to 0° C. and diisopropyl azodicarboxylate (DIC) (0.05 mL, 0.34 mmol) was added. The reaction mixture was shaken for 16 hours while warming to room temperature. When the reaction was complete, the residue was purified on a bed of silica gel isocratically with EtOAc/DCM (1:1) to afford the title compound 75 as a colorless oil (50 mg, yield 32%). LC: 100%. MS: m/z=477.1, 478.1 (M+H). $^1$H NMR (CDCl$_3$): δ 7.93-7.85 (m, 1H), 7.73-7.64 (m, 1H), 7.59-7.51 (m, 1H), 7.50-7.21 (m, 5H), 7.21-6.99 (m, 4H), 4.79-4.65 (m, 1H), 3.91-3.75 (m, 1H), 3.66-3.52 (m, 2H), 3.51-3.40 (m, 1H), 3.16-3.02 (m, 1H), 2.30-2.14 (m, 1H), 2.15-2.01 (m, 1H), 1.78-1.64 (m, 2H).

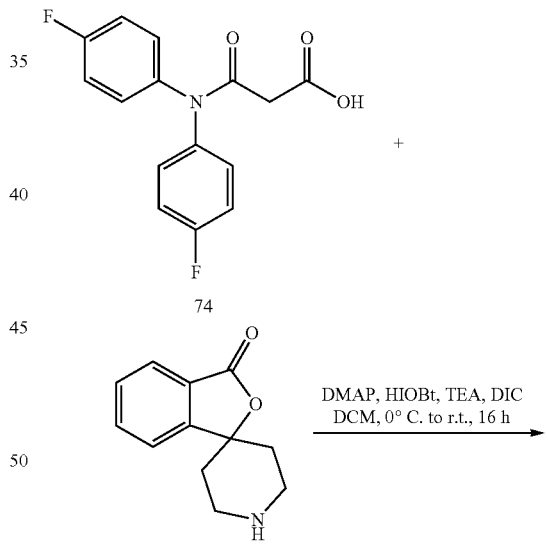

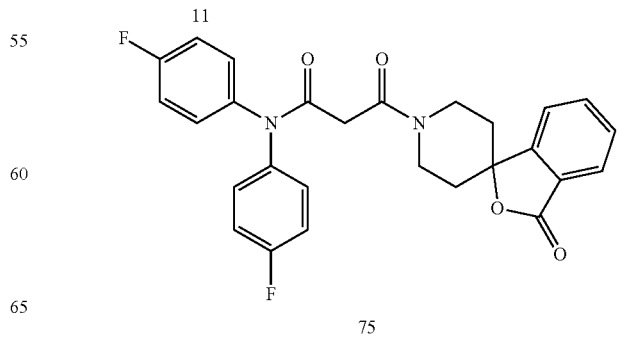

Example 25

Compounds of the invention have been tested in the calcium mobilization and/or assay for N-type calcium channel blocking activity, which are described in detail above. Some compounds described have also been tested in the calcium mobilization and/or electrophysiological assays for L-type calcium channel blocking activity, which is described in detail above. Representative values are presented in TABLE 2.

TABLE 2

Evaluation of the tested compounds as N-type calcium channel (NTCC) blockers and L-type calcium channel (LTCC) blockers after a calcium mobilization in vitro assay

| COMPOUND | NTCC IC$_{50}$ (µM) | LTCC IC$_{50}$ (µM) |
|---|---|---|
| 1,3-dihydro-1'-[4,4-bis(4-fluorophenyl)butyl]-spiro[isobenzofuran-1,4'-piperidine]-3-one (12) | 0.46 | 3.95 |
| 1,3-dihydro-1'-{3-[N,N-bis(4-fluorophenyl)amino]propyl}-spiro[isobenzofuran-1,4'-piperidine]-3-one (68) | 0.23 | >20 |
| 1,3-dihydro-1'-[6-(2,2,2-trifluoroethoxy)pyridin-3-ylcarbonyl-spiro[isobenzofuran-1,4'-piperidine]-3-one | 6.47 | ND |
| 1,3-dihydro-1'-(4-methoxy-3-trifluoromethylbenzoyl)-spiro[isobenzofuran-1,4'-piperidine]-3-one | 6.94 | ND |
| 1,3-dihydro-1'-{4-methyl-2-[N-methyl-N-(4-methoxybenzyl)amino]pentanoyl-spiro[isobenzofuran-1,4'-piperidine]-3-one | 4.13 | ND |
| 1-(4,4-bis(4-fluorophenyl)butyl-spiro[piperidine-4,5'-cyclopenta[b]pyridine] (10) | 0.31 | 2.72 |
| 1-(4-isopropylbenzyl)-spiro[piperidine-4,5'-cyclopenta[b]pyridine] (21) | 2.35 | 10-20 |
| 1-(N-trifluoromethylcarbonyl-1,2,3,4-tetrahydroisoquinolin-6-yl-sulfonyl)-spiro[piperidine-4,5'-cyclopenta[b]pyridine] | 5.61 | ND |
| 1,3-dihydro-1'-(3,3-diphenylpropanoyl)-spiro[isobenzofuran-1,4'-piperidine]-3-one | 2.66 | ND |
| 1,3-dihydro-1'-[4,4-bis(4-fluorophenyl)butanoyl]-spiro[isobenzofuran-1,4'-piperidine]-3-one (14) | 0.69 | 0.31 |
| 1,3-dihydro-1'-{2-[N,N-bis(4-fluorophenyl)-aminocarbonyl]ethyl}-spiro[isobenzofuran-1,4'-piperidine]-3-one | 1.64 | ND |
| 1,3-dihydro-1'-{2-[N,N,-bis(4-fluorophenyl)aminocarbonyl]ethan-1-oyl)-spiro[isobenzofuran-1,4'-piperidine]-3-one (75) | 5.79 | ND |
| 1,3-dihydro-1'-[N,N,-bis(4-fluorophenyl)aminocarbonylmethyl]-spiro[isobenzofuran-1,4'-piperidine]-3-one (71) | 4.89 | ND |
| 1,3-dihydro-1'-[4-(4-fluorophenyl)-4-oxo-butanoyl]-spiro[isobenzofuran-1,4'-piperidine]-3-one | 10-20 | ND |
| 1,3-dihydro-1'-(4-methoxy-3-trifluoromethylbenzoyl)-spiro[isobenzofuran-1,4'-piperidine]-3-one | 10-20 | ND |
| 1,3-dihydro-1'-(6-methoxypyridin-3-ylcarbonyl)-spiro[isobenzofuran-1,4'-piperidine]-3-one | 10-20 | ND |
| 1,3-dihydro-1'-[4-methyl-2-(N-methyl-N-tert-butoxycarbonylamino)pentanoyl]-spiro[isobenzofuran-1,4'-piperidine]-3-one | 10.45 | ND |
| 1-(3,3-diphenylpropanoyl)-spiro[piperidine-4,5'-cyclopenta[b]pyridine | 3.52 | ND |
| 1-(4,4-bis(4-fluorophenyl)-but-3-enoyl)-spiro[piperidine-4,5'-cyclopenta[b]pyridine] (17) | 0.92 | 1.61 |
| 1-(4,4-bis(4-fluorophenyl)-butanoyl)-spiro[piperidine-4,5'-cyclopenta[b]pyridine] (15) | 0.85 | 0.46 |
| 1-(4-dimethylaminobenzoyl)-spiro[piperidine-4,5'-cyclopenta[b]pyridine] (23) | 10.05 | ND |
| 1-(4-methoxy-3-trifluoromethylbenzyl)-spiro[piperidine-4,5'-cyclopenta[b]pyridine] | 10-20 | ND |
| 1-(4-isopropylbenzoyl)-spiro[piperidine-4,5'-cyclopenta[b]pyridine] | 10-20 | ND |
| 1-(4-methoxybenzyl)-spiro[piperidine-4,5'-cyclopenta[b]pyridine] (19) | 2.92 | ND |
| 1-[2-(10,11-dihydro-5H-dibenzo[a,d]cyclohepten-5-ylmethenyl)ethyl]-spiro[piperidine-4,5'-cyclopenta[b]pyridine] | 0.55 | 3.78 |
| 1-(benzo[b]thiophen-2-ylcarbonyl)-spiro(piperidine-4,5'-cyclopenta[b]pyridine] | 10-20 | ND |
| 1-(4-trifluoromethylphenylsulfonyl)-spiro[piperidine-4,5'-cyclopenta[b]pyridine] (25) | 6.12 | ND |
| 1-[4,4-bis(4-fluorophenyl)butyl]-6',7'-dihydro-spiro[piperidine-4,5'-cyclopenta[b]pyrdine] (31) | 0.34 | 0.71 |
| 1-[4,4-bis.(4-fluorophenyl)butanoyl]-5',7'-dihydro-spiro[piperidine-4,5'-cyclopenta[b]pyridine] (36) | 0.67 | 0.38 |
| 1-(4-iso-propylbenzyl)-6',7'-dihydro-spiro[piperidine-4,5'-cyclopenta[b]pyridine] (38) | 4.30 | ND |
| 1-(3-trifluoromethyl-4-methoxyphenyl)-6',7'-dihydro-spiro[piperidine-4,5'-cyclopenta[b]pyridine (40) | 4.34 | ND |
| 1-[4,4-bis(4-fluorophenyl)but-3-enoyl]-spiro[piperidine-4,1'-indene] (33) | 5.59 | ND |
| 1-[4,4-bis(4-fluorophenyl)butanoyl]-spiro[piperidine-4,1'-indene] (34) | 10-20 | ND |
| 1-(methoxybenzyl)-spiro[piperidine-4,1'-indene] (37) | 0.82 | 5.44 |
| 1-(3-trifluoromethyl-4-methoxybenzoyl)-spiro[piperidine-4,1'-indene] | 2.29 | 5.74 |
| 1-[4,4-bis(4-fluorophenyl)butanoyl]-spiro[piperidine-4,1'-indane] (35) | 4.92 | >20 |
| 1,3-dihydro-1'-[4,4-bis(4-fluorophenyl)butyl]-spiro[isobenzofuran-1,4'-piperidine] (42) | 1.20 | 2.56 |
| 2-benzyl-2,3-dihydro-1'-[4,4-bis(4-fluorophenyl)butyl]-spiro[isoindole-1,4'-piperidine]-3-one (51) | 0.55 | 6.39 |
| 2,3-dihydro-1'-[4,4-bis(4-fluorophenyl)butyl]-spiro[isoindole-1,4'-piperdine]-3-one | 0.34 | >20 |
| 2,3-dihydro-1'-[4,4-bis(4-fluorophenyl)butyl]-spiro[indole-3,4'-piperidine] (60) | 1.05 | 3.80 |
| 1-benzyl-2,3-dihydro-1'-[4,4-bis(4-fluorophenyl)butyl]-spiro[indole-3,4'-piperidine] | 3.14 | >20 |

ND = not determined

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

The invention claimed is:
1. A compound of Formula I:

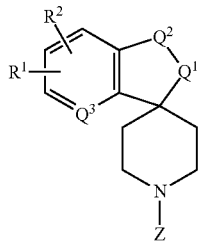

or a pharmaceutically acceptable salt thereof, wherein:
$R^1$ and $R^2$ are each independently selected from the group consisting of hydrogen, alkyl, alkoxy, halogen, and —C(O)Y, wherein Y is hydroxy, alkoxy, amino, alkylamino, or dialkylamino;
$Q^1$ is —C(O)— or $CR^{20}R^{24}$;
$Q^2$ is —C(O)— or $CR^{21}R^{22}$; and
$Q^3$ is $CR^{23}$;
$R^{20}$, $R^{21}$, $R^{22}$, and $R^{24}$ are each independently selected from the group consisting of hydrogen and alkyl; or
$R^{20}$ and $R^{21}$ together form a bond and $R^{22}$ and $R^{24}$ are independently hydrogen or alkyl;
$R^{23}$ is hydrogen or alkyl;
Z is selected from the group consisting of $Z^1$, $Z^2$, $Z^3$, and $Z^5$, wherein:
$Z^1$ is

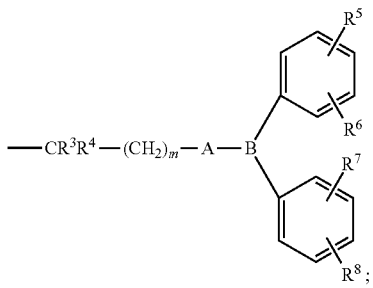

$Z^2$ is
—$CR^3R^4$—$(CH_2)_n$-D-$R^9$;
$Z^3$ is
—$SO_2$—$R^{10}$;
$Z^4$ is

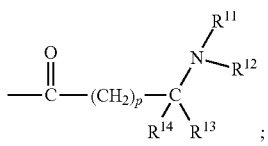

and
$Z^5$ is

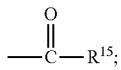

$R^3$ and $R^4$ are both hydrogen or together form =O;
$R^5$, $R^6$, $R^7$ and $R^8$ are each independently selected from the group consisting of hydrogen, alkyl, alkoxy, halogen, haloalkyl, haloalkoxy, hydroxy, hydroxyalkyl, cyano, amino, aminoalkyl, alkylamino, and dialkylamino;
$R^9$ is selected from the group consisting of
phenyl optionally substituted with one or two substituents independently selected from the group consisting of alkyl, alkoxy, halogen, haloalkyl, haloalkoxy, hydroxy, hydroxyalkyl, cyano, amino, aminoalkyl, alkylamino, and dialkylamino, or two substituents in adjacent carbon atoms in the phenyl ring optionally form a bridge —O—$CH_2$—O—; and
pyridyl substituted with one or two substituents independently selected from the group consisting of alkyl, haloalkyl, halogen, haloalkoxy, and alkoxy;
$R^{10}$ is
phenyl optionally substituted with one or two substituents independently selected from the group consisting of alkyl, alkoxy, halogen, haloalkyl, haloalkoxy, amino, alkylamino, dialkylamino, and alkylcarbonylamino; or
1,2,3,4-tetrahydroquinolinyl or 1,2,3,4-tetrahydroisoquinolinyl optionally substituted at the nitrogen atom with alkylcarbonyl or haloalkylcarbonyl;
$R^{11}$ and $R^{12}$ are each independently selected from the group consisting of
hydrogen, alkyl, alkenyl, alkoxycarbonyl, hydroxyalkyl, haloalkyl, mercaptoalkyl, aminoalkyl;
phenyl optionally substituted with one or two substituents independently selected from the group consisting of alkyl, alkoxy, halogen, and haloalkyl; and
benzyl, wherein the phenyl ring is optionally substituted with one or two substituents independently selected from the group consisting of alkyl, alkoxy, halogen, and haloalkyl;
$R^{13}$ is hydrogen and $R^{14}$ is selected from the group consisting of hydrogen, alkyl, hydroxyalkyl, alkoxyalkyl, haloalkyl, and aminoalkyl;
$R^{15}$ is selected from the group consisting of alkylthioalkyl, 2-benzo[b]thienyl, 3-benzo[b]thienyl, 1-benzo[c]thienyl, 3-benzo[c]thienyl, 2-benzofuryl, 3-benzofuryl, 1-isobenzofuryl, 3-isobenzofuryl, 4-morpholinyl, 4-thiomorpholinyl, 1-piperazinyl, 1-piperidinyl, and 1-pyrrolidinyl;
A is —C(O)—, $CH_2$, or is absent, and B is CH or N; or
A-B is CH=C (where CH is attached to —$(CH_2)_m$—);
D is —C(O)— or is absent;
m is 0, 1, 2, 3, 4, or 5;
n is 0, 1, 2, or 3; and
p is 0 or 1;
with the following provisos:
1) when $Q^1$ is $CR^{20}R^{24}$ and $Q^2$ is $CR^{21}R^{22}$ or —C(O)—, or $Q^1$ is $CR^{20}R^{24}$ or —C(O)— and $Q^2$ is $CR^{21}R^{22}$, Z is $Z^1$, A is $CH_2$ or absent, and B is CH, then $R^3$ and $R^4$ together form =O;
2) when $Q^1$ is $CR^{20}R^{24}$ and $Q^2$ is $CR^{21}R^{22}$ or —C(O)—, or $Q^1$ is $CR^{20}R^{24}$ or —C(O)— and $Q^2$ is $CR^{21}R^{22}$, Z is $Z^2$, n is 0 or 1, and D is absent, then $R^9$ is not an optionally substituted phenyl; or
3) when $Q^1$ is $CR^{20}R^{24}$, $Q^2$ is $C^{21}R^{22}$, and Z is $Z^3$, then $R^{10}$ is not an optionally substituted phenyl.

2. The compound of claim 1, having a) the Formula V:

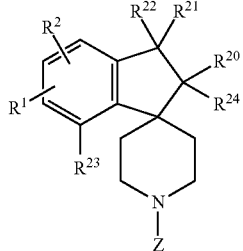

V wherein $R^1, R^2, R^{20}, R^{21}, R^{22}, R^{23}, R^{24}$ and Z are as defined in claim 1, or a pharmaceutically acceptable salt thereof; or b) the Formula VI:

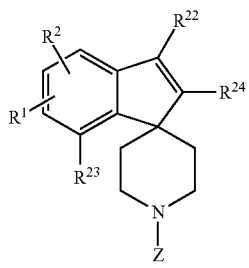

VI wherein $R^1, R^2, R^{22}, R^{23}, R^{24}$ and Z are as defined in claim 1, or a pharmaceutically acceptable salt thereof; or c), the Formula XVIII:

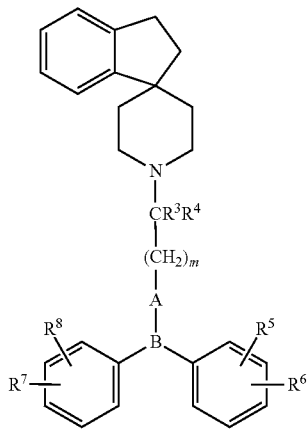

XVIII or a pharmaceutically acceptable salt thereof, wherein $R^3$-$R^8$, A, B, and m are as defined in claim 1, with the proviso that when A is $CH_2$ or absent and B is CH, then $R^3$ and $R^4$ together form =O; or d) the Formula XX:

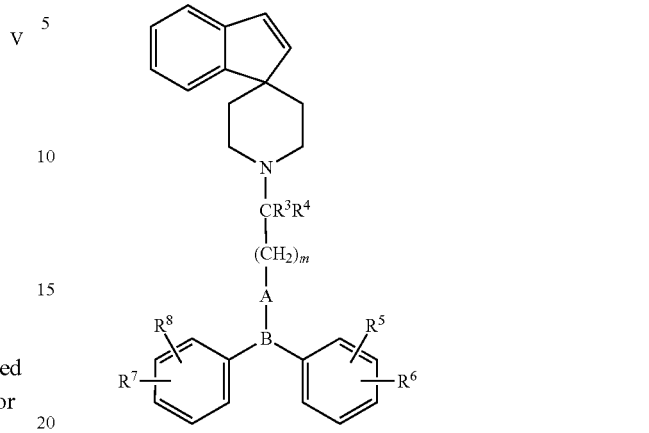

XX or a pharmaceutically acceptable salt thereof, wherein $R^3$-$R^8$, A, B, and m are as defined in claim 1, with the proviso that when A is $CH_2$ or absent and B is CH, then $R^3$ and $R^4$ together form =O.

3. The compound of claim 2, wherein Z is $Z^1, Z^2, Z^3, Z^4$ or $Z^5$.

4. The compound of claim 2, wherein $R^1$ and $R^2$ are both hydrogen.

5. The compound of claim 1, wherein
   a) $R^3$ and $R^4$ together form =O and Z is $Z^1$; or
   b) $R^3$ and $R^4$ are both hydrogen, Z is $Z^2$ and n is 0.

6. The compound of claim 3, wherein
   a) Z is $Z^1$ and $R^5, R^6, R^7$ and $R^8$ are each independently selected from the group consisting of hydrogen, alkyl, alkoxy, halogen, haloalkyl, hydroxy, cyano, amino, alkylamino, and dialkylamino; or
   b) Z is $Z^2$ and
      i. $R^9$ is phenyl optionally substituted with one or two substituents independently selected from the group consisting of alkyl, alkoxy, halogen, haloalkyl, haloalkoxy, hydroxy, hydroxyalkyl, cyano, amino, aminoalkyl, alkylamino, and dialkylamino; or
      ii. $R^9$ is pyridyl substituted with one or two substituents independently selected from the group consisting of alkyl, haloalkyl, halogen, haloalkoxy, and alkoxy; or
   (c) Z is $Z^3$ and
      i. $R^{10}$ is phenyl optionally substituted with one or two substituents independently selected from the group consisting of alkyl, alkoxy, halogen, haloalkyl, haloalkoxy, amino, alkylamino, dialkylamino, and alkylcarbonylamino; or
      ii. $R^{10}$ is 1,2,3,4-tetrahydroquinolinyl or 1,2,3,4-tetrahydroisoquinolinyl optionally substituted at the nitrogen atom with alkylcarbonyl or haloalkylcarbonyl; or
   (d) Z is $Z^4$ and
      iii. $R^{11}$ and $R^{12}$ are each independently selected from the group consisting of hydrogen; alkyl; alkoxycarbonyl; phenyl optionally substituted with one or two substituents independently selected from the group consisting of alkyl, alkoxy, halogen, and haloalkyl; and benzyl optionally substituted at the phenyl ring with one or two substituents independently selected from the group consisting of alkyl, alkoxy, halogen, and haloalkyl; or iv. $R^{14}$ is selected from the group consisting of alkyl, hydroxyalkyl, alkoxyalkyl, haloalkyl, and aminoalkyl; or (e) Z is $Z^5$ and $R^{15}$ is selected from the group consisting of 2-benzo[b]thienyl, 3-benzo[b]thienyl, 1-benzo[c]thienyl, 3-benzo[c]thienyl, 2-benzofuryl, 3-benzofuryl, 1-isobenzofuryl, and 3-isobenzofuryl.

7. A compound, wherein said compound is:

1-[4,4-bis(4-fluorophenyl)but-3-enoyl]-spiro[piperidine-4,1'-indene];

1-[4,4-bis(4-fluorophenyl)butanoyl]-spiro[piperidine-4,1'-indene];

1-(methoxybenzyl)-spiro[piperidine-4,1'-indene];

1-(3-trifluoromethyl-4-methoxybenzoyl)-spiro[piperidine-4,1'-indene];

1-[4,4-bis(4-fluorophenyl)butanoyl]-spiro[piperidine-4,1'-indane];

or a pharmaceutically acceptable salt, prodrug or solvate thereof.

8. The compound of claim 1, wherein said compound has an $IC_{50}$ of about 100 μM or less for N-type calcium channel blocking activity in a calcium mobilization and/or electrophysiological assay.

9. A pharmaceutical composition, comprising a compound of claim 1 and a pharmaceutically acceptable carrier.

10. A method of treating or ameliorating pain in a mammal suffering from pain, comprising administering to a mammal in need of such treatment or amelioration an effective amount of a compound of Formula I set forth in claim 1, or a pharmaceutically acceptable salt thereof.

11. A method of treating or ameliorating chronic pain or neuropathic pain in a mammal, comprising administering an effective amount of a compound of claim 1, or a pharmaceutically acceptable salt thereof.

12. A method of blocking N-type and/or L-type calcium channels in a mammal, comprising administering to the mammal at least one compound of claim 1, or a pharmaceutically acceptable salt thereof.

13. The method of claim 10, wherein said pain is chronic pain, acute pain, or surgical pain.

* * * * *